United States Patent
Manoharan et al.

(10) Patent No.: US 9,725,479 B2
(45) Date of Patent: Aug. 8, 2017

(54) 5'-END DERIVATIVES

(75) Inventors: Muthiah Manoharan, Weston, MA (US); Kallanthottathil G. Rajeev, Wayland, MA (US); Ivan Zlatev, Cambridge, MA (US); Eric E. Swayze, Encinitas, CA (US); Thazha P. Prakash, Carlsbad, CA (US); Walter F. Lima, San Diego, CA (US)

(73) Assignees: Ionis Pharmaceuticals, Inc., Carlsbad, CA (US); Alaylam Pharmacueuticals, Inc., Cambridge, MA (US)

(*) Notice: Subject to any disclaimer, the term of this patent is extended or adjusted under 35 U.S.C. 154(b) by 1156 days.

(21) Appl. No.: 13/696,796

(22) PCT Filed: Apr. 22, 2011

(86) PCT No.: PCT/US2011/033592
§ 371 (c)(1),
(2), (4) Date: Aug. 23, 2013

(87) PCT Pub. No.: WO2011/133871
PCT Pub. Date: Oct. 27, 2011

(65) Prior Publication Data
US 2013/0323836 A1 Dec. 5, 2013

Related U.S. Application Data

(60) Provisional application No. 61/326,960, filed on Apr. 22, 2010.

(51) Int. Cl.
*C07H 17/02* (2006.01)
*C07H 19/067* (2006.01)
*C07H 21/02* (2006.01)
*C12N 15/113* (2010.01)

(52) U.S. Cl.
CPC .......... *C07H 17/02* (2013.01); *C07H 19/067* (2013.01); *C07H 21/02* (2013.01); *C12N 15/113* (2013.01); *C12N 15/1137* (2013.01); *C12N 2310/14* (2013.01); *C12N 2310/315* (2013.01); *C12N 2310/321* (2013.01); *C12N 2310/322* (2013.01); *C12N 2310/344* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,235,871 A | 11/1980 | Papahadjopoulos et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,643,988 A | 2/1987 | Segrest et al. |
| 4,667,025 A | 5/1987 | Miyoshi et al. |
| 4,725,677 A | 2/1988 | Koester et al. |
| 4,737,323 A | 4/1988 | Martin et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,876,335 A | 10/1989 | Yamane et al. |
| 4,897,355 A | 1/1990 | Eppstein et al. |
| 4,904,582 A | 2/1990 | Tullis |
| 4,948,882 A | 8/1990 | Ruth |
| 4,958,013 A | 9/1990 | Letsinger |
| 5,013,556 A | 5/1991 | Woodle et al. |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,802 A | 6/1992 | Smith et al. |
| 5,128,318 A | 7/1992 | Levine et al. |

(Continued)

FOREIGN PATENT DOCUMENTS

| | | |
|---|---|---|
| CA | 2138925 | 7/1995 |
| EP | 0353267 | 2/1990 |

(Continued)

OTHER PUBLICATIONS

Uhlmann, E. et al., Chemical Reviews, "Antisense Oligonucleotides: A New Therapeutic Principle", 1990, vol. 90, No. 4, pp. 543-584.*
Dexter, E. J. et al., Inflammation Research, "The effect of adenosine and its analogues on histamine release from mast cells", 1999, vol. 48, Supplement 1, pp. S7-S8.*
Laurent, A. et al., Nucleic Acids Research, "Chiral and steric effects in the efficient binding of alpha-anomeric deoxyoligonucleoside N-alkylphosphoramidates to ssDNA and RNA", 1999, vol. 27, No. 21, pp. 4151-4159.*

(Continued)

*Primary Examiner* — Layla Berry
*Assistant Examiner* — Bahar Craigo
(74) *Attorney, Agent, or Firm* — Ionis Patent Department

(57) ABSTRACT

The present invention provides compounds of formula (1). Another aspect of the invention relates to a method of inhibiting the expression of a gene in call, the method comprising (a) contacting an oligonucleotide of the invention with the cell; and (b) maintaining the cell from step (a) for a time sufficient to obtain degradation of the mRNA of the target gene.

(1)

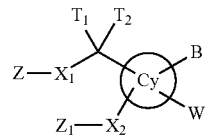

15 Claims, 1 Drawing Sheet

(56) References Cited

U.S. PATENT DOCUMENTS

| | | |
|---|---|---|
| 5,130,302 A | 7/1992 | Spielvogel et al. |
| 5,138,045 A | 8/1992 | Cook et al. |
| 5,142,047 A | 8/1992 | Summerton et al. |
| RE34,069 E | 9/1992 | Koster et al. |
| 5,149,782 A | 9/1992 | Chang et al. |
| 5,166,315 A | 11/1992 | Summerton et al. |
| 5,171,678 A | 12/1992 | Behr et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler |
| 5,212,295 A | 5/1993 | Cook |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,223,618 A | 6/1993 | Cook et al. |
| 5,235,033 A | 8/1993 | Summerton et al. |
| 5,245,022 A | 9/1993 | Weis et al. |
| 5,254,469 A | 10/1993 | Warren et al. |
| 5,256,775 A | 10/1993 | Froehler |
| 5,258,506 A | 11/1993 | Urdea et al. |
| 5,262,536 A | 11/1993 | Hobbs |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,321,131 A | 6/1994 | Agrawal et al. |
| 5,359,044 A | 10/1994 | Cook et al. |
| 5,366,878 A | 11/1994 | Pederson et al. |
| 5,371,241 A | 12/1994 | Brush |
| 5,378,825 A | 1/1995 | Cook et al. |
| 5,386,023 A | 1/1995 | Sanghvi et al. |
| 5,391,723 A | 2/1995 | Priest |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,434,257 A | 7/1995 | Matteucci et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,191 A | 10/1995 | Cook et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,506,351 A | 4/1996 | Mcgee |
| 5,508,270 A | 4/1996 | Baxter et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,521,302 A | 5/1996 | Cook |
| 5,525,465 A | 6/1996 | Haralambidis et al. |
| 5,527,899 A | 6/1996 | Froehler |
| 5,534,499 A | 7/1996 | Ansell |
| 5,536,821 A | 7/1996 | Agrawal et al. |
| 5,539,082 A | 7/1996 | Nielsen et al. |
| 5,539,083 A | 7/1996 | Cook et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,554,746 A | 9/1996 | Ravikumar et al. |
| 5,561,225 A | 10/1996 | Maddry et al. |
| 5,563,253 A | 10/1996 | Agrawal et al. |
| 5,565,552 A | 10/1996 | Magda et al. |
| 5,565,555 A | 10/1996 | Froehler et al. |
| 5,567,810 A | 10/1996 | Weis et al. |
| 5,571,799 A | 11/1996 | Tkachuk et al. |
| 5,571,902 A | 11/1996 | Ravikumar et al. |
| 5,574,142 A | 11/1996 | Meyer, Jr. et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold et al. |
| 5,587,361 A | 12/1996 | Cook et al. |
| 5,587,371 A | 12/1996 | Sessler et al. |
| 5,587,469 A | 12/1996 | Cook et al. |
| 5,587,470 A | 12/1996 | Cook et al. |
| 5,591,584 A | 1/1997 | Chang et al. |
| 5,595,726 A | 1/1997 | Magda et al. |
| 5,596,086 A | 1/1997 | Matteucci |
| 5,597,696 A | 1/1997 | Linn et al. |
| 5,599,797 A | 2/1997 | Cook et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,633,360 A | 5/1997 | Bishofberger et al. |
| 5,646,269 A | 7/1997 | Matteucci et al. |
| 5,663,312 A | 9/1997 | Chaturvedula |
| 5,672,662 A | 9/1997 | Harris et al. |
| 5,672,697 A | 9/1997 | Buhr et al. |
| 5,677,437 A | 10/1997 | Teng et al. |
| 5,677,439 A | 10/1997 | Weis et al. |
| 5,688,941 A | 11/1997 | Cook et al. |
| 5,714,166 A | 2/1998 | Tomalia et al. |
| 5,721,218 A | 2/1998 | Froehler |
| 5,792,608 A | 8/1998 | Swaminathan et al. |
| 5,820,873 A | 10/1998 | Choi et al. |
| 5,885,613 A | 3/1999 | Holland et al. |
| 6,153,737 A | 11/2000 | Manoharan et al. |
| 6,172,208 B1 | 1/2001 | Cook |
| 6,262,241 B1 | 7/2001 | Cook et al. |
| 6,300,319 B1 | 10/2001 | Manoharan |
| 6,320,017 B1 | 11/2001 | Ansell |
| 6,335,434 B1 | 1/2002 | Guzaev et al. |
| 6,335,437 B1 | 1/2002 | Manoharan |
| 6,444,806 B1 | 9/2002 | Veerapanani et al. |
| 6,486,308 B2 | 11/2002 | Kutyavin et al. |
| 6,525,031 B2 | 2/2003 | Manoharan |
| 6,528,631 B1 | 3/2003 | Cook et al. |
| 6,559,279 B1 | 5/2003 | Manoharan et al. |
| 7,626,014 B2 | 12/2009 | Manoharan et al. |
| 7,745,608 B2 | 6/2010 | Manoharan et al. |
| 8,034,921 B2 | 10/2011 | Manoharan et al. |
| 2002/0151512 A1* | 10/2002 | Peyman et al. .......... 514/44 |
| 2004/0043959 A1* | 3/2004 | Bloom .................. A61K 31/52 514/46 |
| 2004/0106785 A1* | 6/2004 | Deziel .................. C07H 19/04 536/28.4 |
| 2005/0164235 A1 | 7/2005 | Manoharan et al. |
| 2005/0261218 A1 | 11/2005 | Esau et al. |
| 2006/0166910 A1 | 7/2006 | Tuschl et al. |
| 2007/0123482 A1 | 5/2007 | Stoffel et al. |
| 2007/0213292 A1 | 9/2007 | Stoffel et al. |

FOREIGN PATENT DOCUMENTS

| | | |
|---|---|---|
| WO | WO 87/02062 | 4/1987 |
| WO | WO 92/20822 | 11/1992 |
| WO | WO 92/20823 | 11/1992 |
| WO | WO 93/23569 | 11/1993 |

(56) References Cited

FOREIGN PATENT DOCUMENTS

| | | |
|---|---|---|
| WO | WO 94/02595 | 2/1994 |
| WO | WO 96/14057 | 11/1995 |
| WO | WO 96/37194 | 11/1996 |
| WO | WO 98/39359 | 11/1998 |
| WO | WO 99/05144 | 2/1999 |
| WO | WO 00/44895 | 8/2000 |
| WO | WO 00/44914 | 9/2000 |
| WO | WO 01/36646 | 5/2001 |
| WO | WO 01/75164 | 10/2001 |
| WO | WO 02/44321 | 6/2002 |
| WO | WO 2004/080406 | 3/2004 |
| WO | WO 2008/042973 | 8/2008 |
| WO | WO 2009/006089 | 1/2009 |
| WO | WO 2009/073809 | 11/2009 |
| WO | WO 2010/054384 | 5/2010 |
| WO | WO 2010/054401 | 5/2010 |

OTHER PUBLICATIONS

Adelfinskaya et al., "Amino acid phosphoramidate nucleotides as alternative substrates for HIV-1 reverse transcriptase" Angew. Chem. Int. Ed. Engl. (2007) 46(23):4356-4358.

Adelfinskaya et al., "Polymerase-catalyzed synthesis of DNA from phosphoramidate conjugates of deoxynucleotides and amino acids" Nucleic Acids Res. (2007) 35(15):5060-5072.

Allen et al., "A new strategy for attachment of antibodies to sterically stabilized liposomes resulting in efficient targeting to cancer cells" Biochim. Biophys. Acta. (1995) 1237(2):99-108.

An et al., "Synthesis of novel 3'-C-methylene thymidine and 5-methyluridine/cytidine H-phosphonates and phosphonamidites for new backbone modification of oligonucleotides" J. Org. Chem. (2001) 66(8):2789.2801.

Angeloff et al., "Characterization of a 5'-Aldehyde Terminus Resulting from the Oxidative Attack at C5' of a 2-Deoxyribose on DNA" Chem. Res. Toxicol. (2001) 14(10):1413-1420.

Aoki et al., "Potential tumor-targeting peptide vector of histidylated oligolysine conjugated to a tumor-homing RGD motif" Cancer Gene Ther. (2001) 8(10):783-787.

Ausin et al., "Synthesis of amino- and guanidino-G-clamp PNA monomers" Org. Lett. (2002) 4(23):4073-4075.

Beaucage et al., "Advances in the Synthesis of Oligonucleotides by the Phosphoramidite Approach" Tetrahedron (1992) 48(12):2223-2311.

Beaucage et al., "The Functionalization of Oligonucleotides Via Phosphoramidite Derivatives" Tetrahedron (1993) 49(10):1925-1963.

Beaucage et al., "The Synthesis of Specific Ribonucleotides and Unrelated Phosphorylated Biomolecules by the Phosphoramidite Method" Tetrahedron (1993) 49(46):10441-10488.

Berge et al., "Pharmaceutical salts" J. Pharm. Sci. (1977) 66(1):1-19.

Blume et al., "Specific targeting with poly(ethylene glycol)-modified liposomes: coupling of homing devices to the ends of the polymeric chains combines effective target binding with long circulation times" Biochim. Biophys. Acta. (1993) 1149(1):180-184.

Bonomo et al., "A rapid method for the synthesis of protein-lipid complexes using adsorption chromatography" J. Lipid Res. (1988) 29(3):380-384.

Chaloin et al., "Design of carrier peptide-oligonucleotide conjugates with rapid membrane translocation and nuclear localization properties" Biochem. Biophys. Res. Commun. (1998) 243(2):601-608.

Colledge et al., "Disruption of c-mos causes parthenogenetic development of unfertilized mouse eggs" Nature (1994) 370(6484):65-68.

Constantinides et al., "Formulation and intestinal absorption enhancement evaluation of water-in-oil microemulsions incorporating medium-chain glycerides" Pharm. Res. (1994) 11(10):1385-1390.

Cormier et al., "Synthesis of hexanucleotide analogues containing diisopropylsilyl internucleotide linkages" Nucleic Acids Res. (1988) 16(10):4583-4594.

Dang et al., "Discovery of potent and specific fructose-1,6-bisphosphatase inhibitors and a series of orally-bioavailable phosphoramidase-sensitive prodrugs for the treatment of type 2 diabetes" J. Am. Chem. Soc. (2007) 129(50):15491-15502.

Defrees et al., "Sialyl Lewis x Liposomes as a Multivalent Ligand and Inhibitor of E-Selectin Mediated Cellular Adhesion" J. Am. Chem. Soc. (1996) 118(26):6101-6104.

Derossi et al., "The third helix of the Antennapedia homeodomain translocates through biological membranes" J. Biol. Chem. (1994) 269(14):10444-10450.

Drontle et al., "Designing a pronucleotide stratagem: lessons from amino acid phosphoramidates of anticancer and antiviral pyrimidines" Mini Rev. Med. Chem. (2004) 4:409-419.

Eaton, "The joys of in vitro selection: chemically dressing oligonucleotides to satiate protein targets" Curr. Opin. Chem. Biol. (1997) 1(1):10-16.

Eckstein, "Oligonucleotides and Analogues: A Practical Approach" Ed. F. Eckstein, IRL Press, 1991.

Edge et al., "Synthetic analogues of polynucleotides. 8. Analogues of oligonucleotides containing carboxymethylthymidine" J. Chem. Soc. Perkin 1 (1972) 16:1991-1996.

Elbashir et al., "Functional anatomy of siRNAs for mediating efficient RNAi in Drosophila melanogaster embryo lysate" EMBO. J. (2001) 20(23):6877-6888.

Ellington et al., "In vitro selection of RNA molecules that bind specific ligands" Nature (1990) 346(6287):818-822.

Elmquist et al., "VE-cadherin-derived cell-penetrating peptide, pVEC, with carrier functions" Exp. Cell Res. (2001) 269(2):237-244.

Englisch et al., "Chemically Modified Oligonucleotides as Probes and Inhibitors" Agnew Chem. Int. Ed. Engl. (1991) 30:613-629.

Erion et al., "MB06322 (CS-917): A potent and selective inhibitor of fructose 1,6-bisphosphatase for controlling gluconeogenesis in type 2 diabetes" Proc. Natl. Acad. Sci. U.S.A. (2005) 102(22):7970-7975.

Famulok, "Oligonucleotide aptamers that recognize small molecules" Curr. Opin. Struct. Biol. (1999) 9(3):324-329.

Felgner et al., "Lipofection: a highly efficient, lipid-mediated DNA-transfection procedure" Proc. Natl. Acad. Sci. (1987) 8:7413-7417.

Flanagan et al., "A cytosine analog that confers enhanced potency to antisense oligonucleotides" Proc. Natl. Acad. Sci. U.S.A. (1999) 96(7):3513-3518.

Franceschini et al., "Apolipoprotein AIMilano. Accelerated binding and dissociation from lipids of a human apolipoprotein variant" J. Biol. Chem. (1985) 260(30):16321-16325.

Giraut et al., "Iminodiacetic-phosphoramidates as metabolic prototypes for diversifying nucleic acid polymerization in vivo" Nucleic Acids Res. (2010) 38(8):2541-2550.

Goraczniak et al., "Gene silencing by synthetic U1 adaptors" Nat. Biotechnol. (2009) 27(3):257-263.

Green and Wuts, Oligonucleotides and Analogues a Practical Approach, Ekstein, F. Ed., IRL Press, N.Y, 1991.

Griffiths-Jones et al., "miRBase: microRNA sequences, targets and gene nomenclature" Nucleic Acids Res. (2006) 34(Database issue):D140-D144.

Griffiths-Jones, "The microRNA Registry" Nucleic Acids Res. (2004) 32(Database issue):D109-D111.

Grob et al., "Fragmentierung von alpha-Aminoketoximen. Iv. Teil Der Einfluss sterischer. Faktoren Fragmentierungsreaktion, 17. Mitteilung" Helvetica Chimica Acta (1967) 50(8):2520-2531.

Hashimoto et al., "Parthenogenetic activation of oocytes in c-mos-deficient mice" (1994) 370(6484):68-71.

Haubner et al., "Glycosylated RGD-containing peptides: tracer for tumor targeting and angiogenesis imaging with improved biokinetics" J. Nucl. Med. (2001) 42(2):326-336.

Hecker et al., "Prodrugs of phosphates and phosphonates" J. Med. Chem. (2008) 51:2328-2345.

Hermann et al., "Adaptive recognition by nucleic acid aptamers" Science (2000) 287(5454):820-825.

Ho et al., "Preparation of microemulsions using polyglycerol fatty acid esters as surfactant for the delivery of protein drugs" J. Pharm. Sci. (1996) 85(2):138-143.

(56) References Cited

OTHER PUBLICATIONS

Holmes et al., "Steric inhibition of human immunodeficiency virus type-1 Tat-dependent trans-activation in vitro and in cells by oligonucleotides containing 2'-O-methyl G-clamp ribonucleoside analogues" Nucleic Acids Res. (2003) 31(11):2759-2768.
Holmes et al., "The synthesis of 2'-O-methyl G-clamp containing oligonucleotides and their inhibition of the HIV-1 Tat-TAR interaction" Nucleosides Nucleotides Nucleic Acids (2003) 22(5-8):1259-1262.
Holmquist et al., "A selective method for the direct conversion of aldehydes into .beta.-keto esters with ethyl diazoacetate catalyzed by tin(II) chloride" J. Org. Chem. (1989) 54(14):3259.
Hyrup et al., "Peptide nucleic acids (PNA): synthesis, properties and potential applications" Bioorg. Med. Chem. (1996) 4(1):5-23.
Izumiya et al., "Stereochemistry of the Conversion of Allylglycine to γ-Hydroxyornithine and 4-Hydroxyproline" J. Am. Chem. Soc. (1963) 85(12):1835-1839.
Jones et al., "Synthesis and anti-HIV Activity of Some Novel Phosphorodiamidate Derivatives of 3'-azido-3'-deoxythymidine (AZT)" Antivir. Vhem. Chemother. (1991) 2:35-39.
Kawasaki et al., "Uniformly modified 2'-deoxy-2'-fluoro phosphorothioate oligonucleotides as nuclease-resistant antisense compounds with high affinity and specificity for RNA targets" J. Med. Chem. (1993) 36(7):831-841.
Kim et al., "Three-dimensional model of the active site of the self-splicing rRNA precursor of Tetrahymena" Proc. Natl. Acad. Sci. U.S.A. (1987) 84(24):8788-8792.
Kirpotin et al., "Liposomes with detachable polymer coating: destabilization and fusion of dioleoylphosphatidylethanolamine vesicles triggered by cleavage of surface-grafted poly(ethylene glycol)" FEBS Lett. (1996) 388(2-3):115-118.
Krutzfeldt et al., "Silencing of microRNAs in vivo with 'antagomirs'" Nature (2005) 438(7068):685-689.
Lam et al., "A new type of synthetic peptide library for identifying ligand-binding activity" Nature (1991) 354(6348):82-84.
Le Bouc et al., "Diastereoselective syntheses of 1-deoxyhomonojirimycin and two new 1,5,6-trideoxy-1,5-iminoheptitols with d-allo- and 1-talo-configuration" Tetrahedron Asymmetry (2006) 17:2006-2014.
Lee et al., "Mucosal penetration enhancers for facilitation of peptide and protein drug absorption" Crit. Rev. Ther. Drug Carrier Syst. (1991) 8(2):91-192.
Maier et al., "Nuclease resistance of oligonucleotides containing the tricyclic cytosine analogues phenoxazine and 9-(2-aminoethoxy)-phenoxazine ("G-clamp") and origins of their nuclease resistance properties" Biochemistry (2002) 41(4):1323-1327.
Mann et al., "Therapeutic applications of transcription factor decoy oligonucleotides" J. Clin. Invest. (2000) 106(9):1071-1075.
Manoharan, "Oligonucleotide conjugates as potential antisense drugs with improved uptake, biodistribution, targeted delivery, and mechanism of action" Antisense Nucleic Acid Drug Dev. (2002) 12(2):103-128.
Manoharan, Antisense Research and Applications, Crooke and LeBleu, eds., CRC Press, Boca Raton, Fla., 1993, Chapter 17.
Martin, "New acces to 2'-O-alkylated ribonucleosides and properties of 2'-O-alkylated oligoribonucleotides" Helv. Chim. Acta. (1995) 78:486-504.
Martin, "Stereoselektive Synthese von 2'-O-(2-Methoxyethyl)ribonucleosiden: Nachbargruppenbeteiligung der Methoxyethoxy-Gruppe bei der Ribosylierung von Heterocyclen" Helv. Chim. Acta (1996) 79(7):1930-1938.
Mastrobattista et al., "Functional characterization of an endosome-disruptive peptide and its application in cytosolic delivery of immunoliposome-entrapped proteins" J. Bio. Chem. (2002) 277(30):27135-27143.
Mi et al., "Characterization of a class of cationic peptides able to facilitate efficient protein transduction in vitro and in vivo" Mol. Ther. (2000) 2(4):339-347.
Michel et al., "Uber Isoxazolidin-3,5-dione" Helvetica Chimica Acta (1965) 48(8):1973-1983.

Mitchell et al., "Polyarginine enters cells more efficiently than other polycationic homopolymers" J. Pept. Res. (2000) 56(5):318-325.
Oberhauser et al., "Enhancing Endosomal Exit of Nucleic Acids Using pH-Sensitive Viral Fusion Peptides" Deliv. Strategies Antisense Oligonucleotide Ther. (1995) 247-266.
Plank et al., "The influence of endosome-disruptive peptides on gene transfer using synthetic virus-like gene transfer systems" J. Biol. Chem. (1994) 269(17):12918-12924.
Pooga et al., "Cell penetration by transportan" FASEB J. (1998) 12(1):67-77.
Rajeev et al., "High-affinity peptide nucleic acid oligomers containing tricyclic cytosine analogues" Org. Lett. (2002) 4(25):4395-4398.
Sanghvi et al., "Carbohydrate Modifications in Antisense Research" Y.S. Sanghvi and P.D. Cook, Eds., ACS Symposium Series 580; Chapters 3 and 4, 40-65.
Sapra et al., "Ligand-targeted liposomal anticancer drugs" Prog. Lipid Res. (2003) 42(5):439-462.
Sheen et al., "Bioavailability of a poorly water-soluble drug from tablet and solid dispersion in humans" J. Pharm. Sci. (1991) 80(7):712-714.
Simeoni et al., "Insight into the mechanism of the peptide-based gene delivery system MPG: implications for delivery of siRNA into mammalian cells" Nucleic Acids Res. (2003) 31(11):2717-2724.
Skoblov et al., "Isoteric triphosphonate analogues of dNTP: Synthesis and substrate properties towards various DNA polymerases" Russian J. Bioorg. Chem. (2007) 33(5):488-498.
Soutschek et al., "Therapeutic silencing of an endogenous gene by systemic administration of modified siRNAs" Nature (2004) 432(7014):173-178.
Sproat et al., "Synthesis of Modified Building Blocks Containing Amino or Thiol Moieties: Application of Modified Oligodeoxyribonucleotides" Nucleosides Nucleotides (1988) 7:651-653.
Stirchak et al., "Uncharged stereoregular nucleic acid analogs: 2. Morpholino nucleoside oligomers with carbamate internucleoside linkages" Nucleic Acids Res. (1989) 17(15):6129-6141.
Subbarao et al., "pH-dependent bilayer destabilization by an amphipathic peptide" Biochemistry (1987) 26(11):2964-2972.
Szoka et al., "Procedure for preparation of liposomes with large internal aqueous space and high capture by reverse-phase evaporation" Proc. Natl. Acad. Sci. U.S.A. (1978) 75(9):4194-4198.
Tittensor, "The preparation of nucleoside carbonates" J. Chem. Soc. Perkin 1 (1971) 15:2656-2662.
Tuerk et al., "Systematic evolution of ligands by exponential enrichment: RNA ligands to bacteriophage T4 DNA polymerase" Science (1990) 249(4968):505-510.
Turk et al., "Characterization of a novel pH-sensitive peptide that enhances drug release from folate-targeted liposomes at endosomal pHs" (2002) 1559(1):56-68.
Verma et al., "Modified oligonucleotides: synthesis and strategy for users" Annu. Rev. Biochem. (1998) 67:99-134.
Vives et al., "A truncated HIV-1 Tat protein basic domain rapidly translocates through the plasma membrane and accumulates in the cell nucleus" J. Biol. Chem. (1997) 272(25):16010-16017.
Vogel et al., "Peptide-Mediated Release of Folate-Targeted Liposome Contents from Endosomal Compartments" J. Am. Chem. Soc. (1996) 118(7):1581-1586.
Wang et al., "Synthesis and evaluation of oligodeoxynucleotides containing 4'-C-substituted thymidines" Tetrahedron Lett. (1996) 37:6515-6518.
Wengel, "Synthesis of 3'-C- and 4'-C-Branched Oligodeoxynucleotides and the Development of Locked Nucleic Acid (LNA)" Acc. Chem. Res. (1999) 32:301-310.
Werner et al., "Preparation of 4-Oxo-1-norvaline via Diazomethane Homologation of β-Aspartyl Semialdehyde" J. Org. Chem. (1997) 62(23):8243-8246.
Wilds et al., "Structural Basis for Recognition of Guanosine by a Synthetic Tricyclic Cytosine Analogue: Guanidinium G-Clamp" Helv. Chim. Acta (2003) 86(4):966-978.
Wolfrum et al., Mechanisms and optimization of in vivo delivery of lipophilic siRNAs) Nat. Biotechnol. (2007) 25(10):1149-1157.

(56) References Cited

OTHER PUBLICATIONS

Zalipsky et al., "Long circulating, cationic liposomes containing amino-PEG-phosphatidylethanolamine" FEBS Lett. (1994) 353(1):71-74.

Zalipsky, "Synthesis of an end-group functionalized polyethylene glycol-lipid conjugate for preparation of polymer-grafted liposomes" Bioconjug. Chem. (1993) 4(4):296-299.

Zitzmann et al., "Arginine-glycine-aspartic acid (RGD)-peptide binds to both tumor and tumor-endothelial cells in vivo" Cancer Res. (2002) 62(18):5139-5143.

Zlatev et al., "Delta-di-carboxybutyl phosphoramidate of 2'-deoxycytidine-5'-monophosphate as substrate for DNA polymerization by HIV-1 reverse transcriptase" Bioorg. Med. Chem. (2009) 17(19):7008-7014.

International Search Report for application PCT/US2011/033592 dated Dec. 27, 2011.

\* cited by examiner

Sequences and Chemical Modifications

5'-Phosphate mimics, N1, Internal and 3'- Terminal Modifications of standard PTEN sequence e.g., P(Teos)UfsgUfscUfscUfsgGfsuCfscUfsusAfscsUfsus(Aeos)(Aeo)

5'-END DERIVATIVES

CROSS REFERENCED TO RELATED APPLICATIONS

This application is a U.S. National Phase filing under 35 U.S.C. §371 claiming priority to International Serial No. PCT/US2011/033592 filed Apr. 22, 2011, which claims priority to U.S. Provisional Application 61/326,960, filed Apr. 22, 2010, each of which is incorporated herein by reference in its entirety.

TECHNICAL FIELD

Provided herein are 5'-end modified nucleosides and oligonucleotides. The invention further provides methods of making and using the same.

BACKGROUND

Oligonucleotides and their analogs have been developed for various uses in molecular biology, including use as probes, primers, linkers, adapters, and gene fragments. In a number of these applications, the oligonucleotides specifically hybridize to a target nucleic acid.

In certain instances, chemical modifications have been introduced into oligonucleotides to increase their usefulness in diagnostics, as research reagents and as therapeutic entities. Such modifications include those designed for a variety of purposes, for example: to increase binding to a target nucleic acid (i.e., increase their melting temperature, $T_m$), to assist in identification of the oligonucleotide or an oligonucleotide-target complex, to increase cell penetration, to stabilize against nucleases and other enzymes that degrade or interfere with the structure or activity of the oligonucleotide, to provide a mode of disruption (a terminating event) once sequence-specifically bound to a target, and to improve the pharmacokinetic properties of the oligonucleotide.

SUMMARY

In one aspect, the present invention provides 5'-end caps of formula (1), (2), (3), (4), and (2A)-(4A). The 5'-end modified compounds could be single stranded siRNA, double stranded siRNA, micro RNA, antimicroRNA, aptamer or antisense oligonucleotide containing a motif selected from the modifications described herein and combinations of modifications thereof. The invention provides that the said modified 5'-end compound is one of the strands or constitutes both strands of a double-stranded siRNA. In one occurrence the modified oligonucleotide is the guide or antisense strand and in another occurrence the modified oligonucleotide is the sense or passenger strand of the double-stranded siRNA or both the strands of siRNA bear modified oligonucleotides. In certain embodiments, the present invention provides single-stranded oligomeric compounds that inhibit protein expression.

DETAILED DESCRIPTION

Figure 1:
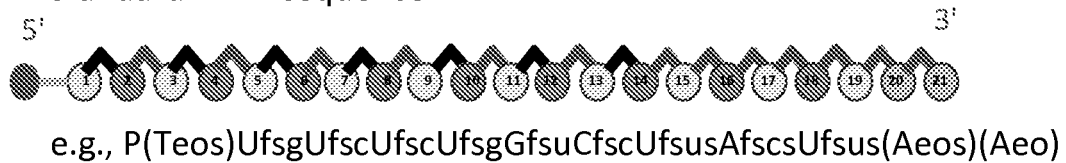
FIG. 1 is a schematic showing the oligonucleotide sequence design from modification of standard PTEN sequence and an exemplary sequence showing the 5'-end modification of the oligonucleotide with a phosphate mimic.

In one embodiment, the invention provides compounds of formula (1), or isomers thereof:

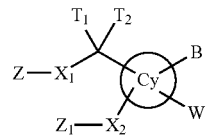

(1)

or isomers thereof, wherein

is a 4, 5, 6, 7 or 8 heterocyclic or cycloalkyl ring;

$T_1$ and $T_2$ are each independently H, OR", SR", $NQ_1Q_2$, substituted or unsubstituted aliphatic; alternatively, $T_1$ and $T_2$ can be taking together with the carbon they attached to form C=O, C=S, C=$NQ_1$; where $Q_1$ and $Q_2$ are each independently selected from H, OH, substituted or unsubstituted aliphatic, substituted or unsubstituted acyl, substituted or unsubstituted aryl, substituted or unsubstituted heteroaryl, substituted or unsubstituted heterocyclyl, and substituted or unsubstituted cycloalkyl and where R" is H, substituted or unsubstituted aliphatic, substituted or unsubstituted aryl, substituted or unsubstituted heteroaryl, substituted or unsubstituted heterocyclyl, and substituted or unsubstituted cycloalkyl;

$X_1$ is O, S, $NQ_1$, or $(CR_aR_b)_t$ wherein each $R_a$ and $R_b$ is, independently, H, F, $C_1$-$C_6$ haloalkyl, or $C_1$-$C_6$ alkyl; wherein t is 1 to 6;

$X_2$ is $CR_aR_b$, O, S, or $NQ_1$;

Z is selected from $OP(Z_{10})Y_{10}NQ_1Q_2$, $R_{10}$, $OR_{10}$, $COR_{10}$, $CO(CR_aR_b)_tCOR_{10}$, $CO_2R_{10}$, $NR_{20}R_{30}$, $CONR_{20}R_{30}$, $CON(H)NR_{20}R_{30}$, $ONR_{20}R_{30}$, $CON(H)N$=$CR_{40}R_{50}$, $N(R_{20})C($=$NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N$=$CR_{40}R_{50}$, $ON$=$CR_{40}R_{50}$, $SO_2R_{10}$, $SOR_{10}$, $SR_{10}$ and substituted or unsubstituted heterocyclic, where $R_{10}$ is independently hydrogen, aliphatic, substituted or unsubstituted aliphatic, aryl, heteroaryl, or heterocyclic; $R_{20}$, $R_{30}$, $R_{40}$ and $R_{50}$ are independently selected from is hydrogen, acyl, aliphatic or substituted aliphatic, aryl, heteroaryl, heterocyclic, $OR_{10}$, $COR_{10}$, $CO_2R_{10}$, $NQ_1Q_2$; $R_{20}$ and $R_{30}$ can be taken together to form a heterocyclic ring; wherein $Y_{10}$ and $Z_{10}$ are each independently O, S, alkyl, or $NQ_1Q_2$;

$Z_1$ is H, protecting group, reactive phosphorus group, or oligonucleotide;

B is selected from hydrogen, aliphatic, substituted aliphatic, natural nucleobase, modified nucleobase and universal base; and W is H, halogen, $OR_{10}$, $SR_{10}$, $NQ_1Q_2$, substituted or unsubstituted aliphatic, substituted or unsubstituted aryl, substituted or unsubstituted heteroaryl, substituted or unsubstituted cylcoalkyl, substituted or unsubstituted heterocyclyl; protecting group, reactive phosphorus group, or oligonucleotide.

In one embodiment, the invention provides compounds of formula (2), or isomers thereof:

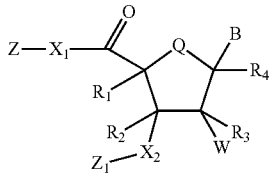

(2)

wherein Q is O, S, $NQ_1$, $CR_aR_b$;

$X_1$ is O, S, $NQ_1$, or $(CR_aR_b)_t$ wherein each $R_a$ and $R_b$ is, independently, H, F, $C_1$-$C_6$ haloalkyl, or $C_1$-$C_6$ alkyl; wherein t is 1 to 6;

$X_2$ is $CR_aR_b$, O, S, or $NQ_1$;

Z is selected from $OP(Z_{10})Y_{10}NQ_1Q_2$, $R_{10}$, $OR_{10}$, $COR_{10}$, $CO(CR_aR_b)_tCOR_{10}$, $CO_2R_{10}$, $NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$ and substituted or unsubstituted heterocyclic, where $R_{10}$ is independently hydrogen, aliphatic, substituted or unsubstituted aliphatic, aryl, heteroaryl, or heterocyclic; $R_{20}$, $R_{30}$, $R_{40}$ and $R_{50}$ are independently selected from is hydrogen, acyl, aliphatic or substituted aliphatic, aryl, heteroaryl, heterocyclic, $OR_{10}$, $COR_{10}$, $CO_2R_{10}$, $NQ_1Q_2$; $R_{20}$ and $R_{30}$ can be taken together to form a heterocyclic ring; wherein $Y_{10}$ and $Z_{10}$ are each independently O, S, alkyl, or $NQ_1Q_2$;

$Z_1$ is H, protecting group, reactive phosphorus group, or oligonucleotide;

B is selected from hydrogen, aliphatic, substituted aliphatic, natural nucleobase, modified nucleobase and universal base;

W is H, halogen, $OR_{10}$, $SR_{10}$, $NQ_1Q_2$, substituted or unsubstituted aliphatic, substituted or unsubstituted aryl, substituted or unsubstituted heteroaryl, substituted or unsubstituted cylcoalkyl, substituted or unsubstituted heterocyclyl; protecting group, reactive phosphorus group, or oligonucleotide; and $R_1$, $R_2$, $R_3$, and $R_4$ are each independently selected from H, halogen, OH, $C_1$-$C_6$ alkyl, $C_1$-$C_6$ haloalkyl; alternatively, two of $R_1$, $R_2$, $R_3$ and $R_4$ can be taken together to form a 5-8 membered ring, wherein the ring can optionally contain a heteroatom.

In one embodiment, the invention provides nucleosides of formula (3), or isomers thereof:

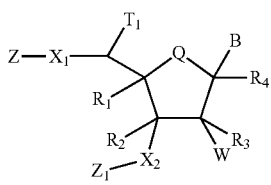

(3)

wherein $T_1$ is selected from OR", SR", $NQ_1$, $Q_2$, and substituted or unsubstituted aliphatic;

Q is O, S, $NQ_1$, $CR_aR_b$;

$X_1$ is O, S, $NQ_1$, or $(CR_aR_b)_t$ wherein each $R_a$ and $R_b$ is, independently, H, F, $C_1$-$C_6$ haloalkyl, or $C_1$-$C_6$ alkyl; wherein t is 1 to 6;

$X_2$ is $CR_aR_b$, O, S, or $NQ_1$;

Z is selected from $OP(Z_{10})Y_{10}NQ_1Q_2$, $R_{10}$, $OR_{10}$, $COR_{10}$, $CO(CR_aR_b)_tCOR_{10}$, $CO_2R_{10}$, $NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$ and substituted or unsubstituted heterocyclic, where $R_{10}$ is independently hydrogen, aliphatic, substituted or unsubstituted aliphatic, aryl, heteroaryl, or heterocyclic; $R_{20}$, $R_{30}$, $R_{40}$ and $R_{50}$ are independently selected from is hydrogen, acyl, aliphatic or substituted aliphatic, aryl, heteroaryl, heterocyclic, $OR_{10}$, $COR_{10}$, $CO_2R_{10}$, $NQ_1Q_2$; $R_{20}$ and $R_{30}$ can be taken together to form a heterocyclic ring; wherein $Y_{10}$ and $Z_{10}$ are each independently O, S, alkyl, or $NQ_1Q_2$;

$Z_1$ is H, protecting group, reactive phosphorus group, or oligonucleotide;

B is selected from hydrogen, aliphatic, substituted aliphatic, natural nucleobase, modified nucleobase and universal base;

W is H, halogen, $OR_{10}$, $SR_{10}$, $NQ_1Q_2$, substituted or unsubstituted aliphatic, substituted or unsubstituted aryl, substituted or unsubstituted heteroaryl, substituted or unsubstituted cylcoalkyl, substituted or unsubstituted heterocyclyl; protecting group, reactive phosphorus group, or oligonucleotide; and $R_1$, $R_2$, $R_3$, and $R_4$ are each independently selected from H, halogen, OH, $C_1$-$C_6$ alkyl, $C_1$-$C_6$ haloalkyl; alternatively, two of $R_1$, $R_2$, $R_3$ and $R_4$ can be taken together to form a 5-8 membered ring, wherein the ring can optionally contain a heteroatom.

In one embodiment, the invention provides nucleosides of formula (4), or isomers thereof:

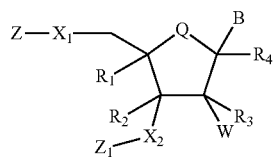

(4)

wherein Q is O, S, $NQ_1$, $CR_aR_b$;

$X_1$ is O, S, $NQ_1$, or $(CR_aR_b)_t$ wherein each $R_a$ and $R_b$ is, independently, H, F, $C_1$-$C_6$ haloalkyl, or $C_1$-$C_6$ alkyl; wherein t is 1 to 6;

$X_2$ is $CR_aR_b$, O, S, or $NQ_1$;

Z is selected from $OP(Z_{10})Y_{10}NQ_1Q_2$, $R_{10}$, $OR_{10}$, $COR_{10}$, $CO(CR_aR_b)_tCOR_{10}$, $CO_2R_{10}$, $NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$ and substituted or unsubstituted heterocyclic, where $R_{10}$ is independently hydrogen, aliphatic, substituted or unsubstituted aliphatic, aryl, heteroaryl, or heterocyclic; $R_{20}$, $R_{30}$, $R_{40}$ and $R_{50}$ are independently selected from is hydrogen, acyl, aliphatic or substituted aliphatic, aryl, heteroaryl, heterocyclic, $OR_{10}$, $COR_{10}$, $CO_2R_{10}$, $NQ_1Q_2$; $R_{20}$ and $R_{30}$ can be taken together to form a heterocyclic ring; wherein $Y_{10}$ and $Z_{10}$ are each independently O, S, alkyl, or $NQ_1Q_2$;

$Z_1$ is H, protecting group, reactive phosphorus group, or oligonucleotide;

B is selected from hydrogen, aliphatic, substituted aliphatic, natural nucleobase, modified nucleobase and universal base;

W is H, halogen, $OR_{10}$, $SR_{10}$, $NQ_1Q_2$, substituted or unsubstituted aliphatic, substituted or unsubstituted aryl, substituted or unsubstituted heteroaryl, substituted or unsubstituted cylcoalkyl, substituted or unsubstituted heterocyclyl; protecting group, reactive phosphorus group, or oligonucleotide; and $R_1$, $R_2$, $R_3$, and $R_4$ are each independently selected from H, halogen, OH, $C_1$-$C_6$ alkyl, $C_1$-$C_6$ haloalkyl; alternatively, two of $R_1$, $R_2$, $R_3$ and $R_4$ can be taken together to form a 5-8 membered ring, wherein the ring can optionally contain a heteroatom.

Alternatively, the embodiments of the invention also provide nucleosides of the following formulas (2A)-(4A), or isomers thereof.

In one embodiment, the invention provides nucleosides of formula (2A), or isomers thereof:

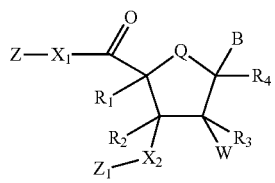

(2A)

wherein:

Q is O, S, $NQ_1$, or $CR_aR_b$;

$X_1$ is absent, O, S, $NQ_1$, or $(CR_aR_b)_t$;

$R_a$ and $R_b$ are each independently H, F, $C_1$-$C_6$ haloalkyl, or $C_1$-$C_6$ alkyl;

t is 1 to 6;

$X_2$ is absent, $CR_aR_b$, O, S, or $NQ_1$;

Z is selected from the group consisting of $OP(Z_{10})(Y_{10})NQ_1Q_2$, $R_{10}$, $OR_{10}$, $COR_{10}$, $CO(CR_aR_b)_tCOR_{10}$, $CO_2R_{10}$, $NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$, substituted or unsubstituted heterocyclic,

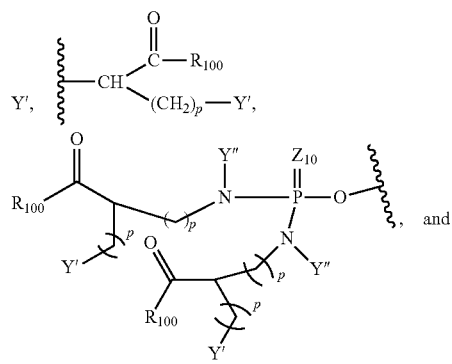

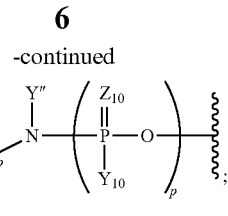

$R_{100}$ is selected from the group consisting of OH, SH, $NQ_1Q_2$, $(CH_2)_nCOR_{100}$, $(CH_2)_nNQ_1Q_2$, $(CH_2)_nOH$, $(CH_2)_nSH$, alkyl, alkoxy, aralkyl, aryl, heterocyclic, heteroaryl, cyclic alkyl, alkenyl, alkynyl, aralkenyl, and aralkynyl;

Y' and Y'' are each independently H, OH, $OR_{10}$, $(CH_2)_nOH$, SH, $(CH_2)_nSCH_3$, $(CH_2)_nSH$, $COR_{100}$, $(CH_2)_nCOR_{100}$, $(CH_2)_nCONQ_1Q_2$, $(CH_2)_nNQ_1Q_2$, $(CH_2)_nNHC(=NQ_1)NQ_2$, $(CH_2)_nCONQ_1Q_2$, $OP(Z_{10})(Y_{10})NQ_1Q_2$, $OP(Z_{10})(X_{10})Y_{10}$, linear or branched aliphatic, hydroxyl or alkoxy substituted aliphatic, aryl, arylalkyl, hydroxyl or alkoxy substituted aryl, hydroxyl or alkoxy substituted arylakyl, heteroaryl, heterocyclic, hydroxyl or alkoxy substituted heteroaryl, or hydroxyl or alkoxy substituted heterocyclic;

p is 0-10;

$R_{10}$ is independently hydrogen, substituted or unsubstituted aliphatic, hydroxyl or alkoxy substituted aliphatic, aryl, arylaliphatic, hydroxyl or alkoxy substituted aryl, hydroxyl or alkoxy substituted arylaliphatic, heteroaryl, heterocyclic, hydroxyl or alkoxy substituted heteroaryl, or hydroxyl or alkoxy substituted heterocyclic;

$R_{20}$, $R_{30}$, $R_{40}$ and $R_{50}$ are each independently selected from the group consisting of hydrogen, acyl, aliphatic or substituted aliphatic, aryl, heteroaryl, heterocyclic, $OR_{10}$, $COR_{10}$, $CO_2R_{10}$, and $NQ_1Q_2$; or $R_{20}$ and $R_{30}$ can be taken together to form a heterocyclic ring;

$Y_{10}$ and $Z_{10}$ are each independently O, S, alkyl, or $NQ_1Q_2$;

$Z_1$ is H, halogen, substituted or unsubstituted aliphatic, substituted or unsubstituted aryl, substituted or unsubstituted heteroaryl, substituted or unsubstituted cylcoalkyl, substituted or unsubstituted heterocyclyl, protecting group, reactive phosphorus group, or oligonucleotide;

B is selected from the group consisting of hydrogen, aliphatic, substituted aliphatic, natural nucleobase, modified nucleobase and universal base;

W is H, halogen, $OR_{10}$, $SR_{10}$, $NQ_1Q_2$, substituted or unsubstituted aliphatic, substituted or unsubstituted aryl, substituted or unsubstituted heteroaryl, substituted or unsubstituted cylcoalkyl, substituted or unsubstituted heterocyclyl, protecting group, reactive phosphorus group, or oligonucleotide;

$R_1$, $R_2$, $R_3$, and $R_4$ are each independently selected from the group consisting of H, halogen, OH, $C_1$-$C_6$ alkyl, and $C_1$-$C_6$ haloalkyl; or two of $R_1$, $R_2$, $R_3$ and $R_4$ can be taken together to form a 5-8 membered ring, wherein the ring can optionally contain a heteroatom; and $Q_1$ and $Q_2$ are each independently selected from the group consisting of H, OH, substituted or unsubstituted aliphatic, substituted or unsubstituted acyl, substituted or unsubstituted carboxyl, substituted or unsubstituted aryl, substituted or unsubstituted heteroaryl, substituted or unsubstituted heterocyclyl, and substituted or unsubstituted cycloalkyl.

In one embodiment, the invention provides nucleosides of formula (3A), or isomers thereof:

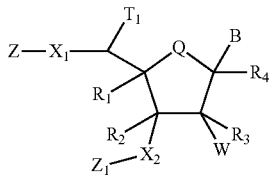

(3A)

wherein:

$T_1$ is selected from the group consisting of OR", SR", $NQ_1Q_2$, and substituted or unsubstituted aliphatic;

R' and R" are each independently H, substituted or unsubstituted aliphatic, substituted or unsubstituted aryl, substituted or unsubstituted heteroaryl, substituted or unsubstituted heterocyclyl, and substituted or unsubstituted cycloalkyl;

Q is O, S, $NQ_1$, or $CR_aR_b$;

$X_1$ is absent, O, S, $NQ_1$, or $(CR_aR_b)_t$;

$R_a$ and $R_b$ each are independently H, F, $C_1$-$C_6$ haloalkyl, or $C_1$-$C_6$ alkyl;

t is 1 to 6;

$X_2$ is absent, $CR_aR_b$, O, S, or $NQ_1$;

Z is selected from the group consisting of $OP(Z_{10})(Y_{10})NQ_1Q_2$, $R_{10}$, $OR_{10}$, $COR_{10}$, $CO(CR_aR_b)_tCOR_{10}$, $CO_2R_{10}$, $NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$, substituted or unsubstituted heterocyclic,

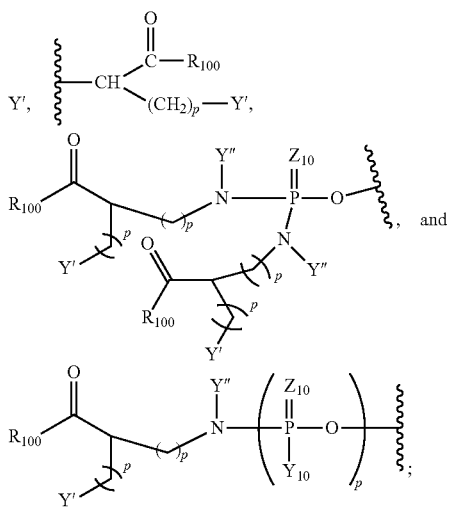

$R_{100}$ is selected from the group consisting of OH, SH, $NQ_1Q_2$, $(CH_2)_nCOR_{100}$, $(CH_2)_nNQ_1Q_2$, $(CH_2)_nOH$, $(CH_2)_nSH$, alkyl, alkoxy, aralkyl, aryl, heterocyclic, heteroaryl, cyclic alkyl, alkenyl, alkynyl, aralkenyl, and aralkynyl;

Y' and Y" are each independently H, OH, $OR_{100}$, $(CH_2)_nOH$, SH, $(CH_2)_nSCH_3$, $(CH_2)_nSH$, $COR_{100}$, $(CH_2)_nCOR_{100}$, $(CH_2)_nCONQ_1Q_2$, $(CH_2)_nNQ_1Q_2$, $(CH_2)_nNHC(=NQ_1)NQ_2$, $(CH_2)_nCONQ_1Q_2$, $OP(Z_{10})(Y_{10})NQ_1Q_2$, $OP(Z_{10})(X_{10})Y_{10}$, linear or branched aliphatic, hydroxyl or alkoxy substituted aliphatic, aryl, arylalkyl, hydroxyl or alkoxy substituted aryl, hydroxyl or alkoxy substituted arylakyl, heteroaryl, heterocyclic, hydroxyl or alkoxy substituted heteroaryl, or hydroxyl or alkoxy substituted heterocyclic;

p is 0-10;

$R_{10}$ is independently hydrogen, substituted or unsubstituted aliphatic, hydroxyl or alkoxy substituted aliphatic, aryl, arylaliphatic, hydroxyl or alkoxy substituted aryl, hydroxyl or alkoxy substituted arylaliphatic, heteroaryl, heterocyclic, hydroxyl or alkoxy substituted heteroaryl, or hydroxyl or alkoxy substituted heterocyclic;

$R_{20}$, $R_{30}$, $R_{40}$ and $R_{50}$ are each independently selected from the group consisting of hydrogen, acyl, aliphatic or substituted aliphatic, aryl, heteroaryl, heterocyclic, $OR_{10}$, $COR_{10}$, $CO_2R_{10}$, and $NQ_1Q_2$; or $R_{20}$ and $R_{30}$ can be taken together to form a heterocyclic ring;

$Y_{10}$ and $Z_{10}$ are each independently O, S, alkyl, or $NQ_1Q_2$;

$Z_1$ is H, halogen, substituted or unsubstituted aliphatic, substituted or unsubstituted aryl, substituted or unsubstituted heteroaryl, substituted or unsubstituted cylcoalkyl, substituted or unsubstituted heterocyclyl, protecting group, reactive phosphorus group, or oligonucleotide;

B is selected from the group consisting of hydrogen, aliphatic, substituted aliphatic, natural nucleobase, modified nucleobase and universal base;

W is H, halogen, $OR_{10}$, $SR_{10}$, $NQ_1Q_2$, substituted or unsubstituted aliphatic, substituted or unsubstituted aryl, substituted or unsubstituted heteroaryl, substituted or unsubstituted cylcoalkyl, substituted or unsubstituted heterocyclyl, protecting group, reactive phosphorus group, or oligonucleotide; and $R_1$, $R_2$, $R_3$, and $R_4$ are each independently selected from the group consisting of H, halogen, OH, $C_1$-$C_6$ alkyl, and $C_1$-$C_6$ haloalkyl; or two of $R_1$, $R_2$, $R_3$ and $R_4$ can be taken together to form a 5-8 membered ring, wherein the ring can optionally contain a heteroatom; and $Q_1$ and $Q_2$ are each independently selected from the group consisting of H, OH, substituted or unsubstituted aliphatic, substituted or unsubstituted acyl, substituted or unsubstituted carboxyl, substituted or unsubstituted aryl, substituted or unsubstituted heteroaryl, substituted or unsubstituted heterocyclyl, and substituted or unsubstituted cycloalkyl.

In one embodiment, the invention provides nucleosides of formula (4A), or isomers thereof:

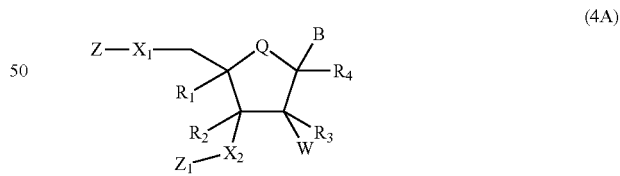

(4A)

wherein:

Q is O, S, $NQ_1$, or $CR_aR_b$;

$X_1$ is absent, O, S, $NQ_1$, or $(CR_aR_b)_t$;

$R_a$ and $R_b$ are each independently H, F, $C_1$-$C_6$ haloalkyl, or $C_1$-$C_6$ alkyl;

t is 1 to 6;

$X_2$ is absent, $CR_aR_b$, O, S, or $NQ_1$;

Z is selected from the group consisting of $OP(Z_{10})(Y_{10})NQ_1Q_2$, $R_{10}$, $OR_{10}$, $COR_{10}$, $CO(CR_aR_b)_tCOR_{10}$, $CO_2R_{10}$, $NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)$ $NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$, substituted or unsubstituted heterocyclic,

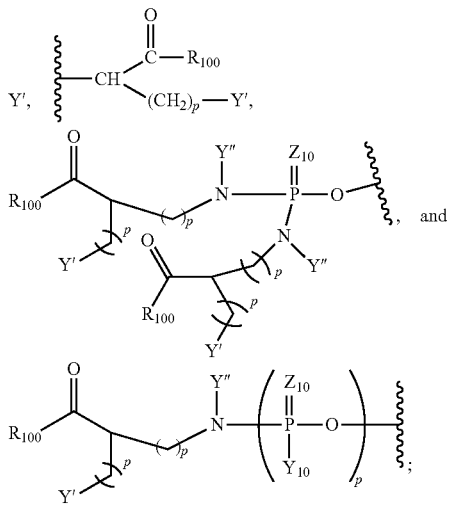

$R_{100}$ is selected from the group consisting of OH, SH, $NQ_1Q_2$, $(CH_2)_nCOR_{100}$, $(CH_2)_nNQ_1Q_2$, $(CH_2)_nOH$, $(CH_2)_nSH$, alkyl, alkoxy, aralkyl, aryl, heterocyclic, heteroaryl, cyclic alkyl, alkenyl, alkynyl, aralkenyl, and aralkynyl;

Y' and Y" are each independently H, OH, $OR_{100}$, $(CH_2)_nOH$, SH, $(CH_2)_nSCH_3$, $(CH_2)_nSH$, $COR_{100}$, $(CH_2)_nCOR_{100}$, $(CH_2)_nCONQ_1Q_2$, $(CH_2)_nNQ_1Q_2$, $(CH_2)_nNHC(=NQ_1)NQ_2$, $(CH_2)_nCONQ_1Q_2$, $OP(Z_{10})(Y_{10})NQ_1Q_2$, $OP(Z_{10})(X_{10})Y_{10}$, linear or branched aliphatic, hydroxyl or alkoxy substituted aliphatic, aryl, arylalkyl, hydroxyl or alkoxy substituted aryl, hydroxyl or alkoxy substituted arylakyl, heteroaryl, heterocyclic, hydroxyl or alkoxy substituted heteroaryl, or hydroxyl or alkoxy substituted heterocyclic;

p is 0-10;

$R_{10}$ is independently hydrogen, substituted or unsubstituted aliphatic, hydroxyl or alkoxy substituted aliphatic, aryl, arylaliphatic, hydroxyl or alkoxy substituted aryl, hydroxyl or alkoxy substituted arylaliphatic, heteroaryl, heterocyclic, hydroxyl or alkoxy substituted heteroaryl, or hydroxyl or alkoxy substituted heterocyclic;

$R_{20}$, $R_{30}$, $R_{40}$ and $R_{50}$ are each independently selected from the group consisting of hydrogen, acyl, aliphatic or substituted aliphatic, aryl, heteroaryl, heterocyclic, $OR_{10}$, $COR_{10}$, $CO_2R_{10}$, $NQ_1Q_2$; or $R_{20}$ and $R_{30}$ can be taken together to form a heterocyclic ring;

$Y_{10}$ and $Z_{10}$ are each independently O, S, alkyl, or $NQ_1Q_2$;

$Z_1$ is H, halogen, substituted or unsubstituted aliphatic, substituted or unsubstituted aryl, substituted or unsubstituted heteroaryl, substituted or unsubstituted cylcoalkyl, substituted or unsubstituted heterocyclyl, protecting group, reactive phosphorus group, or oligonucleotide;

B is selected from the group consisting of hydrogen, aliphatic, substituted aliphatic, natural nucleobase, modified nucleobase and universal base;

W is H, halogen, $OR_{10}$, $SR_{10}$, $NQ_1Q_2$, substituted or unsubstituted aliphatic, substituted or unsubstituted aryl, substituted or unsubstituted heteroaryl, substituted or unsubstituted cylcoalkyl, substituted or unsubstituted heterocyclyl, protecting group, reactive phosphorus group, or oligonucleotide; and $R_1$, $R_2$, $R_3$, and $R_4$ are each independently selected from the group consisting of H, halogen, OH, $C_1$-$C_6$ alkyl, $C_1$-$C_6$ haloalkyl; or two of $R_1$, $R_2$, $R_3$ and $R_4$ can be taken together to form a 5-8 membered ring, wherein the ring can optionally contain a heteroatom; and $Q_1$ and $Q_2$ are each independently selected from the group consisting of H, OH, substituted or unsubstituted aliphatic, substituted or unsubstituted acyl, substituted or unsubstituted carboxyl, substituted or unsubstituted aryl, substituted or unsubstituted heteroaryl, substituted or unsubstituted heterocyclyl, and substituted or unsubstituted cycloalkyl.

In some embodiments, in each of the above formulas (2)-(4) and (2A)-(4A), Z can be selected from natural and un-natural a-amino acids with D and L stereochemistry, peptides, substituted amines, carboxylic acids, amino acid, hydroxy acids, oligo and polyamines.

Representative subgenuses of the invention includes:

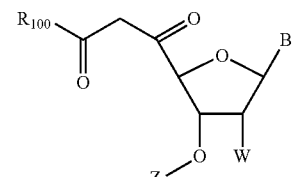

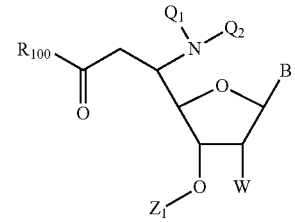

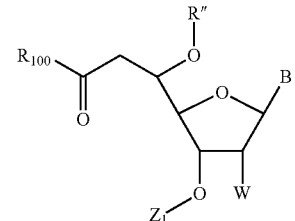

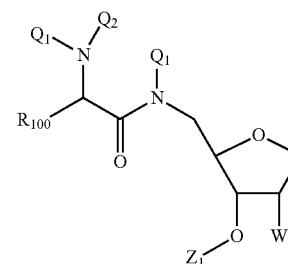

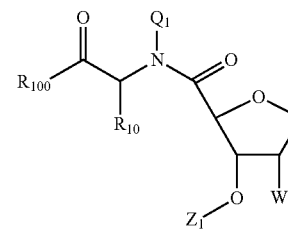

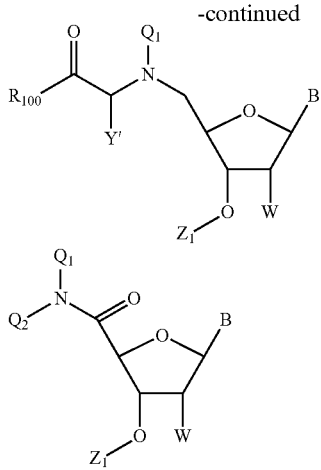

5'-End modified nucleosides, nucleotides and oligonucleotides

Single and double stranded siRNAs, microRNA, antimir, antagomir, supermir, antisense, aptamer Classes of 5'-end modifications Natural and un-natural a-amino acids with D and L stereochemistry Peptides Substituted amines, carboxylic acids, amino acid, hydroxy acids Oligo and Polyamines $Z_1$=Oligonucleotide, phosphoramidite B and W are as previously defined.

Alternatively, the embodiments of the invention also provide the subgenus of compounds represented by the following formulas, and isomers thereof:

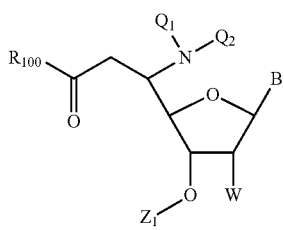
(3-a)

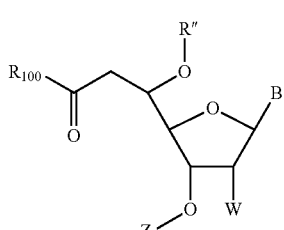
(3-b)

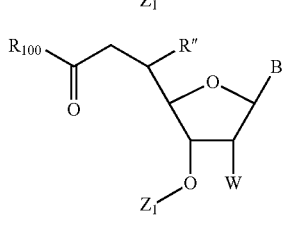
(3-c)

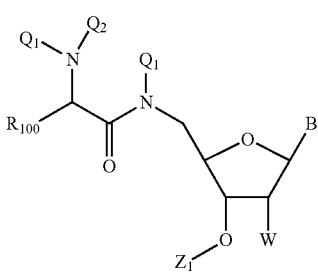
(4-a)

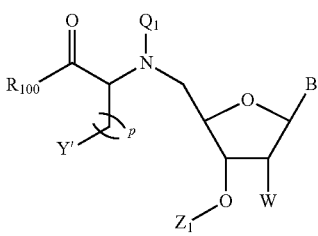
(4-b)

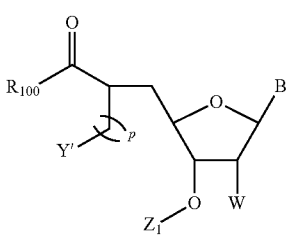
(4-c)

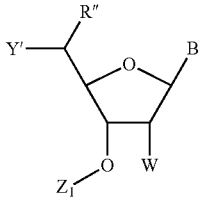
(4-d)

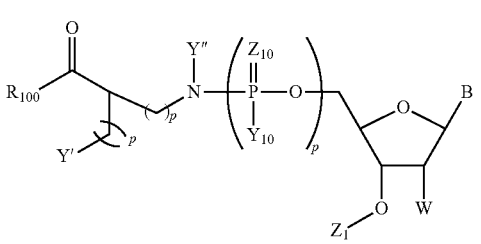
(4-e)

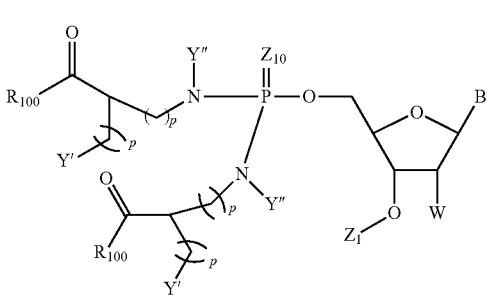
(4-f)

-continued

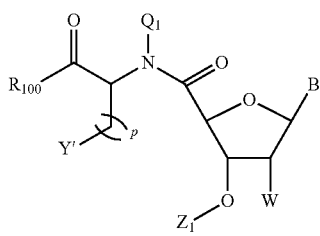
(2-a)

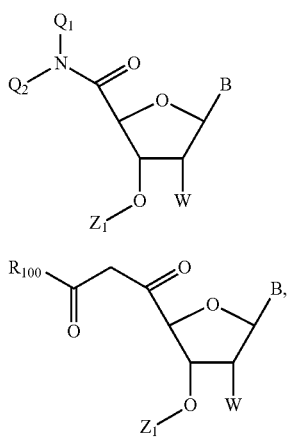
(2-b)

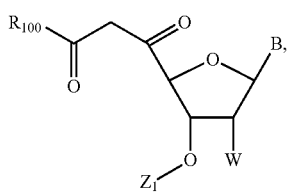
(2-c)

wherein:

R'' is H, substituted or unsubstituted aliphatic, substituted or unsubstituted aryl, substituted or unsubstituted heteroaryl, substituted or unsubstituted heterocyclyl, and substituted or unsubstituted cycloalkyl;

$Y_{10}$ and $Z_{10}$ are each independently absent, O, S, alkyl, hydroxyl, alkoxy, cyanoalkyl, cyanoalkoxy, $NQ_1$ or $NQ_1Q_2$;

$Z_1$ is H, halogen, substituted or unsubstituted aliphatic, substituted or unsubstituted aryl, substituted or unsubstituted heteroaryl, substituted or unsubstituted cylcoalkyl, substituted or unsubstituted heterocyclyl, protecting group, reactive phosphorus group, or oligonucleotide;

B is selected from the group consisting of hydrogen, aliphatic, substituted aliphatic, natural nucleobase, modified nucleobase and universal base;

W is H, halogen, $OR_{10}$, $SR_{10}$, $NQ_1Q_2$, substituted or unsubstituted aliphatic, substituted or unsubstituted aryl, substituted or unsubstituted heteroaryl, substituted or unsubstituted cylcoalkyl, substituted or unsubstituted heterocyclyl, protecting group, reactive phosphorus group, or oligonucleotide;

$Q_1$ and $Q_2$ are each independently selected from the group consisting of H, OH, substituted or unsubstituted aliphatic, substituted or unsubstituted acyl, substituted or unsubstituted carboxyl, substituted or unsubstituted aryl, substituted or unsubstituted heteroaryl, substituted or unsubstituted heterocyclyl, and substituted or unsubstituted cycloalkyl;

$R_{100}$ are each independently selected from the group consisting of OH, SH, $NQ_1Q_2$, $(CH_2)_nCOR_{100}$, $(CH_2)_nNQ_1Q_2$, $(CH_2)_nOH$, $(CH_2)_nSH$, alkyl, alkoxy, aralkyl, aryl, heterocyclic, heteroaryl, cyclic alkyl, alkenyl, alkynyl, aralkenyl, and aralkynyl;

Y' and Y'' are each independently H, OH, $OR_{100}$, $(CH_2)_nOH$, SH, $(CH_2)_nSCH_3$, $(CH_2)_nSH$, $COR_{100}$, $(CH_2)_nCOR_{100}$, $(CH_2)_nCONQ_1Q_2$, $(CH_2)_nNQ_1Q_2$, $(CH_2)_nNHC(=NQ_1)NQ_2$, $(CH_2)_nCONQ_1Q_2$, $OP(Z_{10})(Y_{10})NQ_1Q_2$, $OP(Z_{10})(X_{10})Y_{10}$, linear or branched aliphatic, hydroxyl or alkoxy substituted aliphatic, aryl, arylalkyl, hydroxyl or alkoxy substituted aryl, hydroxyl or alkoxy substituted arylakyl, heteroaryl, heterocyclic, hydroxyl or alkoxy substituted heteroaryl, or hydroxyl or alkoxy substituted heterocyclic;

n is 1-10; and p is 0-10.

Exemplary compounds can be represented by formulas, and isomers thereof, shown as below:

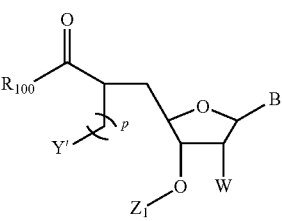
(4-c)

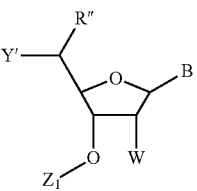
(4-d)

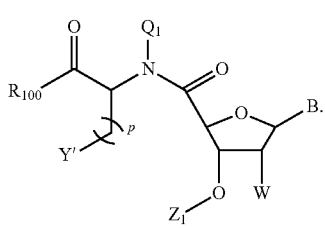
(2-a)

5'-Phosphoramidate Prodrug

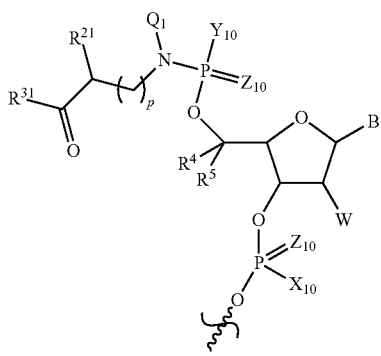

-continued

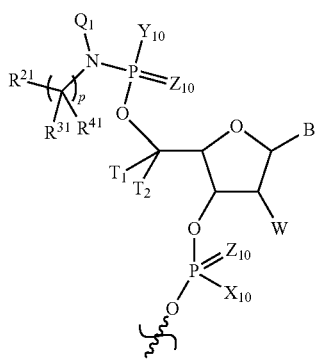

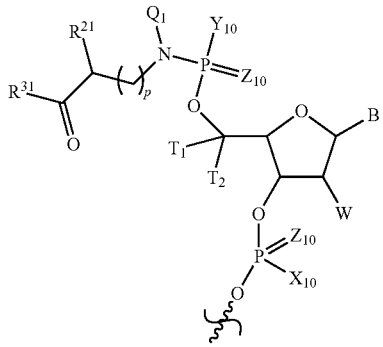
1-a

X10 and Y10 each independently is O, S, NQ$_1$, NQ$_1$Q$_2$;

B is A, C, G, U, T and other natural or non-natural bases

Configuration independently at C1', C2' or C3' position is α or β or combination thereof.

The asymmetric position(s) is (are) independently R, S, racemic or combination thereof p is 0-6;

$R^{21}$ to $R^{51}$ is selected from OH, SH, NQ$_1$Q$_2$, (CH$_2$)$_n$COR$^3$, (CH$_2$)$_n$N(R')(R"), (CH$_2$)$_n$OH; (CH$_2$)$_n$ SH, alkyl, aralkyl, aryl, heterocyclic, cyclic alkyl, alkenyl, alkynyl, aralkenyl, aralkynyl, where n is 1-10;

B is A, C, G, U, T and other natural or non-natural bases.

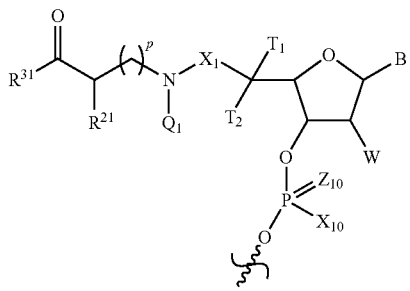

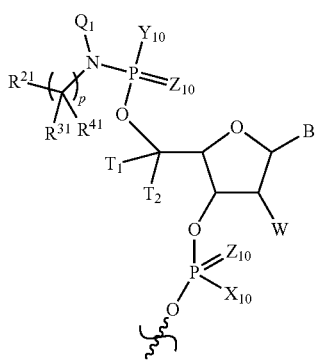
1-b

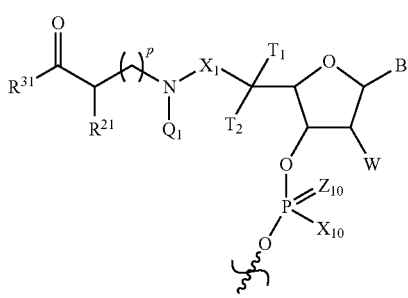
1-c

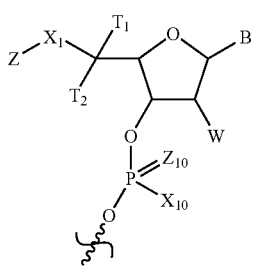

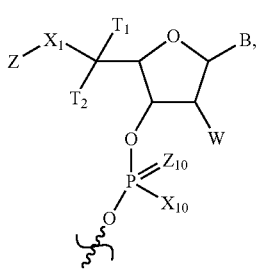
1-d where X$_1$ is absent, C(O), —P(O)(YM)-O—, —C(O)(CH$_2$)$_n$C(O)—, (CR$_a$R$_b$)$_n$, wherein n is 1-10.

In one embodiment, Z is selected from natural and un-natural a-amino acids with D and L stereochemistry, peptides, substituted amines, carboxylic acids, amino acid, hydroxy acids, oligo and polyamines.

Alternatively, the embodiments of the invention also provide the compounds represented by the following formulas, and isomers thereof:

wherein:

T$_1$ and T$_2$ are each independently selected from the group consisting of H, OR", SR", NQ$_1$Q$_2$, and substituted or unsubstituted aliphatic;

R' and R" are each independently H, substituted or unsubstituted aliphatic, substituted or unsubstituted aryl, substituted or unsubstituted heteroaryl, substituted or unsubstituted heterocyclyl, and substituted or unsubstituted cycloalkyl;

X$_1$ is absent, O, S, NQ$_1$, or (CR$_a$R$_b$)$_t$;

R$_a$ and R$_b$ each are independently H, F, C$_1$-C$_6$ haloalkyl, or C$_1$-C$_6$ alkyl;

t is 1 to 6;

Z is selected from the group consisting of OP(Z$_{10}$)(Y$_{10}$) NQ$_1$Q$_2$, R$_{10}$, OR$_{10}$, COR$_{10}$, CO(CR$_a$R$_b$)$_t$COR$_{10}$, CO$_2$R$_{10}$, $NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$, substituted or unsubstituted heterocyclic,

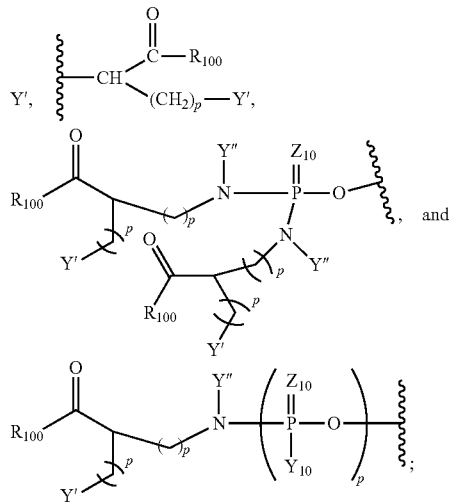

$R_{100}$ is selected from the group consisting of OH, SH, $NQ_1Q_2$, $(CH_2)_nCOR_{100}$, $(CH_2)_nNQ_1Q_2$, $(CH_2)_nOH$, $(CH_2)_nSH$, alkyl, alkoxy, aralkyl, aryl, heterocyclic, heteroaryl, cyclic alkyl, alkenyl, alkynyl, aralkenyl, and aralkynyl;

Y' and Y" are each independently H, OH, $OR_{100}$, $(CH_2)_nOH$, SH, $(CH_2)_nSCH_3$, $(CH_2)_nSH$, $COR_{100}$, $(CH_2)_nCOR_{100}$, $(CH_2)_nCONQ_1Q_2$, $(CH_2)_nNQ_1Q_2$, $(CH_2)_nNHC(=NQ_1)NQ_2$, $(CH_2)_nCONQ_1Q_2$, $OP(Z_{10})(Y_{10})NQ_1Q_2$, $OP(Z_{10})(X_{10})Y_{10}$, linear or branched aliphatic, hydroxyl or alkoxy substituted aliphatic, aryl, arylalkyl, hydroxyl or alkoxy substituted aryl, hydroxyl or alkoxy substituted arylakyl, heteroaryl, heterocyclic, hydroxyl or alkoxy substituted heteroaryl, or hydroxyl or alkoxy substituted heterocyclic;

$R_{10}$ is independently hydrogen, substituted or unsubstituted aliphatic, hydroxyl or alkoxy substituted aliphatic, aryl, arylaliphatic, hydroxyl or alkoxy substituted aryl, hydroxyl or alkoxy substituted arylaliphatic, heteroaryl, heterocyclic, hydroxyl or alkoxy substituted heteroaryl, or hydroxyl or alkoxy substituted heterocyclic;

$R_{20}$, $R_{30}$, $R_{40}$ and $R_{50}$ are each independently selected from the group consisting of hydrogen, acyl, aliphatic or substituted aliphatic, aryl, heteroaryl, heterocyclic, $OR_{10}$, $COR_{10}$, $CO_2R_{10}$, and $NQ_1Q_2$; or $R_{20}$ and $R_{30}$ can be taken together to form a heterocyclic ring;

$X_{10}$, $Y_{10}$ and $Z_{10}$ are each independently absent, O, S, alkyl, hydroxyl, alkoxy, cyanoalkyl, cyanoalkoxy, $NQ_1$ or $NQ_1Q_2$;

B is selected from the group consisting of hydrogen, aliphatic, substituted aliphatic, natural nucleobase, modified nucleobase and universal base;

W is H, halogen, $OR_{10}$, $SR_{10}$, $NQ_1Q_2$, substituted or unsubstituted aliphatic, substituted or unsubstituted aryl, substituted or unsubstituted heteroaryl, substituted or unsubstituted cylcoalkyl, substituted or unsubstituted heterocyclyl, protecting group, reactive phosphorus group, or oligonucleotide;

$Q_1$ and $Q_2$ are each independently selected from the group consisting of H, OH, substituted or unsubstituted aliphatic, substituted or unsubstituted acyl, substituted or unsubstituted carboxyl, substituted or unsubstituted aryl, substituted or unsubstituted heteroaryl, substituted or unsubstituted heterocyclyl, and substituted or unsubstituted cycloalkyl;

$R_{21}$, $R_{31}$ and $R_{41}$ are each independently selected from the group consisting of OH, SH, $NQ_1Q_2$, $(CH_2)_nCOR_{31}$, $(CH_2)_nNQ_1Q_2$, $(CH_2)_nOH$, $(CH_2)_nSH$, alkyl, alkoxy, aralkyl, aryl, heterocyclic, cyclic alkyl, alkenyl, alkynyl, aralkenyl, and aralkynyl;

n is 1-10; and
p is 0-10.

In some embodiments, Z of the above formula can be selected from natural and un-natural a-amino acids with D and L stereochemistry, peptides, substituted amines, carboxylic acids, amino acid, hydroxy acids, oligo and polyamines.

In some embodiments, in each of the above formulas (2A)-(4A), (1-a)-(1-d), (2-a)-(2-c), (3-a)-(3-c), and (4-a)-(4-f), $T_1$, $T_2$, R' and R" can be each independently H, alkyl, or alkoxy.

In some embodiments, in each of the above formulas (2A)-(4A), (1-a)-(1-d), (2-a)-(2-c), (3-a)-(3-c), and (4-a)-(4-f), Y' and Y" can be OH, $OR_{100}$, $(CH_2)_nOH$, SH, $(CH_2)_nSCH_3$, $(CH_2)_nSH$, $COR_{100}$, $(CH_2)_nCOR_{100}$, $(CH_2)_nCONQ_1Q_2$, $(CH_2)_nNQ_1Q_2$, $(CH_2)_nNHC(=NQ_1)NQ_2$, $(CH_2)_nCONQ_1Q_2$, $OP(Z_{10})(Y_{10})NQ_1Q_2$, $OP(Z_{10})(X_{10})Y_{10}$, linear or branched alkyl, aryl, hydroxyl or alkoxy substituted aryl, heteroaryl, or heterocyclic. In some embodiments, Y' and Y" can be independently for each occurrence Y' is $(CH_2)_nOH$, $(CH_2)_nSCH_3$, $(CH_2)_nSH$, $COR_{100}$, $(CH_2)_nCOR_{100}$, $(CH_2)_nNQ_1Q_2$, $OP(Z_{10})(Y_{10})NQ_1Q_2$, $OP(Z_{10})(X_{10})Y_{10}$, linear or branched alkyl, aryl, heteroaryl, or heterocyclic.

In some embodiments, in each of the above formulas (2A)-(4A), (1-a)-(1-d), (2-a)-(2-c), (3-a)-(3-c), and (4-a)-(4-f), n can be 1-4.

In some embodiments, in each of the above formulas (2A)-(4A), (1-a)-(1-d), (2-a)-(2-c), (3-a)-(3-c), and (4-a)-(4-f), p can be 0-6.

In some embodiments, in each of the above formulas (2A)-(4A), (1-a)-(1-d), (2-a)-(2-c), (3-a)-(3-c), and (4-a)-(4-f), $R_{100}$ can be OH or alkoxy.

In some embodiments, in each of the above formulas (2A)-(4A), (1-a)-(1-d), (2-a)-(2-c), (3-a)-(3-c), and (4-a)-(4-f), W can be H, OH, alkoxy, alkoxy substituted alkoxy, protecting group, reactive phosphorus group, or oligonucleotide.

In some embodiments, in each of the above formulas (2A)-(4A), (1-a)-(1-d), (2-a)-(2-c), (3-a)-(3-c), and (4-a)-(4-f), $Z_1$ can be H, OH, alkoxy, alkoxy substituted alkoxy, protecting group, reactive phosphorus group or oligonucleotide.

In some embodiments, the protecting group is a hydroxyl protecting group selected from the group consisting of acetyl, benzyl, t-butyldimethylsilyl, t-butyldiphenylsilyl, trityl, monomethoxytrityl, and dimethoxytrityl.

In some embodiments, the reactive phosphorus group can be selected from the group consisting of phosphoramidite, H-phosphonate, alkyl-phosphonate, and phosphate triester.

In some embodiments, in each of the above formulas (2A)-(4A), (1-a)-(1-d), (2-a)-(2-c), (3-a)-(3-c), and (4-a)-(4-f), $Z_1$ is a phosphoramidite.

In some embodiments, in each of the above formulas (2A)-(4A), (1-a)-(1-d), (2-a)-(2-c), (3-a)-(3-c), and (4-a)-(4-f), $Z_1$ is an oligonucleotide.

In some embodiments of the invention, compounds of each of the above formulas can be used to prepare oligonucleotides. For example, the compounds of each of the above formulas can be used to prepare double-stranded oligonucleotides, such as double-stranded siRNAs, or single-stranded oligonucleotides, such as single-stranded siRNAs. The compounds of each of the above formulas can be used to prepare hairpins, antisenses, antagomirs, microRNAs, pre-microRNAs, antimirs, ribozymes or aptamers.

In this respect, one or more of the compounds can be contained in one or more positions of the oligonucleotide, for instance, at internal positions, 5'-end terminal, 3'-end terminal, or combinations thereof. In one embodiment, the compound is present at least once at the 5'-end terminal position of the oligonucleotide.

The oligonucleotides containing the compound of any of the above formulas can also be used in a method of inhibiting the expression of a target gene in a cell. Such method comprises contacting the cell with the oligonucleotide comprising the compound of any of the above formulas.

Alternatively, the compounds themselves may be part of an oligonucleotide composition, where $Z_1$ or W in the formulas is an oligonucleotide. The oligonucleotide compounds of each of the above formulas can be double-stranded oligonucleotides, such as double-stranded siRNAs, or single-stranded oligonucleotides, such as single-stranded siRNAs. The oligonucleotide compounds of each of the above formulas can also be hairpins, antisenses, antagomirs, microRNAs, pre-microRNAs, antimirs, ribozymes or aptamers.

The oligonucleotides compounds of each of the above formulas can also be used in a method of inhibiting the expression of a target gene in a cell. Such method comprises contacting the cell with the oligonucleotide compounds of any of the above formulas.

In one embodiment, the oligonucleotides comprises further comprise: (a) 1-20 first-type regions, each first-type region independently comprising 1-20 contiguous nucleosides wherein each nucleoside of each first-type region comprises a first-type modification; (b) 0-20 second-type regions, each second-type region independently comprising 1-20 contiguous nucleosides wherein each nucleoside of each second-type region comprises a second-type modification; and (c) 0-20 third-type regions, each third-type region independently comprising 1-20 contiguous nucleosides wherein each nucleoside of each third-type region comprises a third-type modification; wherein the first-type modification, the second-type modification, and the third-type modification are each independently selected from 2'-F, 2'-OCH$_3$, 2'-O(CH$_2$)2OCH$_3$, BNA, F-HNA, 2'-H and 2'-OH;

In one embodiment, one of $Z_1$ or W is a 4,4'-dimethoxytrityl protected hydroxyl group and the other $Z_1$ or W is a reactive phosphorus group comprising a diisopropylcyanoethoxy phosphoramidite group. In a preferred embodiment, W is 4,4'-dimethoxytrityl protected hydroxyl group and $Z_1$ comprises a diisopropylcyanoethoxy phosphoramidite group.

In one example, B is uracil, 5-methyluracil, 5-methylcytosine, 5-thiazolo-uracil, 5-thiazolo-cytosine, adenine, guanine or 2,6-diaminopurine.

In one embodiment, each hydroxyl protecting group is, independently, acetyl, t-butyl, t-butoxymethyl, methoxymethyl, tetrahydropyranyl, 1-ethoxyethyl, 1-(2-chloroethoxy) ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl, dimethoxytrityl, trimethoxytrityl, 9-phenylxanthine-9-yl (Pixyl) or 9-(p-methoxyphenyl)xanthine-9-yl (MOX). In a preferred embodiment, each of the hydroxyl protecting groups is, independently, acetyl, benzyl, t-butyldimethylsilyl, t-butyldiphenylsilyl or 4,4'-dimethoxytrityl.

In one embodiment, the oligonucleotides of the invention comprise internucleoside linkages selected from phosphorus and non-phosphorus containing internucleoside. In one example, the phosphorus containing internucleoside includes, but not limited to, phosphodiester, phosphorothioates, chiral phosphorothioates, phosphorodithioates, phosphotriesters, aminoalkylphosphotriesters, methyl and other alkyl phospho-nates including 3'-alkylene phosphonates, 5'-alkylene phosphonates and chiral phosphonates, phosphinates, phosphoramidates including 3'-amino phosphoramidate and amino alkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most inter-nucleotide linkage i.e. a single inverted nucleoside residue which may be abasic (the nucleobase is missing or has a hydroxyl group in place thereof). Various salts, mixed salts and free acid forms are also included. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

In one embodiment, oligonucleotides of the invention comprise one or more internucleoside linkages that don't contain a phosphorus atom. Such oligonucleotides include, but are not limited to, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts. Representative U.S. patents that teach the preparation of the above non-phosphorus containing internucleoside linking group include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In one embodiment, oligonucleotides of the invention comprise one or more neutral internucleoside linkage that are non-ionic. Neutral internucleoside linkages include but are not limited to phosphotriesters, methylphosphonates, MMI (3'-CH$_2$—N(CH$_3$)—O-5'), amide-3 (3'-CH$_2$—C (=O)—N(H)-5'), amide-4 (3'-CH$_2$—N(H)—C(=O)-5'), formacetal (3'-O-CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook Eds. ACS Symposium Series 580; Chapters 3 and 4, (pp. 40-65)). Further neutral internucleoside linkages include nonionic linkages comprising mixed N, O, S and CH2 component parts.

In one embodiment, non-phosphodiester backbone linkage is selected from a group consisting of phosphorothioate, phosphorodithioate, alkyl-phosphonate and phosphoramidate backbone linkage.

In one aspect, the present invention provides an oligonucleotide comprising at least one modified nucleoside of formula (2), (4), (6), (8) or (10), optionally in combination with natural base and derivatives thereof, or modified nucleobase. The modified base includes high affinity modification such as G-clamp and analogs, phenoxazines and analogs; bi- and tricyclic non-natural nucleoside bases. The invention further provides said modified oligonucleotides with 3', 5' or both 3' and 5' terminal phosphate or phosphate mimics. The phosphate or phosphate mimics includes α- and/or β-configuration with respect to the sugar ring or combinations thereof. The phosphate or phosphate mimics include but not limited to: natural phosphate, -phosphorothioate, phosphorodithioate, borano phosphate, borano thiophosphate, phosphonate, halogen substituted phosphonates, phosphoramidates, phosphodiester, phosphotriester, thiophosphodiester, thiophosphotriester, diphosphates and triphosphates. The invention also provides sugar modified purine dimers at 3' and 5'-terminals (i.e. 5'/3'-GG, AA, AG, GA, GI, IA etc.), wherein the purine bases are natural or chemically modified preferably at 2, 6 and 7 positions of the base or combinations thereof. The invention also provides nucleoside at position 1 (5'-end) with 2' and/or 4'-sugar modified natural and modified nucleobase, purine or pyrimidine nucleobase mimics or combinations thereof. The modified oligonucleotides could be single stranded siRNA, double stranded siRNA, micro RNA, antimicroRNA, aptamer or antisense oligonucleotide containing a motif selected from the modifications described herein and combinations of modifications thereof. The invention provides that the said modified oligonucleotide is one of the strands or constitute for both strands of a double strands siRNA. In one occurrence the modified oligonucleotide is the guide or antisense strand and in another occurrence the modified oligonucleotide is sense or passenger strand of the double stranded siRNA or both the strands of ds siRNA bear modified oligonucleotides.

In one embodiment, the oligonucleotide comprises at least one ligand conjugate.

In one embodiment, the oligonucleotide comprises two or more ligand conjugates.

In one embodiment, the oligonucleotide is a double-stranded oligonucleotide.

In one embodiment, only one strand comprises the modified nucleoside.

In one embodiment, both strands comprise the modified nucleoside.

In one embodiment, the modified nucleoside is the same in the two strands.

In one embodiment, the modified nucleoside is different in the two strands.

In one embodiment, the oligonucleotide is a single-stranded oligonucleotide.

In one embodiment, the oligonucleotide has a hairpin structure.

In one embodiment, the oligonucleotide is an RNAi agent, an antisense, an antagomir, a microRNA, a pre-microRNA, an antimir, a ribozyme or an aptamer oligonucleotide.

In one embodiment, the RNAi agent is double stranded and only the sense strand comprises the modified nucleoside.

In one embodiment, the RNAi agent is double stranded and only the antisense strand comprises the modified nucleoside.

In one embodiment, the RNAi agent is double-stranded and both the sense and the antisense strands comprise at least one modified nucleoside.

In one embodiment, the modified nucleoside is the same in both the sense and the antisense strands.

In one embodiment, the sense and the antisense strands comprise different modified nucleosides.

The nucleoside and oligonucleotides described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion. In general, the term "oligomeric compound" refers to a contiguous sequence of linked monomelic subunits. In general each linked monomelic subunits is directly or indirectly attached to a heterocyclic base moiety but abasic sites are also possible. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having a plurality of non-naturally occurring nucleoside mimetics and or nucleosides having sugar surrogate groups.

Oligonucleotides

In the context of this invention, the term "oligonucleotide" refers to a polymer or oligomer of linked nucleosides or nucleotides. In certain embodiments, oligonucleotides comprise naturally occurring nucleosides and internucleoside linkages. In certain embodiments, oligonucleotides comprise one or more modification or substitution to a base, sugar and/or internucleoside linkage. Such modified or substituted oligonucleotides are often preferred over native forms because of properties such as, for example, enhanced cellular uptake and increased stability in the presence of nucleases.

The oligonucleotides used herein can be single-stranded, double-stranded, or hairpin. Double-stranded oligonucleotides comprise two separate strands hybridized together. The two strands of a double-stranded oligonucleotide may have the same or different lengths and may be fully complementary or may be partially complementary, provided that they have sufficient complementarity to remain hybridized under physiological conditions. Examples of double-stranded DNA include but are not limited to structural genes, genes including control and termination regions, and self-replicating systems such as viral or plasmid DNA. Examples of double-stranded RNA include siRNA and other RNA interference reagents. Single-stranded oligonucleotides comprise a single strand that is not bound to its complements and that lacks sufficient self-complementarity to form a double-stranded region under physiological conditions. Single-stranded nucleic acids include, e.g., antisense oligonucleotides, microRNAs, aptamers, antagomirs, triplex-forming oligonucleotides and single-stranded RNAi agents. Hairpin oligonucleotides comprise sufficient complementarity within the base sequence to allow self-hybridization under physiological conditions. Oligonucleotides of the present invention may be of various lengths. In particular embodiments, oligonucleotides may range from about 10 to 100 nucleotides in length. In various related embodiments, oligonucleotides, single-stranded, double-stranded, and triple-stranded, may range in length from about 10 to about 50 nucleotides, from about 20 to about 50 nucleotides, from about 15 to about 30 nucleotides, from about 20 to about 30 nucleotides in length.

The oligonucleotides of the invention may comprise any oligonucleotide modification described herein and below. In certain instances, it may be desirable to modify one or both strands of a double-stranded oligonucleotide. In some cases, the two strands will include different modifications. Multiple different modifications can be included on each of the strands. The modifications on a given strand may differ from each other, and may also differ from the various modifications on other strands. For example, one strand may have a modification, e.g., a modification described herein, and a different strand may have a different modification, e.g., a different modification described herein. In other cases, one strand may have two or more different modifications, and the another strand may include a modification that differs from the at least two modifications on the other strand.

In one embodiment, oligonucleotides of the invention comprises 5' phosphorothioate or 5'-phosphorodithioate, nucleotides 1 and 2 having cationic modifications via C-5 position of pyrimidines, 2-Position of Purines, N2-G, G-clamp, 8-position of purines, 6-position of purines, internal nucleotides having a 2'-F sugar with base modifications (Pseudouridine, G-clamp, phenoxazine, pyridopyrimidines, gem2'-Me-up/2'-F-down), 3'-end with two purines with novel 2'-substituted MOE analogs, 5'-end nucleotides with novel 2'-substituted MOE analogs, 5'-end having a 3'-F and a 2'-5'-linkage, 4'-substituted nucleoside at the nucleotide 1 at 5'-end and the substituent is cationic, alkyl, alkoxyalkyl, thioether and the like, 4'-substitution at the 3'-end of the strand, and combinations thereof.

Double-Stranded Oligonucleotides

In one embodiment, the invention provides double-stranded oligonucleotide for inhibiting the expression of the target gene (alone or in combination with a second oligonucleotide for inhibiting the expression of a second target gene) in a cell or mammal, wherein the double-stranded oligonucleotide comprises an antisense strand comprising a region of complementarity which is complementary to at least a part of an mRNA formed in the expression of the target gene, and wherein the region of complementarity is less than 30 nucleotides in length, generally 19-24 nucleotides in length, and wherein said double-stranded oligonucleotide, upon contact with a cell expressing said target gene, inhibits the expression of said target gene. The double-stranded oligonucleotide comprises two oligonucleotides that are sufficiently complementary to hybridize to form a duplex structure. Generally, the duplex structure is between 15 and 30, more generally between 18 and 25, yet more generally between 19 and 24, and most generally between 19 and 21 base pairs in length. In one embodiment, longer double-stranded oligonucleotides of between 25 and 30 base pairs in length are preferred. In one embodiment, shorter double-stranded oligonucleotides of between 10 and 15 base pairs in length are preferred. In another embodiment, the double-stranded oligonucleotide is at least 21 nucleotides long and includes a sense oligonucleotide and an antisense oligonucleotide, wherein the antisense oligonucleotide is 25 or fewer nucleotides in length, and the duplex region of the double-stranded oligonucleotide is 18-25 nucleotides in length, e.g., 19-24 nucleotides in length.

Similarly, the region of complementarity to the target sequence is between 15 and 30, more generally between 18 and 25, yet more generally between 19 and 24, and most generally between 19 and 21 nucleotides in length. The double-stranded oligonucleotide of the invention may further comprise one or more single-stranded nucleotide overhang(s).

In a preferred embodiment, the target gene is a human target gene. In one embodiment, the target gene is selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, p73 gene, p21(WAF1/CIP1) gene, p27(KIP1) gene, PPM1D gene, RAS gene, caveolin I gene, MIB I gene, MTAI gene, M68 gene, mutations in tumor suppressor genes, p53 tumor suppressor gene, and combinations thereof.

The skilled person is well aware that double-stranded oligonucleotides comprising a duplex structure of between 20 and 23, but specifically 21, base pairs have been hailed as particularly effective in inducing RNA interference (Elbashir et al., EMBO 2001, 20:6877-6888). However, others have found that shorter or longer double-stranded oligonucleotides can be effective as well. In the embodiments described above the dsRNAs of the invention can comprise at least one strand of a length of minimally 21 nt. It can be reasonably expected that shorter double-stranded oligonucleotides comprising a known sequence minus only a few nucleotides on one or both ends may be similarly effective as compared to the dsRNAs of the lengths described above. Hence, double-stranded oligonucleotides comprising a partial sequence of at least 15, 16, 17, 18, 19, 20, or more contiguous nucleotides, and differing in their ability to inhibit the expression of the target gene by not more than 5, 10, 15, 20, 25, or 30% inhibition from a double-stranded oligonucleotide comprising the full sequence, are contemplated by the invention. Further double-stranded oligonucleotides that cleave within the target sequence can readily be made using the target gene sequence and the target sequence provided.

Double-stranded and single-stranded oligonucleotides that are effective in inducing RNA interference are also referred to as siRNA, RNAi agent and/or iRNA agent. These RNA interference inducing oligonucleotides associate with a cytoplasmic multi-protein complex known as RNAi-induced silencing complex (RISC). In many embodiments, single-stranded and double stranded RNAi agents are sufficiently long that they can be cleaved by an endogenous molecule, e.g. by Dicer, to produce smaller oligonucleotides that can enter the RISC machinery and participate in RISC mediated cleavage of a target sequence, e.g. a target mRNA.

The present invention further includes RNAi agents that target within the sequence targeted by one of the agents of the present invention. As used herein a second RNAi agent is said to target within the sequence of a first RNAi agent if the second RNAi agent cleaves the message anywhere within the mRNA that is complementary to the antisense strand of the first RNAi agent. Such a second agent will generally consist of at least 15 contiguous nucleotides coupled to additional nucleotide sequences taken from the region contiguous to the selected sequence in the target gene.

The double-stranded oligonucleotides of the invention can contain one or more mismatches to the target sequence. In a preferred embodiment, the double-stranded oligonucleotide of the invention contains no more than 3 mismatches. If the antisense strand of the double-stranded oligonucleotide contains mismatches to a target sequence, it is preferable that the area of mismatch not be located in the center of the region of complementarity. If the antisense strand of the double-stranded oligonucleotide contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide double-stranded oligonucleotide strand which is complementary to a region of the target gene, the double-stranded oligonucleotide generally does not contain any mismatch within the central 13 nucleotides. The methods described within the invention can be used to determine whether a double-stranded oligonucleotide containing a mismatch to a target sequence is effective in inhibiting the expression of the target gene. Consideration of the efficacy of double-stranded oligonucleotides with mismatches in inhibiting expression of the target gene is important, especially if the particular region of complementarity in the target gene is known to have polymorphic sequence variation within the population.

In certain embodiments, the sense-strand comprises a mismatch to the antisense strand. In some embodiments, the mismatch is at the 5 nucleotides from the 3'-end, for example 5, 4, 3, 2, or 1 nucleotide from the end of the region of complementarity. In some embodiments, the mismatch is located in the target cleavage site region. In one embodiment, the sense strand comprises no more than 1, 2, 3, 4 or 5 mismatches to the antisense strand. In preferred embodiments, the sense strand comprises no more than 3 mismatches to the antisense strand.

In one embodiment, the sense strand comprises a nucleobase modification, e.g. an optionally substituted natural or non-natural nucleobase, a universal nucleobase, in the target cleavage site region.

The "target cleavage site" herein means the internucleoside linkage in the target nucleic acid, e.g. target mRNA, or the sense strand that is cleaved by the RISC mechanism by utilizing the iRNA agent. And the "target cleavage site region" comprises at least one or at least two nucleotides on both side of the cleavage site. For the sense strand, the target cleavage site is the internucleoside linkage in the sense strand that would get cleaved if the sense strand itself was the target to be cleaved by the RNAi mechanism. The target cleavage site can be determined using methods known in the art, for example the 5'-RACE assay as detailed in Soutschek et al., *Nature* (2004) 432, 173-178. As is well understood in the art, the cleavage site region for a conical double stranded RNAi agent comprising two 21-nucleotides long strands (wherein the strands form a double stranded region of 19 consecutive basepairs having 2-nucleotide single stranded overhangs at the 3'-ends), the cleavage site region corresponds to positions 9-12 from the 5'-end of the sense strand.

In one embodiment, at least one end of the double-stranded oligonucleotide has a single-stranded nucleotide overhang of 1 to 4, generally 1 or 2 nucleotides. In one embodiment, the single-stranded overhang has the sequence 5'-GCNN-3', wherein N is independently for each occurrence, A, G, C, U, dT, dU or absent. Double-stranded oligonucleotides having at least one nucleotide overhang have unexpectedly superior inhibitory properties than their blunt-ended counterparts. Moreover, the present inventors have discovered that the presence of only one nucleotide overhang strengthens the interference activity of the double-stranded oligonucleotide, without affecting its overall stability. Double-stranded oligonucleotide having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The double-stranded oligonucleotide may also have a blunt end, generally located at the 5'-end of the antisense strand. Generally, the antisense strand of the double-stranded oligonucleotide has a nucleotide overhang at the 3'-end, and the 5'-end is blunt.

In one embodiment, the antisense strand of the double-stranded oligonucleotide has 1-10 nucleotides overhangs each at the 3' end and the 5' end over the sense strand. In one embodiment, the sense strand of the double-stranded oligonucleotide has 1-10 nucleotides overhangs each at the 3' end and the 5' end over the antisense strand.

The double-stranded oligonucleotides of the invention may comprise any oligonucleotide modification described herein and below. In certain instances, it may be desirable to modify one or both strands of a double-stranded oligonucleotide. In some cases, the two strands will include different modifications. Multiple different modifications can be included on each of the strands. The modifications on a given strand may differ from each other, and may also differ from the various modifications on other strands. For example, one strand may have a modification, e.g., a modification described herein, and a different strand may have a different modification, e.g., a different modification described herein. In other cases, one strand may have two or more different modifications, and the another strand may include a modification that differs from the at least two modifications on the other strand.

In one embodiment, the double-stranded oligonucleotide is chemically modified to enhance stability. In one preferred embodiment, one or more of the nucleotides in the overhang is replaced with a nucleoside thiophosphate.

The present invention also includes double-stranded oligonucleotide compounds which are chimeric compounds.

"Chimeric" double-stranded oligonucleotide compounds or "chimeras," in the context of this invention, are double-stranded oligonucleotide compounds, contain two or more chemically distinct regions, each made up of at least one monomer unit, i.e., a nucleotide in the case of a double-stranded oligonucleotide compound. These double-stranded oligonucleotides typically contain at least one region wherein the double-stranded oligonucleotide is modified so as to confer upon the double-stranded oligonucleotide increased resistance to nuclease degradation, increased cellular uptake, and/or increased binding affinity for the target nucleic acid. An additional region of the double-stranded oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of dsRNA inhibition of gene expression.

The present invention also includes hairpin oligonucleotides. In certain embodiments, the self-hybridizing regions of a hairpin oligonucleotides are linked together by a polynucleotide linker such as $(dT)_n$; wherein n is 4-10. The two complementary regions can also be linked together by a non-nucleosidic linker, e.g. a linker described herein. It will be appreciated by one of skill in the art that any oligonucleotide chemical modifications or variations describe herein can be used in the polynucleotide linker.

Hairpin oligonucleotides typically have a duplex region equal to or at least 17, 18, 19, 29, 21, 22, 23, 24, or 25 nucleotide pairs. The duplex region may be equal to or less than 200, 100, or 50, in length. In one embodiment, ranges for the duplex region are 15-30, 17 to 23, 19 to 23, and 19 to 21 nucleotides pairs in length. The hairpin may have a single strand overhang or terminal unpaired region, in some embodiments at the 3', and in one embodiment on the antisense side of the hairpin. In one embodiment, the overhangs are 2-3 nucleotides in length.

The RNAi agents of the invention can target more than one RNA region. For example, an RNAi agent can include a first and second sequence that are sufficiently complementary to each other to hybridize. The first sequence can be complementary to a first target RNA region and the second sequence can be complementary to a second target RNA region. The first and second sequences of the RNAi agent can be on different RNA strands, and the mismatch between the first and second sequences can be less than 50%, 40%, 30%, 20%, 10%, 5%, or 1%. The first and second sequences of the RNAi agent can be on the same RNA strand, and in a related embodiment more than 50%, 60%, 70%, 80%, 90%, 95%, or 1% of the RNAi agent can be in bimolecular form. The first and second sequences of the RNAi agent can be fully complementary to each other.

The first target RNA region can be encoded by a first gene and the second target RNA region can encoded by a second gene, or the first and second target RNA regions can be different regions of an RNA from a single gene. The first and second sequences can differ by at least 1 nucleotide.

The first and second target RNA regions can be on transcripts encoded by first and second sequence variants, e.g., first and second alleles, of a gene. The sequence variants can be mutations, or polymorphisms, for example. The first target RNA region can include a nucleotide substitution, insertion, or deletion relative to the second target RNA region, or the second target RNA region can a mutant or variant of the first target region.

The first and second target RNA regions can comprise viral or human RNA regions. The first and second target RNA regions can also be on variant transcripts of an oncogene or include different mutations of a tumor suppressor gene transcript. In addition, the first and second target RNA regions can correspond to hot-spots for genetic variation.

The double stranded oligonucleotides can be optimized for RNA interference by increasing the propensity of the duplex to disassociate or melt (decreasing the free energy of duplex association), in the region of the 5' end of the antisense strand This can be accomplished, e.g., by the inclusion of modifications or modified nucleosides which increase the propensity of the duplex to disassociate or melt in the region of the 5' end of the antisense strand. It can also be accomplished by inclusion of modifications or modified nucleosides or attachment of a ligand that increases the propensity of the duplex to disassociate of melt in the region of the 5' end of the antisense strand. While not wishing to be bound by theory, the effect may be due to promoting the effect of an enzyme such as helicase, for example, promoting the effect of the enzyme in the proximity of the 5' end of the antisense strand.

Modifications which increase the tendency of the 5' end of the antisense strand in the duplex to dissociate can be used alone or in combination with other modifications described herein, e.g., with modifications which decrease the tendency of the 3' end of the antisense in the duplex to dissociate. Likewise, modifications which decrease the tendency of the 3' end of the antisense in the duplex to dissociate can be used alone or in combination with other modifications described herein, e.g., with modifications which increase the tendency of the 5' end of the antisense in the duplex to dissociate.

Nucleic acid base pairs can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; I:C is preferred over G:C (I=inosine); mismatches, e.g., non-canonical or other than canonical pairings are preferred over canonical (A:T, A:U, G:C) pairings; pairings which include a universal base are preferred over canonical pairings.

It is preferred that pairings which decrease the propensity to form a duplex are used at 1 or more of the positions in the duplex at the 5' end of the antisense strand. The terminal pair (the most 5' pair in terms of the antisense strand), and the subsequent 4 base pairing positions (going in the 3' direction in terms of the antisense strand) in the duplex are preferred for placement of modifications to decrease the propensity to form a duplex. More preferred are placements in the terminal most pair and the subsequent 3, 2, or 1 base pairings. It is preferred that at least 1, and more preferably 2, 3, 4, or 5 of the base pairs from the 5'-end of antisense strand in the duplex be chosen independently from the group of: A:U, G:U, I:C, mismatched pairs, e.g., non-canonical or other than canonical pairings or pairings which include a universal base. In a preferred embodiment at least one, at least 2, or at least 3 base-pairs include a universal base.

Modifications or changes which promote dissociation are preferably made in the sense strand, though in some embodiments, such modifications/changes will be made in the antisense strand.

Nucleic acid base pairs can also be ranked on the basis of their propensity to promote stability and inhibit dissociation or melting (e.g., on the free energy of association or dissociation of a particular pairing, the simplest approach is to examine the pairs on an individual pair basis, though next neighbor or similar analysis can also be used). In terms of promoting duplex stability: G:C is preferred over A:U, Watson-Crick matches (A:T, A:U, G:C) are preferred over non-canonical or other than canonical pairings, analogs that increase stability are preferred over Watson-Crick matches (A:T, A:U, G:C), e.g. 2-amino-A:U is preferred over A:U, 2-thio U or 5 Me-thio-U:A, are preferred over U:A, G-clamp (an analog of C having 4 hydrogen bonds):G is preferred over C:G, guanadinium-G-clamp:G is preferred over C:G, psuedo uridine:A, is preferred over U:A, sugar modifications, e.g., 2' modifications, e.g., 2'F, ENA, or LNA, which enhance binding are preferred over non-modified moieties and can be present on one or both strands to enhance stability of the duplex.

It is preferred that pairings which increase the propensity to form a duplex are used at 1 or more of the positions in the duplex at the 3' end of the antisense strand. The terminal pair (the most 3' pair in terms of the antisense strand), and the subsequent 4 base pairing positions (going in the 5' direction in terms of the antisense strand) in the duplex are preferred for placement of modifications to decrease the propensity to form a duplex. More preferred are placements in the terminal most pair and the subsequent 3, 2, or 1 base pairings. It is preferred that at least 1, and more preferably 2, 3, 4, or 5 of the pairs of the recited regions be chosen independently from the group of: G:C, a pair having an analog that increases stability over Watson-Crick matches (A:T, A:U, G:C), 2-amino-A:U, 2-thio U or 5 Me-thio-U:A, G-clamp (an analog of C having 4 hydrogen bonds):G, guanadinium-G-clamp:G, psuedo uridine:A, a pair in which one or both subunits has a sugar modification, e.g., a 2' modification, e.g., 2'F, ENA, or LNA, which enhance binding. In some embodiments, at least one, at least, at least 2, or at least 3, of the base pairs promote duplex stability.

In a preferred embodiment the at least one, at least 2, or at least 3, of the base pairs are a pair in which one or both subunits has a sugar modification, e.g., a 2' modification, e.g., 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH$_2$-(4'-C) (LNA) and 2'-O—CH$_2$CH$_2$-(4'-C) (ENA), which enhances binding.

G-clamps and guanidinium G-clamps are discussed in the following references: Holmes and Gait, "The Synthesis of 2'-O-Methyl G-Clamp Containing Oligonucleotides and Their Inhibition of the HIV-1 Tat-TAR Interaction," Nucleosides, Nucleotides & Nucleic Acids, 22:1259-1262, 2003; Holmes et al., "Steric inhibition of human immunodeficiency virus type-1 Tat-dependent trans-activation in vitro and in cells by oligonucleotides containing 2'-O-methyl G-clamp ribonucleoside analogues," Nucleic Acids Research, 31:2759-2768, 2003; Wilds, et al., "Structural basis for recognition of guanosine by a synthetic tricyclic cytosine analogue: Guanidinium G-clamp," Helvetica Chimica Acta, 86:966-978, 2003; Rajeev, et al., "High-Affinity Peptide Nucleic Acid Oligomers Containing Tricyclic Cytosine Analogues," Organic Letters, 4:4395-4398, 2002; Ausin, et al., "Synthesis of Amino- and Guanidino-G-Clamp PNA Monomers," Organic Letters, 4:4073-4075, 2002; Maier et al., "Nuclease resistance of oligonucleotides containing the tricyclic cytosine analogues phenoxazine and 9-(2-aminoethoxy)-phenoxazine ("G-clamp") and origins of their nuclease resistance properties," Biochemistry, 41:1323-7, 2002; Flanagan, et al., "A cytosine analog that confers enhanced potency to antisense oligonucleotides," Proceedings Of The National Academy Of Sciences Of The United States Of America, 96:3513-8, 1999.

As is discussed above, an oligonucleotide can be modified to both decrease the stability of the antisense 5' end of the duplex and increase the stability of the antisense 3' end of the duplex. This can be effected by combining one or more of the stability decreasing modifications in the antisense 5' end of the duplex with one or more of the stability increasing modifications in the antisense 3' end of the duplex.

Single-Stranded Oligonucleotides

In certain embodiments, single-stranded oligonucleotides of the present invention have a nucleobase sequence that is substantially complementary to that of a target nucleic acid. Certain such target nucleic acids encode a gene expression product, e.g., a pre-mRNA, mRNA, miRNA, or pre-miRNA. In certain embodiments, the region of complementarity is less than 30 nucleotides in length, and at least 15 nucleotides in length. Generally, the single stranded oligonucleotides are 10 to 25 nucleotides in length (e.g., 11, 12, 13, 14, 15, 16, 18, 19, 20, 21, 22, 23, or 24 nucleotides in length). In one embodiment the strand is 25-30 nucleotides. Single strands having less than 100% complementarity to the target mRNA, RNA or DNA are also embraced by the present invention. These single-stranded oligonucleotides are also referred to as antisense, antagomir and antimir oligonucleotides.

The single-stranded oligonucleotide can hybridize to a complementary RNA, and prevent access of the translation machinery to the target RNA transcript, thereby preventing protein synthesis. The single-stranded oligonucleotide can also hybridize to a complementary RNA and the RNA target can be subsequently cleaved by an enzyme such as RNase H. Degradation of the target RNA prevents translation.

Single-stranded oligonucleotides, including those described and/or identified as single stranded siRNAs, microRNAs or mirs which may be used as targets or may serve as a template for the design of oligonucleotides of the invention are taught in, for example, Esau, et al. US Publication #20050261218 (U.S. Ser. No. 10/909,125) entitled "Oligonucleotides and compositions for use in modulation small non-coding RNAs" the entire contents of which is incorporated herein by reference. It will be appreciated by one of skill in the art that any oligonucleotide chemical modifications or variations describe herein also apply to single stranded oligonucleotides.

MicroRNAs (miRNAs or mirs) are a highly conserved class of small RNA molecules that are transcribed from DNA in the genomes of plants and animals, but are not translated into protein. Pre-microRNAs are processed into miRNAs. Processed microRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

The number of miRNA sequences identified to date is large and growing, illustrative examples of which can be found, for example, in: "*miRBase: microRNA sequences, targets and gene nomenclature*" Griffiths-Jones S, Grocock R J, van Dongen S, Bateman A, Enright A J. NAR, 2006, 34, Database Issue, D140-D144; *"The microRNA Registry"* Griffiths-Jones S, NAR, 2004, 32, Database Issue, D109-

D111; and also on the worldwide web at http://microrna-.dot.sanger.dot.ac.dot.uk/sequences/.

Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate backbone and, for example, a cholesterol-moiety at 3'-end. Antagomirs may be used to efficiently silence endogenous miRNAs by forming duplexes comprising the antagomir and endogenous miRNA, thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein in its entirety. Antagomir RNAs may be synthesized using standard solid phase oligonucleotide synthesis protocols. See U.S. patent application Ser. Nos. 11/502,158 and 11/657,341 (the disclosure of each of which are incorporated herein by reference).

An antagomir can include ligand-conjugated monomer subunits and monomers for oligonucleotide synthesis. Exemplary monomers are described in U.S. application Ser. No. 10/916,185, filed on Aug. 10, 2004. An antagomir can have a ZXY structure, such as is described in PCT Application No. PCT/US2004/07070 filed on Mar. 8, 2004. An antagomir can be complexed with an amphipathic moiety. Exemplary amphipathic moieties for use with oligonucleotide agents are described in PCT Application No. PCT/US2004/07070, filed on Mar. 8, 2004.

Single stranded siRNAs (ss siRNAs) are known and are described in US publication US 2006/0166910 and hereby incorporated by herein by its entirety. Preferably, the single-stranded RNA molecule has a length from 15-29 nucleotides. The RNA-strand may have a 3' hydroxyl group. In some cases, however, it may be preferable to modify the 3' end to make it resistant against 3' to 5' exonucleases. Tolerated 3'-modifications are for example terminal 2'-deoxy nucleotides, 3' phosphate, 2',3'-cyclic phosphate, C3 (or C6, C7, C12) amino linker, thiol linkers, carboxyl linkers, non-nucleotidic spacers (C3, C6, C9, C12, abasic, triethylene glycol, hexaethylene glycol), biotin, fluoresceine, etc. Single stranded siRNAs of the invention include at least one of the following motifs: 5' phosphorothioate or 5'-phosphorodithioate, nucleotides 1 and 2 having cationic modifications via C-5 position of pyrimidines, 2-Position of Purines, N2-G, G-clamp, 8-position of purines, 6-position of purines, internal nucleotides having a 2'-F sugar with base modifications (Pseudouridine, G-clamp, phenoxazine, pyridopyrimidines, gem2'-Me-up/2'-F-down), 3'-end with two purines with novel 2'-substituted MOE analogs, 5'-end nucleotides with novel 2'-substituted MOE analogs, 5'-end having a 3'-F and a 2'-5'-linkage, 4'-substituted nucleoside at the nucleotide 1 at 5'-end and the substituent is cationic, alkyl, alkoxyalkyl, thioether and the like, 4'-substitution at the 3'-end of the strand, and combinations thereof.

Ribozymes are oligonucleotides having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). At least six basic varieties of naturally-occurring enzymatic RNAs are known presently. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Methods of producing a ribozyme targeted to any target sequence are known in the art. Ribozymes may be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein.

Aptamers are nucleic acid or peptide molecules that bind to a particular molecule of interest with high affinity and specificity (Tuerk and Gold, Science 249:505 (1990); Ellington and Szostak, Nature 346:818 (1990)). DNA or RNA aptamers have been successfully produced which bind many different entities from large proteins to small organic molecules. See Eaton, Curr. Opin. Chem. Biol. 1:10-16 (1997), Famulok, Curr. Opin. Struct. Biol. 9:324-9 (1999), and Hermann and Patel, Science 287:820-5 (2000). Aptamers may be RNA or DNA based. Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. The aptamer may be prepared by any known method, including synthetic, recombinant, and purification methods, and may be used alone or in combination with other aptamers specific for the same target. Further, as described more fully herein, the term "aptamer" specifically includes "secondary aptamers" containing a consensus sequence derived from comparing two or more known aptamers to a given target.

Immunostimulatory Oligonucleotides

Nucleic acids of the present invention may be immunostimulatory, including immunostimulatory oligonucleotides (single- or double-stranded) capable of inducing an immune response when administered to a subject, which may be a mammal or other patient. The immune response may be an innate or an adaptive immune response. The immune system is divided into a more innate immune system, and acquired adaptive immune system of vertebrates, the latter of which is further divided into humoral cellular components. In particular embodiments, the immune response may be mucosal.

Immunostimulatory nucleic acids are considered to be non-sequence specific when it is not required that they specifically bind to and reduce the expression of a target polynucleotide in order to provoke an immune response. Thus, certain immunostimulatory nucleic acids may comprise a sequence corresponding to a region of a naturally occurring gene or mRNA, but they may still be considered non-sequence specific immunostimulatory nucleic acids.

In one embodiment, the immunostimulatory nucleic acid or oligonucleotide comprises at least one CpG dinucleotide. The oligonucleotide or CpG dinucleotide may be unmethylated or methylated. In another embodiment, the immunostimulatory nucleic acid comprises at least one CpG dinucleotide having a methylated cytosine. In one embodiment, the nucleic acid comprises a single CpG dinucleotide, wherein the cytosine in said CpG dinucleotide is methylated. Methods of immune stimulation using single stranded oligonucleotides and immune stimulatory oligonucleotides.

The immunostimulatory nucleic acid or oligonucleotide comprises capable of inducing an anti-viral or an antibacterial response, in particular, the induction of type I IFN, IL-18 and/or IL-1β by modulating RIG-I.

Other Oligonucleotides

Because transcription factors recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to upregulate genes that are suppressed by the binding of a transcription factor. Examples of the utilization of decoy oligonucleotides may be found in Mann et al., J. Clin. Invest., 2000, 106: 1071-1075, which is expressly incorporated by reference herein, in its entirety.

U1 adaptor inhibit polyA sites and are bifunctional oligonucleotides with a target domain complementary to a site in the target gene's terminal exon and a 'U1 domain' that binds to the U1 smaller nuclear RNA component of the U1 snRNP (Goraczniak, et al., 2008, Nature Biotechnology, 27(3), 257-263, which is expressly incorporated by reference herein, in its entirety). U1 snRNP is a ribonucleoprotein complex that functions primarily to direct early steps in spliceosome formation by binding to the pre-mRNA exon-intron boundary (Brown and Simpson, 1998, Annu Rev Plant Physiol Plant MoI Biol 49:77-95). Nucleotides 2-11 of the 5' end of U1 snRNA base pair bind with the 5'ss of the pre mRNA. In one embodiment, oligonucleotides of the invention are U1 adaptors. In one embodiment, the U1 adaptor can be administered in combination with at least one other iRNA agent.

Oligonucleotide Modifications

Unmodified oligonucleotides may be less than optimal in some applications, e.g., unmodified oligonucleotides can be prone to degradation by e.g., cellular nucleases. Nucleases can hydrolyze nucleic acid phosphodiester bonds. However, chemical modifications to one or more of the above oligonucleotide components can confer improved properties, and, e.g., can render oligonucleotides more stable to nucleases.

Modified nucleic acids and nucleotide surrogates can include one or more of:

(i) alteration, e.g., replacement, of one or both of the non-linking phosphate oxygens and/or of one or more of the linking phosphate oxygens in the phosphodiester backbone linkage.

(ii) alteration, e.g., replacement, of a constituent of the ribose sugar, e.g., of the 2' hydroxyl on the ribose sugar;

(iii) wholesale replacement of the phosphate moiety with "dephospho" linkers;

(iv) modification or replacement of a naturally occurring base with a non-natural base;

(v) replacement or modification of the ribose-phosphate backbone;

(vi) modification of the 3' end or 5' end of the oligonucleotide, e.g., removal, modification or replacement of a terminal phosphate group or conjugation of a moiety, e.g., a fluorescently labeled moiety, to either the 3" or 5' end of oligonucleotide; and (vii) modification of the sugar (e.g., six membered rings).

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule.

As oligonucleotides are polymers of subunits or monomers, many of the modifications described herein can occur at a position which is repeated within an oligonucleotide, e.g., a modification of a nucleobase, a sugar, a phosphate moiety, or the non-bridging oxygen of a phosphate moiety. It is not necessary for all positions in a given oligonucleotide to be uniformly modified, and in fact more than one of the aforementioned modifications may be incorporated in a single oligonucleotide or even at a single nucleoside within an oligonucleotide.

In some cases the modification will occur at all of the subject positions in the oligonucleotide but in many, and in fact in most cases it will not. By way of example, a modification may only occur at a 3' or 5' terminal position, may only occur in the internal region, may only occur in a terminal regions, e.g. at a position on a terminal nucleotide or in the last 2, 3, 4, 5, or 10 nucleotides of an oligonucleotide. A modification may occur in a double strand region, a single strand region, or in both. A modification may occur only in the double strand region of an oligonucleotide or may only occur in a single strand region of an oligonucleotide. E.g., a phosphorothioate modification at a non-bridging oxygen position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. The 5' end or ends can be phosphorylated.

A modification described herein may be the sole modification, or the sole type of modification included on multiple nucleotides, or a modification can be combined with one or more other modifications described herein. The modifications described herein can also be combined onto an oligonucleotide, e.g. different nucleotides of an oligonucleotide have different modifications described herein.

In some embodiments it is particularly preferred, e.g., to enhance stability, to include particular nucleobases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Specific modifications are discussed in more detail below.

The Phosphate Group

The phosphate group is a negatively charged species. The charge is distributed equally over the two non-bridging oxygen atoms. However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. In one embodiment, one of the non-bridging phosphate oxygen atoms in the phosphate backbone moiety can be replaced by any of the following: S, Se, BR$_3$ (R is hydrogen, alkyl, aryl), C (i.e. an alkyl group, an aryl group, etc. . . . ), H, NR$_2$ (R is hydrogen, alkyl, aryl), or OR (R is alkyl or aryl). The phosphorous atom in an unmodified phosphate group is achiral. However, replacement of one of the non-bridging oxygens with one of the above atoms or groups of atoms renders the phosphorous atom chiral; in other words a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligoribonucleotides diastereomers. Thus, while not wishing to be bound by theory, modifications to both non-bridging oxygens, which eliminate the chiral center, e.g. phosphorodithioate formation, may be desirable in that they cannot produce diastereomer mixtures. Thus, the non-bridging oxygens can be independently any one of S, Se, B, C, H, N, or OR (R is alkyl or aryl).

The phosphate linker can also be modified by replacement of bridging oxygen, (i.e. oxygen that links the phosphate to the nucleoside), with nitrogen (bridged phosphoroamidates), sulfur (bridged phosphorothioates) and carbon (bridged methylenephosphonates). The replacement can occur at the either linking oxygen or at both the linking oxygens. When the bridging oxygen is the 3'-oxygen of a nucleoside, replacement with carbon is preferred. When the bridging oxygen is the 5'-oxygen of a nucleoside, replacement with nitrogen is preferred.

Replacement of the Phosphate Group

The phosphate group can be replaced by non-phosphorus containing connectors. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Modified phosphate linkages where at least one of the oxygens linked to the phosphate has been replaced or the phosphate group has been replaced by a non-phosphorous group, are also referred to as "non-phosphodiester backbone linkage."

Replacement of Ribophosphate Backbone

Oligonucleotide-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone. Examples include the mophilino, cyclobutyl, pyrrolidine and peptide nucleic acid (PNA) nucleoside surrogates. A preferred surrogate is a PNA surrogate.

Sugar Modifications

An oligonucleotide can include modification of all or some of the sugar groups of the nucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2'-alkoxide ion. The 2'-alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O(CH$_2$CH$_2$O)$_n$CH$_2$CH$_2$OR; "locked" nucleic acids (LNA) in which the 2' hydroxyl is connected, e.g., by a methylene bridge, to the 4' carbon of the same ribose sugar; O-AMINE (AMINE=NH$_2$; alkylamino, dialkylamino, heterocyclyl, arylamino, diaryl amino, heteroaryl amino, or diheteroaryl amino, ethylene diamine, polyamino) and aminoalkoxy, O(CH$_2$)$_n$AMINE, (e.g., AMINE=NH$_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), (OCH$_2$CH$_2$OCH$_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. NH$_2$; alkylamino, dialkylamino, heterocyclyl, arylamino, diaryl amino, heteroaryl amino, diheteroaryl amino, or amino acid); NH(CH$_2$CH$_2$NH)$_n$CH$_2$CH$_2$-AMINE (AMINE=NH$_2$; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thioalkyl; thioalkoxy; and alkyl, cycloalkyl, aryl, alkenyl and alkynyl, which may be optionally substituted with e.g., an amino functionality.

The sugar group can also contain one or more carbons that possess the opposite stereochemical configuration than that of the corresponding carbon in ribose. Thus, an oligonucleotide can include nucleotides containing e.g., arabinose, as the sugar. The monomer can have an alpha linkage at the 1' position on the sugar, e.g., alpha-nucleosides. Oligonucleotides can also include "abasic" sugars, which lack a nucleobase at C-1'. These abasic sugars can also be further containing modifications at one or more of the constituent sugar atoms. Oligonucleotides can also contain one or more sugars that are in the L form, e.g. L-nucleosides.

Preferred substituents are 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH$_2$-(4'-C) (LNA), 2'-O—CH$_2$CH$_2$-(4'-C) (ENA), 2'-O-aminopropyl (2'-O-AP), 2'-O-dimethylaminoethyl (2'-O-DMAOE), 2'-O- dimethylaminopropyl (2'-O-DMAP) and 2'-O-dimethylaminoethyloxyethyl (2'-O-DMAEOE).

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs).

When a linker/phosphate-functional molecular entity-linker/phosphate array is interposed between two strands of a dsRNA, this array can substitute for a hairpin RNA loop in a hairpin-type RNA agent.

Terminal modifications useful for modulating activity include modification of the 5' end with phosphate or phosphate analogs. E.g., in preferred embodiments antisense strands of dsRNAs, are 5' phosphorylated or include a phosphoryl analog at the 5' prime terminus. 5'-phosphate modifications include those which are compatible with RISC mediated gene silencing. Modifications at the 5'-terminal end can also be useful in stimulating or inhibiting the immune system of a subject. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5');

5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g. 5'-alpha-thiotriphosphate, 5'-beta-thiotriphosphate, 5'-gamma-thiotriphosphate, etc.), 5'-phosphoramidates ((HO)$_2$(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'-). Other embodiments include replacement of oxygen/sulfur with BH$_3$, BH$_3^-$ and/or Se.

Terminal modifications can also be useful for monitoring distribution, and in such cases the preferred groups to be added include fluorophores, e.g., fluorescein or an Alexa dye, e.g., Alexa 488. Terminal modifications can also be useful for enhancing uptake, useful modifications for this include cholesterol. Terminal modifications can also be useful for cross-linking an RNA agent to another moiety; modifications useful for this include mitomycin C.

End-caps for exonuclease protection

Nucleobases

Adenine, guanine, cytosine and uracil are the most common bases found in RNA. These bases can be modified or replaced to provide oligonucleotides having improved properties. For example, nuclease resistant oligonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases and "universal bases" can be employed. Examples include 2-(halo)adenine, 2-(alkyl)adenine, 2-(propyl)adenine, 2-(amino)adenine, 2-(aminoalkyl)adenine, 2-(aminopropyl)adenine, 2-(methylthio)-$N^6$-(isopentenyl)adenine, 6-(alkyl)adenine, 6-(methyl)adenine, 7-(deaza)adenine, 8-(alkenyl)adenine, 8-(alkyl)adenine, 8-(alkynyl)adenine, 8-(amino)adenine, 8-(halo)adenine, 8-(hydroxyl)adenine, 8-(thioalkyl)adenine, 8-(thiol)adenine, $N^6$-(isopentyl)adenine, $N^6$-(methyl)adenine, $N^6$, $N^6$-(dimethyl)adenine, 2-(alkyl)guanine, 2-(propyl)guanine, 6-(alkyl)guanine, 6-(methyl)guanine, 7-(alkyl)guanine, 7-(methyl)guanine, 7-(deaza)guanine, 8-(alkyl)guanine, 8-(alkenyl)guanine, 8-(alkynyl)guanine, 8-(amino)guanine, 8-(halo)guanine, 8-(hydroxyl)guanine, 8-(thioalkyl)guanine, 8-(thiol)guanine, N-(methyl)guanine, 2-(thio)cytosine, 3-(deaza)-5-(aza)cytosine, 3-(alkyl)cytosine, 3-(methyl)cytosine, 5-(alkyl)cytosine, 5-(alkynyl)cytosine, 5-(halo)cytosine, 5-(methyl)cytosine, 5-(propynyl)cytosine, 5-(propynyl)cytosine, 5-(trifluoromethyl)cytosine, 6-(azo)cytosine, $N^4$-(acetyl)cytosine, 3-(3-amino-3-carboxypropyl)uracil, 2-(thio)uracil, 5-(methyl)-2-(thio)uracil, 5-(methylaminomethyl)-2-(thio)uracil, 4-(thio)uracil, 5-(methyl)-4-(thio)uracil, 5-(methylaminomethyl)-4-(thio)uracil, 5-(methyl)-2,4-(dithio)uracil, 5-(methylaminomethyl)-2,4-(dithio)uracil, 5-(2-aminopropyl)uracil, 5-(alkyl)uracil, 5-(alkynyl)uracil, 5-(allylamino)uracil, 5-(aminoallyl)uracil, 5-(aminoalkyl)uracil, 5-(guanidiniumalkyl)uracil, 5-(1,3-diazole-1-alkyl)uracil, 5-(cyanoalkyl)uracil, 5-(dialkylaminoalkyl)uracil, 5-(dimethylaminoalkyl)uracil, 5-(halo)uracil, 5-(methoxy)uracil, uracil-5-oxyacetic acid, 5-(methoxycarbonylmethyl)-2-(thio)uracil, 5-(methoxycarbonyl-methyl)uracil, 5-(propynyl)uracil, 5-(propynyl)uracil, 5-(trifluoromethyl)uracil, 6-(azo)uracil, dihydrouracil, $N^3$-(methyl)uracil, 5-uracil (i.e., pseudouracil), 2-(thio)pseudouracil, 4-(thio)pseudouracil, 2,4-(dithio)pseudouracil, 5-(alkyl)pseudouracil, 5-(methyl)pseudouracil, 5-(alkyl)-2-(thio)pseudouracil, 5-(methyl)-2-(thio)pseudouracil, 5-(alkyl)-4-(thio)pseudouracil, 5-(methyl)-4-(thio)pseudouracil, 5-(alkyl)-2,4-(dithio)pseudouracil, 5-(methyl)-2,4-(dithio)pseudouracil, 1-substituted pseudouracil, 1-substituted 2(thio)-pseudouracil, 1-substituted 4-(thio)pseudouracil, 1-substituted 2,4-(dithio)pseudouracil, 1-(aminocarbonylethylenyl)-pseudouracil, 1-(aminocarbonylethylenyl)-2(thio)-pseudouracil, 1-(aminocarbonylethylenyl)-4-(thio)pseudouracil, 1-(aminocarbonylethylenyl)-2,4-(dithio)pseudouracil, 1-(aminoalkylaminocarbonylethylenyl)-pseudouracil, 1-(aminoalkylaminocarbonylethylenyl)-2(thio)-pseudouracil, 1-(aminoalkylaminocarbonylethylenyl)-4-(thio)pseudouracil, 1-(aminoalkylaminocarbonylethylenyl)-2,4-(dithio)pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkylhydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza) indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenzyl, tetracenyl, pentacenyl, difluorotolyl, 4-(fluoro)-6-(methyl)benzimidazole, 4-(methyl)benzimidazole, 6-(azo)thymine, 2-pyridinone, 5-nitroindole, 3-nitropyrrole, 6-(aza)pyrimidine, 2-(amino) purine, 2,6-(diamino)purine, 5-substituted pyrimidines, $N^2$-substituted purines, $N^6$-substituted purines, $O^6$-substituted purines, substituted 1,2,4-triazoles, or any O-alkylated or N-alkylated derivatives thereof;

Further purines and pyrimidines include those disclosed in U.S. Pat. No. 3,687,808, hereby incorporated by reference, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Cationic Groups

Modifications to oligonucleotides can also include attachment of one or more cationic groups to the sugar, base, and/or the phosphorus atom of a phosphate or modified phosphate backbone moiety. A cationic group can be attached to any atom capable of substitution on a natural, unusual or universal base. A preferred position is one that does not interfere with hybridization, i.e., does not interfere with the hydrogen bonding interactions needed for base pairing. A cationic group can be attached e.g., through the C2' position of a sugar or analogous position in a cyclic or acyclic sugar surrogate. Cationic groups can include e.g., protonated amino groups, derived from e.g., O-AMINE (AMINE=$NH_2$; alkylamino, dialkylamino, heterocyclyl, arylamino, diaryl amino, heteroaryl amino, or diheteroaryl amino, ethylene diamine, polyamino); aminoalkoxy, e.g., $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino); amino (e.g. $NH_2$; alkylamino, dialkylamino, heterocyclyl, arylamino, diaryl amino, heteroaryl amino, diheteroaryl amino, or amino acid); or $NH(CH_2CH_2NH)_n$ $CH_2CH_2$-AMINE (AMINE=$NH_2$; alkylamino, dialkylamino, heterocyclyl, arylamino, diaryl amino, heteroaryl amino, or diheteroaryl amino).

End-Caps for Exonuclease Protection

Placement within an Oligonucleotide

Some modifications may preferably be included on an oligonucleotide at a particular location, e.g., at an internal position of a strand, or on the 5' or 3' end of an oligonucleotide. A preferred location of a modification on an oligonucleotide, may confer preferred properties on the agent. For example, preferred locations of particular modifications may confer optimum gene silencing properties, or increased resistance to endonuclease or exonuclease activity.

One or more nucleotides of an oligonucleotide may have a 2'-5' linkage. One or more nucleotides of an oligonucleotide may have inverted linkages, e.g. 3'-3', 5'-5', 2'-2' or 2'-5' linkages.

A double-stranded oligonucleotide may include at least one 5'-uridine-adenine-3' (5'-UA-3') dinucleotide wherein the uridine is a 2'-modified nucleotide, or a terminal 5'-uridine-guanine-3' (5'-UG-3') dinucleotide, wherein the 5'-uridine is a 2'-modified nucleotide, or a terminal 5'-cytidine-adenine-3' (5'-CA-3') dinucleotide, wherein the 5'-cytidine is a 2'-modified nucleotide, or a terminal 5'-uridine-uridine-3' (5'-UU-3') dinucleotide, wherein the 5'-uridine is a 2'-modified nucleotide, or a terminal 5'-cytidine-cytidine-3' (5'-CC-3') dinucleotide, wherein the 5'-cytidine is a 2'-modified nucleotide, or a terminal 5'-cytidine-uridine-3' (5'-CU-3') dinucleotide, wherein the 5'-cytidine is a 2'-modified nucleotide, or a terminal 5'-uridine-cytidine-3' (5'-UC-3') dinucleotide, wherein the 5'-uridine is a 2'-modified nucleotide. Double-stranded oligonucleotides including these modifications are particularly stabilized against endonuclease activity.

General References

The oligoribonucleotides and oligoribonucleosides used in accordance with this invention may be synthesized with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3,2'-O-Methyloligoribonucleotide-s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta*, 1995, 78, 486-504; Beaucage, S. L. and Iyer, R. P., *Tetrahedron*, 1992, 48, 2223-2311 and Beaucage, S. L. and Iyer, R. P., *Tetrahedron*, 1993, 49, 6123-6194, or references referred to therein. Modification described in WO 00/44895, WO01/75164, or WO02/44321 can be used herein. The disclosure of all publications, patents, and published patent applications listed herein are hereby incorporated by reference.

Phosphate Group References

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. No. 5,256,775 or U.S. Pat. No. 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. *J. Org. Chem.* 2001, 66, 2789-2801. Preparation of sulfur bridged nucleotides is described in Sproat et al. *Nucleosides Nucleotides* 1988, 7,651 and Crosstick et al. *Tetrahedron Lett.* 1989, 30, 4693.

Sugar Group References

Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.*, 1993, 36, 831-841), 2'-MOE (Martin, P. *Helv. Chim. Acta* 1996, 79, 1930-1938), "LNA" (Wengel, J. *Acc. Chem. Res.* 1999, 32, 301-310).

Replacement of the Phosphate Group References

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages can be prepared as is described in U.S. Pat. Nos. 5,378,825, 5,386,023, 5,489, 677 and in published PCT applications PCT/US92/04294 and PCT/US92/04305 (published as WO 92/20822 WO and 92/20823, respectively). Formacetal and thioformacetal linked oligoribonucleosides can be prepared as is described in U.S. Pat. Nos. 5,264,562 and 5,264,564. Ethylene oxide linked oligoribonucleosides can be prepared as is described in U.S. Pat. No. 5,223,618. Siloxane replacements are described in Cormier, J. F. et al. *Nucleic Acids Res.* 1988, 16, 4583. Carbonate replacements are described in Tittensor, J. R. *J. Chem. Soc. C* 1971, 1933. Carboxymethyl replacements are described in Edge, M. D. et al. *J. Chem. Soc. Perkin Trans.* 11972, 1991. Carbamate replacements are described in Stirchak, E. P. Nucleic Acids Res. 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. No. 5,539,083.

Terminal Modification References

Terminal modifications are described in Manoharan, M. et al. *Antisense and Nucleic Acid Drug Development* 12, 103-128 (2002) and references therein.

Bases References

N-2 substituted purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908. Additional references are disclosed in the above section on base modifications Oligonucleotide Production The oligonucleotide compounds of the invention can be prepared using solution-phase or solid-phase organic synthesis. Organic synthesis offers the advantage that the oligonucleotide strands comprising non-natural or modified nucleotides can be easily prepared. Any other means for such synthesis known in the art may additionally or alternatively be employed. It is also known to use similar techniques to prepare other oligonucleotides, such as the phosphorothioates, phosphorodithioates and alkylated derivatives. The double-stranded oligonucleotide compounds of the invention may be prepared using a two-step procedure. First, the individual strands of the double-stranded molecule are prepared separately. Then, the component strands are annealed.

Regardless of the method of synthesis, the oligonucleotide can be prepared in a solution (e.g., an aqueous and/or organic solution) that is appropriate for formulation. For example, the oligonucleotide preparation can be precipitated and redissolved in pure double-distilled water, and lyophilized. The dried oligonucleotide can then be resuspended in a solution appropriate for the intended formulation process.

Teachings regarding the synthesis of particular modified oligonucleotides may be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having .beta.-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262,241, and 5,459,255, drawn to, inter alia, methods of synthesizing 2'-fluoro-oligonucleotides.

Ligands

A wide variety of entities can be coupled to the oligonucleotides of the present invention. Preferred moieties are ligands, which are coupled, preferably covalently, either directly or indirectly via an intervening tether.

In preferred embodiments, a ligand alters the distribution, targeting or lifetime of the molecule into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Ligands providing enhanced affinity for a selected target are also termed targeting ligands.

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In one embodiment, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68). In one embodiment, the endosomolytic component may contain a chemical group (e.g., an amino acid) which will undergo a change in charge or protonation in response to a change in pH. The endosomolytic component may be linear or branched. Exemplary primary sequences of peptide based endosomolytic ligands are shown in Table 1.

TABLE 1

List of peptides with endosomolytic activity.

| Name | Sequence (N to C) | Ref. |
|---|---|---|
| GALA | AALEALAEALEALAEALEALAEAAAAGGC | 1 |
| EALA | AALAEALAEALAEALAEALAEALAAAAGGC<br>ALEALAEALEALAEA | 2<br>3 |
| INF-7 | GLFEAIEGFIENGWEGMIWDYG | 4 |
| Inf HA-2 | GLFGAIAGFIENGWEGMIDGWYG | 5 |
| diINF-7 | GLF EAI EGFI ENGW EGMI DGWYGC<br>GLF EAI EGFI ENGW EGMI DGWYGC | 5 |
| diINF3 | GLF EAI EGFI ENGW EGMI DGGC<br>GLF EAI EGFI ENGW EGMI DGGC | 6 |
| GLF | GLFGALAEALAEALAEHLAEALAEALEALAAGGSC | 6 |
| GALA-INF3 | GLFEAIEGFIENGWEGLAEALAEALEALAAGGSC | 6 |
| INF-5 | GLF EAI EGFI ENGW EGnI DG K<br>GLF EAI EGFI ENGW EGnI DG | 4 | n, norleucine
References
1. Subbarao et al., Biochemistry, 1987, 26: 2964-2972.
2. Vogel et al., J. Am. Chem. Soc., 1996, 118: 1581-1586
3. Turk, M. J., Reddy, J. A. et al. (2002). Characterization of a novel pH-sensitive peptide that enhances drug release from folate-targeted liposomes at endosomal pHs. Biochim. Biophys. Acta 1559, 56-68.
4. Plank, C. Oberhauser, B. Mechtler, K. Koch, C. Wagner, E. (1994). The influence of endosome-disruptive peptides on gene transfer using synthetic virus-like gene transfer systems, J. Biol. Chem. 269 12918-12924.
5. Mastrobattista, E., Koning, G. A. et al. (2002). Functional characterization of an endosome-disruptive peptide and its application in cytosolic delivery of immunoliposome-entrapped proteins. J. Biol. Chem. 277, 27135-43.
6. Oberhauser, B., Plank, C. et al. (1995). Enhancing endosomal exit of nucleic acids using pH-sensitive viral fusion peptides. Deliv. Strategies Antisense Oligonucleotide Ther. 247-66.

Ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer. Table 2 shows some examples of targeting ligands and their associated receptors.

TABLE 2

Targeting Ligands and their associated receptors

| Liver Cells | Ligand | Receptor |
|---|---|---|
| 1) Parenchymal Cell (PC) (Hepatocytes) | Galactose | ASGP-R (Asiologlycoprotein receptor) |
| | Gal NAc (n-acetyl-galactosamine) | ASPG-R Gal NAc Receptor |
| | Lactose | |
| | Asialofetuin | ASPG-r |
| 2) Sinusoidal Endothelial Cell (SEC) | Hyaluronan | Hyaluronan receptor |
| | Procollagen | Procollagen receptor |
| | Negatively charged molecules | Scavenger receptors |
| | Mannose | Mannose receptors |
| | N-acetyl Glucosamine | Scavenger receptors |
| | Immunoglobulins | Fc Receptor |
| | LPS | CD14 Receptor |
| | Insulin | Receptor mediated transcytosis |
| | Transferrin | Receptor mediated transcytosis |
| | Albumins | Non-specific |
| | Sugar-Albumin conjugates | |
| | Mannose-6-phosphate | Mannose-6-phosphate receptor |

TABLE 2-continued

Targeting Ligands and their associated receptors

| Liver Cells | Ligand | Receptor |
|---|---|---|
| 3) Kupffer Cell (KC) | Mannose<br>Fucose<br>Albumins<br>Mannose-albumin conjugates | Mannose receptors<br>Fucose receptors<br>Non-specific |

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the oligonucleotide into the cell by activating an inflammatory response, for example. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long (see Table 3, for example).

TABLE 3

Exemplary Cell Permeation Peptides.

| Cell Permeation Peptide | Amino acid Sequence | Reference |
|---|---|---|
| Penetratin | RQIKIWFQNRRMKWKK | Derossi et al., J. Biol. Chem. 269: 10444, 1994 |

TABLE 3-continued

Exemplary Cell Permeation Peptides.

| Cell Permeation Peptide | Amino acid Sequence | Reference |
| --- | --- | --- |
| Tat fragment (48-60) | GRKKRRQRRRPPQC | Vives et al., J. Biol. Chem., 272: 16010, 1997 |
| Signal Sequence-based peptide | GALFLGWLGAAGSTMGAWSQPKKKRKV | Chaloin et al., Biochem. Biophys. Res. Commun., 243: 601, 1998 |
| PVEC | LLIILRRRIRKQAHAHSK | Elmquist et al., Exp. Cell Res., 269: 237, 2001 |
| Transportan | GWTLNSAGYLLKINLKALAALAKKIL | Pooga et al., FASEB J., 12: 67, 1998 |
| Amphiphilic model peptide | KLALKLALKALKAALKLA | Oehlke et al., Mol. Ther., 2: 339, 2000 |
| $Arg_9$ | RRRRRRRRR | Mitchell et al., J. Pept. Res., 56: 318, 2000 |
| Bacterial cell wall permeating | KFFKFFKFFK | |
| LL-37 | LLGDFFRKSKEKIGKEFKRIVQRIKDFLRNLVPRTES | |
| Cecropin P1 | SWLSKTAKKLENSAKKRISEGIAIAIQGGPR | |
| α-defensin | ACYCRIPACIAGERRYGTCIYQGRLWAFCC | |
| b-defensin | DHYNCVSSGGQCLYSACPIFTKIQGTCYRGKAKCCK | |
| Bactenecin | RKCRIVVIRVCR | |
| PR-39 | RRRPRPPYLPRPRPPPFFPPRLPPRIPPGFPPRFPPRFPGKR-NH2 | |
| Indolicidin | ILPWKWPWWPWRR-NH2 | |

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP. An RFGF analogue (e.g., amino acid sequence AALLPVLLAAP) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ) and the Drosophila Antennapedia protein (RQIKIWFQNRRMKWKK) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting of an iRNA agent to tumors of a variety of other tissues, including the lung, kidney, spleen, or liver (Aoki et al., Cancer Gene Therapy 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_v\beta_3$ (Haubner et al., Jour. Nucl. Med., 42:326-336, 2001).

Peptides that target markers enriched in proliferating cells can be used. E.g., RGD containing peptides and peptidomimetics can target cancer cells, in particular cells that exhibit an integrin. Thus, one could use RGD peptides, cyclic peptides containing RGD, RGD peptides that include D-amino acids, as well as synthetic RGD mimics. In addition to RGD, one can use other moieties that target the integrin ligand. Generally, such ligands can be used to control proliferating cells and angiogenesis. Preferred conjugates of this type ligands that targets PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In one embodiment, a targeting peptide can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, $H_2A$ peptides, Xenopus peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an aptamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycarboxylates, polyacations, masked oligo or poly cations or anions, acetals, polyacetals, ketals/polyketyals, orthoesters, polymers with masked or unmasked cationic or anionic charges, dendrimers with masked or unmasked cationic or anionic charges.

PK modulator stands for pharmacokinetic modulator. PK modulator include lipophiles, bile acids, steroids, phospholipid analogues, peptides, protein binding agents, PEG, vitamins etc. Exemplary PK modulator include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g. oligonucleotides of about 5 bases, 10 bases, 15 bases or 20 bases, comprising multiple of phosphorothioate linkages in the backbone are also amenable to the present invention as ligands (e.g. as PK modulating ligands).

In addition, aptamers that bind serum components (e.g. serum proteins) are also amenable to the present invention as PK modulating ligands.

Other ligand conjugates amenable to the invention are described in copending applications U.S. Ser. No. 10/916, 185, filed Aug. 10, 2004; U.S. Ser. No. 10/946,873, filed Sep. 21, 2004; U.S. Ser. No. 10/833,934, filed Aug. 3, 2007; U.S. Ser. No. 11/115,989 filed Apr. 27, 2005 and U.S. Ser. No. 11/944,227 filed Nov. 21, 2007, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

Ligands can be coupled to the oligonucleotides at various places, for example, 3'-end, 5'-end, and/or at an internal position. In preferred embodiments, the ligand is attached to the oligonucleotides via an intervening tether, e.g. a carrier described herein. The ligand or tethered ligand may be present on a monomer when said monomer is incorporated into the growing strand. In some embodiments, the ligand may be incorporated via coupling to a "precursor" monomer after said "precursor" monomer has been incorporated into the growing strand. For example, a monomer having, e.g., an amino-terminated tether (i.e., having no associated ligand), e.g., TAP-$(CH_2)_n NH_2$ may be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction may be incorporated e.g., an azide or alkyne terminated tether/ linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands. In some embodiments, a double-stranded iRNA agent contains a ligand conjugated to the sense strand. In other embodiments, a double-stranded iRNA agent contains a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithioate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

There are numerous methods for preparing conjugates of oligonucleotides. Generally, an oligomeric compound is attached to a conjugate moiety by contacting a reactive group (e.g., OH, SH, amine, carboxyl, aldehyde, and the like) on the oligomeric compound with a reactive group on the conjugate moiety. In some embodiments, one reactive group is electrophilic and the other is nucleophilic.

For example, an electrophilic group can be a carbonyl-containing functionality and a nucleophilic group can be an amine or thiol. Methods for conjugation of nucleic acids and related oligonucleotides with and without linking groups are well described in the literature such as, for example, in Manoharan in Antisense Research and Applications, Crooke and LeBleu, eds., CRC Press, Boca Raton, Fla., 1993, Chapter 17, which is incorporated herein by reference in its entirety.

Representative United States patents that teach the preparation of oligonucleotide conjugates include, but are not limited to, U.S. Pat. Nos. 4,828,979; 4,948,882; 5,218, 105; 5,525,465; 5,541,313; 5,545,730; 5,552,538; 5,578,717, 5,580,731; 5,580,731; 5,591,584; 5,109,124; 5,118, 802; 5,138,045; 5,414,077; 5,486,603; 5,512,439; 5,578,718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,149,782; 5,214,136; 5,245,022; 5,254,469; 5,258,506; 5,262,536; 5,272,250; 5,292,873; 5,317,098; 5,371,241, 5,391,723; 5,416,203, 5,451,463; 5,510, 475; 5,512,667; 5,514,785; 5,565,552; 5,567,810; 5,574, 142; 5,585,481; 5,587,371; 5,595,726; 5,597,696; 5,599, 923; 5,599,928; 5,672,662; 5,688,941; 5,714,166; 6,153,737; 6,172,208; 6,300,319; 6,335,434; 6,335,437; 6,395, 437; 6,444,806; 6,486,308; 6,525,031; 6,528,631; 6,559,279; each of which is herein incorporated by reference.

Linkers

In one embodiment, the covalent linkages between the oligonucleotide and other components, e.g. a ligand or a ligand carrying monomer may be mediated by a linker. This linker may be cleavable or non-cleavable, depending on the application. In one embodiment, a cleavable linker may be used to release the nucleic acid after transport to the desired target. The intended nature of the conjugation or coupling interaction, or the desired biological effect, will determine the choice of linker group.

The term "linker" means an organic moiety that connects two parts of a compound. Linkers typically comprise a direct bond or an atom such as oxygen or sulfur, a unit such as $NR^1$, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alk- enylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylherereoaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where R' is hydrogen, acyl, aliphatic or substituted aliphatic.

In one embodiment, the linker is $-[(P-Q-R)_q-X-(P'-Q'-R)_{q'}]_{q''}-T-$, wherein:

P, R, T, P' and R' are each independently for each occurrence absent, CO, NH, O, S, OC(O), NHC(O), $CH_2$, $CH_2NH$, $CH_2O$; $NHCH(R^a)C(O)$, $-C(O)-CH(R^a)-NH-$, C(O)-(optionally substituted alkyl)-NH—, CH=N—O,

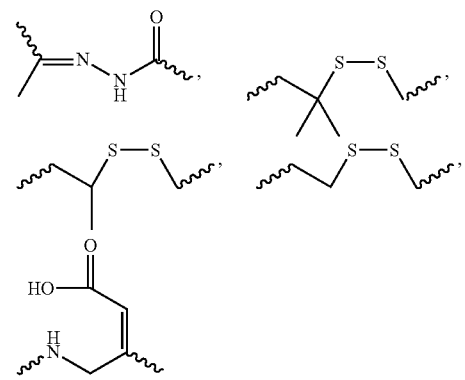

or heterocyclyl;

Q and Q' are each independently for each occurrence absent, $-(CH_2)_n-$, $-C(R^{100})(R^{200})(CH_2)_n-$, $-(CH_2)_nC(R^{100})(R^{200})-$, $-(CH_2CH_2O)_mCH_2CH_2-$, or $-(CH_2CH_2O)_mCH_2CH_2NH-$;

X is absent or a cleavable linking group;

$R^a$ is H or an amino acid side chain;

$R^{100}$ and $R^{200}$ are each independently for each occurrence H, $CH_3$, OH, SH or $N(R^X)_2$;

$R^X$ is independently for each occurrence H, methyl, ethyl, propyl, isopropyl, butyl or benzyl;

q, q' and q" are each independently for each occurrence 0-20 and wherein the repeating unit can be the same or different;

n is independently for each occurrence 1-20; and m is independently for each occurrence 0-50.

In one embodiment, the linker comprises at least one cleavable linking group.

In one embodiment, the linker is a branched linker. The branchpoint of the branched linker may be at least trivalent, but may be a tetravalent, pentavalent or hexavalent atom, or a group presenting such multiple valencies. In one embodiment, the branchpoint is, —N, —N(O)—C, —O—C, —S—C, —SS—C, —C(O)N(O)—C, —OC(O)N(O)—C, —N(O)C(O)—C, or —N(O)C(O)O—C; wherein Q is independently for each occurrence H or optionally substituted alkyl. In other embodiment, the branchpoint is glycerol or a glycerol derivative.

Cleavable Linking Groups

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linking Groups

Acid cleavable linking groups are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynylene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NHCHR$^B$C(O)—, where R$^A$ and R$^B$ are the R groups of the two adjacent amino acids. These candidates can be evaluated using methods analogous to those described above.

Formulations

For ease of exposition the formulations, compositions and methods in this section are discussed largely with regard to RNAi agents. It may be understood, however, that these formulations, compositions and methods can be practiced with other oligonucleotides of the invention, e.g., antisense, antagomir, aptamer and ribozyme, and such practice is within the invention.

A formulated RNAi composition can assume a variety of states. In some examples, the composition is at least partially crystalline, uniformly crystalline, and/or anhydrous (e.g., less than 80, 50, 30, 20, or 10% water). In another example, the RNAi is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the RNAi composition is formulated in a manner that is compatible with the intended method of administration.

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

An RNAi preparation can be formulated in combination with another agent, e.g., another therapeutic agent or an agent that stabilizes the RNAi agent, e.g., a protein that complex with RNAi agent to form an iRNP. Still other agents include chelators, e.g., EDTA (e.g., to remove divalent cations such as Mg$^{2+}$), salts, RNAse inhibitors (e.g., a broad specificity RNAse inhibitor such as RNAsin) and so forth.

In one embodiment, the RNAi preparation includes another RNAi agent, e.g., a second RNAi that can mediated RNAi with respect to a second gene, or with respect to the same gene. Still other preparation can include at least 3, 5, ten, twenty, fifty, or a hundred or more different RNAi species. Such RNAi agents can mediate RNAi with respect to a similar number of different genes.

In one embodiment, the RNAi preparation includes at least a second therapeutic agent (e.g., an agent other than RNA or DNA). For example, an RNAi composition for the treatment of a viral disease, e.g., HIV, might include a known antiviral agent (e.g., a protease inhibitor or reverse transcriptase inhibitor). In another example, an RNAi agent composition for the treatment of a cancer might further comprise a chemotherapeutic agent.

Exemplary formulations are discussed below:

Liposomes

The oligonucleotides of the invention, e.g. antisense, antagomir, aptamer, ribozyme and RNAi agent can be formulated in liposomes. As used herein, a liposome is a structure having lipid-containing membranes enclosing an aqueous interior. Liposomes may have one or more lipid membranes. Liposomes may be characterized by membrane type and by size. Small unilamellar vesicles (SUVs) have a single membrane and typically range between 0.02 and 0.05 μm in diameter; large unilamellar vesicles (LUVS) are typically larger than 0.05 μm. Oligolamellar large vesicles and multilamellar vesicles have multiple, usually concentric, membrane layers and are typically larger than 0.1 μm. Liposomes with several nonconcentric membranes, i.e., several smaller vesicles contained within a larger vesicle, are termed multivesicular vesicles.

Liposomes may further include one or more additional lipids and/or other components such as cholesterol. Other lipids may be included in the liposome compositions for a variety of purposes, such as to prevent lipid oxidation, to stabilize the bilayer, to reduce aggregation during formation or to attach ligands onto the liposome surface. Any of a number of lipids may be present, including amphipathic, neutral, cationic, and anionic lipids. Such lipids can be used alone or in combination.

Additional components that may be present in a liposomes include bilayer stabilizing components such as polyamide oligomers (see, e.g., U.S. Pat. No. 6,320,017), peptides, proteins, detergents, lipid-derivatives, such as PEG conjugated to phosphatidylethanolamine, PEG conjugated to phosphatidic acid, PEG conjugated to ceramides (see, U.S. Pat. No. 5,885,613), PEG conjugated dialkylamines and PEG conjugated 1,2-diacyloxypropan-3-amines.

Liposome can include components selected to reduce aggregation of lipid particles during formation, which may result from steric stabilization of particles which prevents charge-induced aggregation during formation. Suitable components that reduce aggregation include, but are not limited to, polyethylene glycol (PEG)-modified lipids, monosialoganglioside Gm1, and polyamide oligomers ("PAO") such as (described in U.S. Pat. No. 6,320,017). Exemplary suitable PEG-modified lipids include, but are not limited to, PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Particularly preferred are PEG-modified diacylglycerols and dialkylglycerols. Other compounds with uncharged, hydrophilic, steric-barrier moieties, which prevent aggregation during formation, like PEG, Gm1, or ATTA, can also be coupled to lipids to reduce aggregation during formation. ATTA-lipids are described, e.g., in U.S. Pat. No. 6,320,017, and PEG-lipid conjugates are described, e.g., in U.S. Pat. Nos. 5,820,873, 5,534,499 and 5,885,613. Typically, the concentration of the lipid component selected to reduce aggregation is about 1 to 15% (by mole percent of lipids). It should be noted that aggregation preventing compounds do not necessarily require lipid conjugation to function properly. Free PEG or free ATTA in solution may be sufficient to prevent aggregation. If the liposomes are stable after formulation, the PEG or ATTA can be dialyzed away before administration to a subject.

Neutral lipids, when present in the liposome composition, can be any of a number of lipid species which exist either in an uncharged or neutral zwitterionic form at physiological pH. Such lipids include, for example diacylphosphatidylcholine, diacylphosphatidylethanolamine, ceramide, sphingomyelin, dihydrosphingomyelin, cephalin, and cerebrosides. The selection of neutral lipids for use in liposomes described herein is generally guided by consideration of, e.g., liposome size and stability of the liposomes in the bloodstream. Preferably, the neutral lipid component is a lipid having two acyl groups, (i.e., diacylphosphatidylcholine and diacylphosphatidylethanolamine). Lipids having a variety of acyl chain groups of varying chain length and degree of saturation are available or may be isolated or synthesized by well-known techniques. In one group of embodiments, lipids containing saturated fatty acids with carbon chain lengths in the range of $C_{14}$ to $C_{22}$ are preferred. In another group of embodiments, lipids with mono or diunsaturated fatty acids with carbon chain lengths in the range of $C_{14}$ to $C_{22}$ are used. Additionally, lipids having mixtures of saturated and unsaturated fatty acid chains can be used. Preferably, the neutral lipids used in the present invention are DOPE, DSPC, POPC, DMPC, DPPC or any related phosphatidylcholine. The neutral lipids useful in the present invention may also be composed of sphingomyelin, dihydrosphingomyeline, or phospholipids with other head groups, such as serine and inositol.

The sterol component of the lipid mixture, when present, can be any of those sterols conventionally used in the field of liposome, lipid vesicle or lipid particle preparation. A preferred sterol is cholesterol.

Cationic lipids, when present in the liposome composition, can be any of a number of lipid species which carry a net positive charge at about physiological pH. Such lipids include, but are not limited to, N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3β-(N—(N', N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N,N-dimethyl-2,3-dioleyloxy)propylamine ("DODMA"), N-(1,2-dimyristyloxyprop-3-yl)-N, N-dimethyl-N-hydroxyethyl ammonium bromide ("DMRIE"), 5-carboxyspermylglycine diocaoleyamide ("DOGS"), and dipalmitoylphosphatidylethanolamine 5-carboxyspermyl-amide ("DPPES"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL). Other cationic lipids suitable for lipid particle formation are described in WO98/39359, WO96/37194. Other cationic lipids suitable for liposome formation are described in U.S. Provisional application No. 61/018,616 (filed Jan. 2, 2008), No. 61/039,748 (filed Mar. 26, 2008), No. 61/047,087 (filed Apr. 22, 2008) and No. 61/051,528 (filed May 21-2008), all of which are incorporated by reference in their entireties for all purposes.

Anionic lipids, when present in the liposome composition, can be any of a number of lipid species which carry a net negative charge at about physiological pH. Such lipids include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

"Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospho lipids include sphingomyelin, phosphatidylcholine, phosphatidylethanolamine, phosphatidylserine, phosphatidylinositol, phosphatidic acid, palmitoyloleoylphosphatdylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and β-acyloxyacids, can also be used. Additionally, such amphipathic lipids can be readily mixed with other lipids, such as triglycerides and sterols.

Also suitable for inclusion in the liposome compostions of the present invention are programmable fusion lipids. Liposomes containing programmable fusion lipids have little tendency to fuse with cell membranes and deliver their payload until a given signal event occurs. This allows the liposome to distribute more evenly after injection into an organism or disease site before it starts fusing with cells. The signal event can be, for example, a change in pH, temperature, ionic environment, or time. In the latter case, a fusion delaying or "cloaking" component, such as an ATTA-lipid conjugate or a PEG-lipid conjugate, can simply exchange out of the liposome membrane over time. By the time the liposome is suitably distributed in the body, it has lost sufficient cloaking agent so as to be fusogenic. With other signal events, it is desirable to choose a signal that is associated with the disease site or target cell, such as increased temperature at a site of inflammation.

A liposome can also include a targeting moiety, e.g., a targeting moiety that is specific to a cell type or tissue. Targeting of liposomes with a surface coating of hydrophilic polymer chains, such as polyethylene glycol (PEG) chains, for targeting has been proposed (Allen, et al., *Biochimica et Biophysica Acta* 1237: 99-108 (1995); DeFrees, et al., *Journal of the American Chemistry Society* 118: 6101-6104 (1996); Blume, et al., *Biochimica et Biophysica Acta* 1149: 180-184 (1993); Klibanov, et al., *Journal of Liposome Research* 2: 321-334 (1992); U.S. Pat. No. 5,013,556; Zalipsky, *Bioconjugate Chemistry* 4: 296-299 (1993); Zalipsky, *FEBS Letters* 353: 71-74 (1994); Zalipsky, in Stealth Liposomes Chapter 9 (Lasic and Martin, Eds) CRC Press, Boca Raton Fla. (1995). Other targeting moieties, such as ligands, cell surface receptors, glycoproteins, vitamins (e.g., riboflavin), aptamers and monoclonal antibodies, can also be used. The targeting moieties can include the entire protein or fragments thereof. Targeting mechanisms generally require that the targeting agents be positioned on the surface of the liposome in such a manner that the targeting moiety is available for interaction with the target, for example, a cell surface receptor.

In one approach, a targeting moiety, such as receptor binding ligand, for targeting the liposome is linked to the lipids forming the liposome. In another approach, the targeting moiety is attached to the distal ends of the PEG chains forming the hydrophilic polymer coating (Klibanov, et al., *Journal of Liposome Research* 2: 321-334 (1992); Kirpotin et al., *FEBS Letters* 388: 115-118 (1996)). A variety of different targeting agents and methods are known and available in the art, including those described, e.g., in Sapra, P. and Allen, T M, *Prog. Lipid Res.* 42(5):439-62 (2003); and Abra, R M et al., *J. Liposome Res.* 12:1-3, (2002). Other lipids conjugated with targeting moieties are described in U.S. provisional application No. 61/127,751 (filed May 14, 2008) and PCT application #PCT/US2007/080331 (filed Oct. 3, 2007), all of which are incorporated by reference in their entireties for all purposes.

A liposome composition of the invention can be prepared by a variety of methods that are known in the art. See e.g., U.S. Pat. No. 4,235,871, U.S. Pat. No. 4,897,355 and U.S. Pat. No. 5,171,678; published PCT applications WO 96/14057 and WO 96/37194; Feigner, P. L. et al., *Proc. Natl. Acad. Sci.*, USA (1987) 8:7413-7417, Bangham, et al. *M. Mol. Biol.* (1965) 23:238, Olson, et al. *Biochim. Biophys. Acta* (1979) 557:9, Szoka, et al. *Proc. Natl. Acad. Sci.* (1978) 75: 4194, Mayhew, et al. *Biochim. Biophys. Acta* (1984) 775:169, Kim, et al. *Biochim. Biophys. Acta* (1983) 728:339, and Fukunaga, et al. *Endocrinol.* (1984) 115:757.

For example, a liposome composition of the invention can be prepared by first dissolving the lipid components of a liposome in a detergent so that micelles are formed with the lipid component. The detergent can have a high critical micelle concentration and maybe nonionic. Exemplary detergents include, but are not limited to, cholate, CHAPS, octylglucoside, deoxycholate and lauroyl sarcosine. The RNAi agent preparation e.g., an emulsion, is then added to the micelles that include the lipid components. After condensation, the detergent is removed, e.g., by dialysis, to yield a liposome containing the RNAi agent. If necessary a carrier compound that assists in condensation can be added during the condensation reaction, e.g., by controlled addition. For example, the carrier compound can be a polymer other than a nucleic acid (e.g., spermine or spermidine). To favor condensation, pH of the mixture can also be adjusted.

In another example, liposomes of the present invention may be prepared by diffusing a lipid derivatized with a hydrophilic polymer into preformed liposome, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the RNAi agent is first dispersed by sonication in a lysophosphatidylcholine or other low CMC surfactant (including polymer grafted lipids). The resulting micellar suspension of RNAi agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323.

Other suitable formulations for RNAi agents are described in PCT application #PCT/US2007/080331 (filed Oct. 3, 2007) and U.S. Provisional applications No. 61/018, 616 (filed Jan. 2, 2008), No. 61/039,748 (filed Mar. 26, 2008), No. 61/047,087 (filed Apr. 22, 2008) and No. 61/051, 528 (filed May 21-2008), No. 61/113,179 (filed Nov. 10, 2008) all of which are incorporated by reference in their entireties for all purposes.

Micelles and Other Membranous Formulations

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

As defined herein, "micelles" are a particular type of molecular assembly in which amphipathic molecules are arranged in a spherical structure such that all hydrophobic portions on the molecules are directed inward, leaving the hydrophilic portions in contact with the surrounding aqueous phase. The converse arrangement exists if the environment is hydrophobic.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Exemplary amphiphilic carriers include, but are not limited to, lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-. di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or monounsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Mixed micelle formulation suitable for delivery through transdermal membranes may be prepared by mixing an aqueous solution of the RNAi composition, an alkali metal $C_8$ to $C_{22}$ alkyl sulphate, and an amphiphilic carrier. The amphiphilic carrier may be added at the same time or after addition of the alkali metal alkyl sulphate. Mixed micelles will form with substantially any kind of mixing of the ingredients but vigorous mixing in order to provide smaller size micelles.

In one method a first micelle composition is prepared which contains the RNAi composition and at least the alkali metal alkyl sulphate. The first micelle composition is then mixed with at least three amphiphilic carriers to form a mixed micelle composition. In another method, the micelle composition is prepared by mixing the RNAi composition, the alkali metal alkyl sulphate and at least one of the amphiphilic carriers, followed by addition of the remaining micelle amphiphilic carriers, with vigorous mixing.

Phenol and/or m-cresol may be added to the mixed micelle composition to stabilize the formulation and protect against bacterial growth. Alternatively, phenol and/or m-cresol may be added with the amphiphilic carriers. An isotonic agent such as glycerin may also be added after formation of the mixed micelle composition.

For delivery of the micelle formulation as a spray, the formulation can be put into an aerosol dispenser and the dispenser is charged with a propellant, such as hydrogen-containing chlorofluorocarbons, hydrogen-containing fluorocarbons, dimethyl ether, diethyl ether and HFA 134a (1,1,1,2 tetrafluoroethane).

Emulsions

The oligonucleotides of the present invention may be prepared and formulated as emulsions. Emulsions are typically heterogenous systems of one liquid dispersed in another in the form of droplets (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: non-ionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials is also included in emulsion formulations and contributes to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of FLiPs are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or dsRNAs. Microemulsions have also been effective in the transdermal delivery of active components in both cosmetic and pharmaceutical applications. It is expected that the microemulsion compositions and formulations of the present invention will facilitate the increased systemic absorption of dsRNAs and nucleic acids from the gastrointestinal tract, as well as improve the local cellular uptake of dsRNAs and nucleic acids.

Microemulsions of the present invention may also contain additional components and additives such as sorbitan monostearate (Grill 3), Labrasol, and penetration enhancers to improve the properties of the formulation and to enhance the absorption of the dsRNAs and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Lipid Particles

It has been shown that cholesterol-conjugated sRNAis bind to HDL and LDL lipoprotein particles which mediate cellular uptake upon binding to their respective receptors. Both high-density lipoproteins (HDL) and low density lipoproteins (LDL) play a critical role in cholesterol transport. HDL directs sRNAi delivery into liver, gut, kidney and steroidogenic organs, whereas LDL targets sRNAi primarily to liver (Wolfrum et al. Nature Biotechnology Vol. 25 (2007)). Thus in one aspect the invention provides formulated lipid particles (FLiPs) comprising (a) an oligonucleotide of the invention, e.g., antisense, antagomir, aptamer, ribozyme and an RNAi agent, where said oligonucleotide has been conjugated to a lipophile and (b) at least one lipid component, for example an emulsion, liposome, isolated lipoprotein, reconstituted lipoprotein or phospholipid, to which the conjugated oligonucleotide has been aggregated, admixed or associated.

The stoichiometry of oligonucleotide to the lipid component may be 1:1. Alternatively the stoichiometry may be 1:many, many:1 or many:many, where many is greater than 2.

The FLiP may comprise triacylglycerol, phospho lipids, glycerol and one or several lipid-binding proteins aggregated, admixed or associated via a lipophilic linker molecule with a single- or double-stranded oligonucleotide, wherein said FLiP has an affinity to heart, lung and/or muscle tissue. Surprisingly, it has been found that due to said one or several lipid-binding proteins in combination with the above mentioned lipids, the affinity to heart, lung and/or muscle tissue is very specific. These FLiPs may therefore serve as carrier for oligonucleotides. Due to their affinity to heart, lung and muscle cells, they may specifically transport the oligonucleotides to these tissues. Therefore, the FLiPs according to the present invention may be used for many severe heart, lung and muscle diseases, for example myocarditis, ischemic heart disease, myopathies, cardiomyopathies, metabolic diseases, rhabdomyosarcomas.

One suitable lipid component for FLiP is Intralipid. Intralipid® is a brand name for the first safe fat emulsion for human use. Intralipid® 20% (a 20% intravenous fat emulsion) is a sterile, non-pyrogenic fat emulsion prepared for intravenous administration as a source of calories and essential fatty acids. It is made up of 20% soybean oil, 1.2% egg yolk phospho lipids, 2.25% glycerin, and water for injection. Intralipid® 10% is made up of 10% soybean oil, 1.2% egg yolk phospholipids, 2.25% glycerin, and water for injection. It is further within the present invention that other suitable oils, such as safflower oil, may serve to produce the lipid component of the FLiP.

In one embodiment of the invention is a FLiP comprising a lipid particle comprising 15-25% triacylglycerol, about 1-2% phospholipids and 2-3% glycerol, and one or several lipid-binding proteins.

In another embodiment of the invention the lipid particle comprises about 20% triacylglycerol, about 1.2% phospholipids and about 2.25% glycerol, which corresponds to the total composition of Intralipid, and one or several lipid-binding proteins.

Another suitable lipid component for FLiPs is lipoproteins, for example isolated lipoproteins or more preferably reconstituted lipoproteins. Lipoproteins are particles that contain both proteins and lipids. The lipids or their derivatives may be covalently or non-covalently bound to the proteins. Exemplary lipoproteins include chylomicrons, VLDL (Very Low Density Lipoproteins), IDL (Intermediate Density Lipoproteins), LDL (Low Density Lipoproteins) and HDL (High Density Lipoproteins).

Methods of producing reconstituted lipoproteins have been described in scientific literature, for example see A. Jones, Experimental Lung Res. 6, 255-270 (1984), U.S. Pat. No. 4,643,988 and U.S. Pat. No. 5,128,318, PCT publication WO87/02062, Canadian patent #2,138,925. Other methods of producing reconstituted lipoproteins, especially for apolipoproteins A-I, A-II, A-IV, apoC and apoE have been described in A. Jonas, Methods in Enzymology 128, 553-582 (1986) and G. Franceschini et al. J. Biol. Chem., 260(30), 16321-25 (1985).

The most frequently used lipid for reconstitution is phosphatidyl choline, extracted either from eggs or soybeans. Other phospholipids are also used, also lipids such as triglycerides or cholesterol. For reconstitution the lipids are first dissolved in an organic solvent, which is subsequently evaporated under nitrogen. In this method the lipid is bound in a thin film to a glass wall. Afterwards the apolipoproteins and a detergent, normally sodium cholate, are added and mixed. The added sodium cholate causes a dispersion of the lipid. After a suitable incubation period, the mixture is dialyzed against large quantities of buffer for a longer period of time; the sodium cholate is thereby removed for the most part, and at the same time lipids and apolipoproteins spontaneously form themselves into lipoproteins or so-called reconstituted lipoproteins. As alternatives to dialysis, hydrophobic adsorbents are available which can adsorb detergents (Bio-Beads SM-2, Bio Rad; Amberlite XAD-2, Rohm & Haas) (E. A. Bonomo, J. B. Swaney, J. Lipid Res., 29, 380-384 (1988)), or the detergent can be removed by means of gel chromatography (Sephadex G-25, Pharmacia). Lipoproteins can also be produced without detergents, for example through incubation of an aqueous suspension of a suitable lipid with apolipoproteins, the addition of lipid which was dissolved in an organic solvent, to apolipoproteins, with or without additional heating of this mixture, or through treatment of an apoA-I-lipid-mixture with ultrasound. With these methods, starting, for example, with apoA-I and phosphatidyl choline, disk-shaped particles can be obtained which correspond to lipoproteins in their nascent state. Normally, following the incubation, unbound apolipoproteins and free lipid are separated by means of centrifugation or gel chromatography in order to isolate the homogeneous, reconstituted lipoproteins particles.

Phospholipids used for reconstituted lipoproteins can be of natural origin, such as egg yolk or soybean phospho lipids, or synthetic or semisynthetic origin. The phospho lipids can be partially purified or fractionated to comprise pure fractions or mixtures of phosphatidyl cholines, phosphatidyl ethanolamines, phosphatidyl inositols, phosphatidic acids, phosphatidyl serines, sphingomyelin or phosphatidyl glycerols. According to specific embodiments of the present invention it is preferred to select phospholipids with defined fatty acid radicals, such as dimyristoyl phosphatidyl choline (DMPC), dioleoylphosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoyl-phosphatidylcholine (DPPC), dioleoylphosphatidylglycerol (DOPG), dipalmitoylphosphatidylglycerol (DPPG), -phosphatidylethanolamine (POPE), dioleoylphosphatidylethanolamine 4-(N-maleimidomethyl)-cyclohexane-1-carboxylate (DOPE-mal), and combinations thereof, and the like phosphatidyl cholines with defined acyl groups selected from naturally occurring fatty acids, generally having 8 to 22 carbon atoms. According to a specific embodiment of the present invention phosphatidyl cholines having only saturated fatty acid residues between 14 and 18 carbon atoms are preferred, and of those dipalmitoyl phosphatidyl choline is especially preferred.

Other phospho lipids suitable for reconstitution with lipoproteins include, e.g., phosphatidylcholine, phosphatidylglycerol, lecithin, b, g-dipalmitoyl-a-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, and the like. Non-phosphorus containing lipids may also be used in the liposomes of the compositions of the present invention. These include, e.g., stearylamine, docecylamine, acetyl palmitate, fatty acid amides, and the like.

Besides the phospho lipids, the lipoprotein may comprise, in various amounts at least one nonpolar component which can be selected among pharmaceutical acceptable oils (triglycerides) exemplified by the commonly employed vegetabilic oils such as soybean oil, safflower oil, olive oil, sesame oil, borage oil, castor oil and cottonseed oil or oils from other sources like mineral oils or marine oils including hydrogenated and/or fractionated triglycerides from such sources. Also medium chain triglycerides (MCT-oils, e.g. Miglyol®), and various synthetic or semisynthetic mono-, di- or triglycerides, such as the defined nonpolar lipids disclosed in WO 92/05571 may be used in the present invention as well as acetylated monoglycerides, or alkyl esters of fatty acids, such isopropyl myristate, ethyl oleate (see EP 0 353 267) or fatty acid alcohols, such as oleyl alcohol, cetyl alcohol or various nonpolar derivatives of cholesterol, such as cholesterol esters.

One or more complementary surface active agent can be added to the reconstituted lipoproteins, for example as complements to the characteristics of amphiphilic agent or to improve its lipid particle stabilizing capacity or enable an improved solubilization of the protein. Such complementary agents can be pharmaceutically acceptable non-ionic surfactants which preferably are alkylene oxide derivatives of an organic compound which contains one or more hydroxylic groups. For example ethoxylated and/or propoxylated alcohol or ester compounds or mixtures thereof are commonly available and are well known as such complements to those skilled in the art. Examples of such compounds are esters of sorbitol and fatty acids, such as sorbitan monopalmitate or sorbitan monopalmitate, oily sucrose esters, polyoxyethylene sorbitane fatty acid esters, polyoxyethylene sorbitol fatty acid esters, polyoxyethylene fatty acid esters, polyoxyethylene alkyl ethers, polyoxyethylene sterol ethers, polyoxyethylene-polypropoxy alkyl ethers, block polymers and cethyl ether, as well as polyoxyethylene castor oil or hydrogenated castor oil derivatives and polyglycerine fatty acid esters. Suitable non-ionic surfactants, include, but are not limited to various grades of Pluronic®, Poloxamer®, Span®, Tween®, Polysorbate®, Tyloxapol®, Emulphor® or Cremophor® and the like. The complementary surface active agents may also be of an ionic nature, such as bile duct agents, cholic acid or deoxycholic their salts and derivatives or free fatty acids, such as oleic acid, linoleic acid and others. Other ionic surface active agents are found among cationic lipids like C10-C24: alkylamines or alkanolamine and cationic cholesterol esters.

In the final FLiP, the oligonucleotide component is aggregated, associated or admixed with the lipid components via a lipophilic moiety. This aggregation, association or admixture may be at the surface of the final FLiP formulation. Alternatively, some integration of any of a portion or all of the lipophilic moiety may occur, extending into the lipid particle. Any lipophilic linker molecule that is able to bind oligonucleotides to lipids can be chosen. Examples include pyrrolidine and hydroxyprolinol.

The process for making the lipid particles comprises the steps of:

a) mixing a lipid components with one or several lipophile (e.g. cholesterol) conjugated oligonucleotides that may be chemically modified;
b) fractionating this mixture;
c) selecting the fraction with particles of 30-50 nm, preferably of about 40 nm in size.

Alternatively, the FLiP can be made by first isolating the lipid particles comprising triacylglycerol, phospholipids, glycerol and one or several lipid-binding proteins and then mixing the isolated particles with >2-fold molar excess of lipophile (e.g. cholesterol) conjugated oligonucleotide. The steps of fractionating and selecting the particles are deleted by this alternative process for making the FLiPs.

Other pharmacologically acceptable components can be added to the FLiPs when desired, such as antioxidants (exemplified by alpha-tocopherol) and solubilization adjuvants (exemplified by benzylalcohol).

Release Modifiers

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Polymers

Hydrophilic polymers suitable for use in the formulations of the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG (750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In one embodiment, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly (valeric acid), poly(lactide-co-caprolactone), polysaccharides, proteins, polyhyaluronic acids, polycyanoacrylates, and blends, mixtures, or copolymers thereof.

Surfactants

The above discussed formulation may also include one or more surfactants. Surfactants find wide application in formulations such as emulsions (including microemulsions) and liposomes. The use of surfactants in drug products, formulations and in emulsions has been reviewed (Rieger, in "Pharmaceutical Dosage Forms," Marcel Dekker, Inc., New York, N.Y., 1988, p. 285). Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Nonionic surfactants include, but are not limited to, nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

Anionic surfactants include, but are not limited to, carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

Cationic surfactants include, but are not limited to, quaternary ammonium salts and ethoxylated amines. The quaternary ammonium salts are the most used members of this class.

Amphoteric surfactants include, but are not limited to, acrylic acid derivatives, substituted alkylamides, N-alkylbetaines and phosphatides.

A surfactant may also be selected from any suitable aliphatic, cycloaliphatic or aromatic surfactant, including but not limited to biocompatible lysophosphatidylcholines (LPCs) of varying chain lengths (for example, from about C14 to about C20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Penetration Enhancers

In one embodiment, the formulations of the present invention employ various penetration enhancers to affect the efficient delivery of RNAi agents to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Pharmaceutical Compositions

In another aspect, the present invention provides pharmaceutically acceptable compositions which comprise a therapeutically-effective amount of one or more of the oligonucleotides described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In one embodiment, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In one embodiment, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Formulations for ocular administration can include mucomimetics such as hyaluronic acid, chondroitin sulfate, hydroxypropyl methylcellulose or poly (vinyl alcohol), preservatives such as sorbic acid, EDTA or benzylchronium chloride, and the usual quantities of diluents and/or carriers.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims.

As used herein, the term "nucleoside" refers to a compound comprising a heterocyclic base moiety and a sugar moiety. Nucleosides include, but are not limited to, naturally occurring nucleosides (as found in DNA and RNA), abasic nucleosides, modified nucleosides, and sugar-modified nucleosides. Nucleosides may be modified with any of a variety of substituents.

As used herein, "sugar moiety" means a natural (furanosyl), a modified sugar moiety or a sugar surrogate.

As used herein, "modified sugar moiety" means a chemically-modified furanosyl sugar or a non-furanosyl sugar moiety. Also, embraced by this term are furanosyl sugar analogs and derivatives including bicyclic sugars, tetrahydropyrans, morpholinos, 2'-modified sugars, 4'-modified sugars, 5'-modified sugars, and 4'-substituted sugars.

As used herein the term "sugar surrogate" refers to a structure that is capable of replacing the furanose ring of a naturally occurring nucleoside. In certain embodiments, sugar surrogates are non-furanose (or 4'-substituted furanose) rings or ring systems or open systems. Such structures include simple changes relative to the natural furanose ring, such as a six membered ring or may be more complicated as is the case with the non-ring system used in peptide nucleic acid. Sugar surrogates includes without limitation morpholinos and cyclohexenyls and cyclohexitols. In most nucleosides having a sugar surrogate group the heterocyclic base moiety is generally maintained to permit hybridization.

As used herein, "nucleobase" refers to the heterocyclic base portion of a nucleoside. Nucleobases may be naturally occurring or may be modified and therefore include, but are not limited to adenine, cytosine, guanidine, uracil, thymidine and analogues thereof. In certain embodiments, a nucleobase may comprise any atom or group of atoms capable of hydrogen bonding to a base of another nucleic acid. In certain embodiments, a nucleobase is a universal base. The phrases "2'-modification" and "2'-modified nucleotide" refer to a nucleotide unit having a sugar moiety, for example a ribosyl moiety, that is modified at the 2'-position such that the hydroxyl group of a natural riboside (2'-OH) is replaced by a substituent. 2'-Substituents include, but are not limited to: —F, —H, —$CH_3$, —$CH_2CH_3$, —$OCH_3$, —$OCH_2CH_3$, —$OCH_2CH_2OMe$, —$OCH_2C(=O)NHMe$, —$OCH_2$-(4'-C) (a so-called "LNA sugar modification"), or —$OCH_2CH_2$-(4'-C) (a so-called "ENA sugar modification"). For example, the phrases "2'-fluoro modification" and "2'-fluoro modified nucleotide" refer to a nucleotide unit having a sugar moiety, for example a ribosyl moiety, that is modified at the 2'-position such that the hydroxyl group (2'-OH) is replaced by a fluoro group (2'-F). U.S. Pat. Nos. 6,262,241, and 5,459,255 (both of which are incorporated by reference), are drawn to, inter alia, methods of synthesizing 2'-fluoro modified nucleotides and oligonucleotides.

The phrase "antisense strand" as used herein, refers to a polynucleotide that is substantially or 100% complementary to a target nucleic acid of interest. An antisense strand may comprise a polynucleotide that is RNA, DNA or chimeric RNA/DNA. For example, an antisense strand may be complementary, in whole or in part, to a molecule of messenger RNA, an RNA sequence that is not mRNA (e.g., tRNA, rRNA and hnRNA) or a sequence of DNA that is either coding or non-coding. The phrase "antisense strand" includes the antisense region of both polynucleotides that are formed from two separate strands, as well as unimolecular polynucleotides that are capable of forming hairpin structures. The terms "antisense strand" and "guide strand" are used interchangeably herein.

The phrase "sense strand" refers to a polynucleotide that has the same nucleotide sequence, in whole or in part, as a target nucleic acid such as a messenger RNA or a sequence of DNA. The sense strand is not incorporated into the functional riboprotein RISC. The terms "sense strand" and "passenger strand" are used interchangeably herein.

The term "duplex" includes a region of complementarity between two regions of two or more polynucleotides that comprise separate strands, such as a sense strand and an antisense strand, or between two regions of a single contiguous polynucleotide.

As used herein, "specifically hybridizable" and "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., a to t, a to u, c to g), or in any other manner that allows for the formation of stable duplexes. "Perfect complementarity" or 100% complementarity refers to the situation in which each nucleotide unit of one polynucleotide strand can hydrogen bond with each nucleotide unit of a second polynucleotide strand. Less than perfect complementarity refers to the situation in which some, but not all, nucleotide units of two strands can hydrogen bond with each other. "Substantial complementarity" refers to polynucleotide strands exhibiting 90% or greater complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 5 nucleotides.

The term "off-target" and the phrase "off-target effects" refer to any instance in which an RNAi agent against a given target causes an unintended affect by interacting either directly or indirectly with another mRNA sequence, a DNA sequence or a cellular protein or other moiety. For example, an "off-target effect" may occur when there is a simultaneous degradation of other transcripts due to partial homology or complementarity between that other transcript and the sense and/or antisense strand of a double-stranded RNAi agent.

The phrase "first 5' terminal nucleotide" includes first 5' terminal antisense nucleotides and first 5' terminal antisense nucleotides. "First 5' terminal antisense nucleotide" refers to the nucleotide of the antisense strand that is located at the 5' most position of that strand with respect to the bases of the antisense strand that have corresponding complementary bases on the sense strand. Thus, in a double stranded polynucleotide that is made of two separate strands, it refers to the 5' most base other than bases that are part of any 5' overhang on the antisense strand. When the first 5' terminal antisense nucleotide is part of a hairpin molecule, the term "terminal" refers to the 5' most relative position within the antisense region and thus is the 5" most nucleotide of the antisense region. The phrase "first 5" terminal sense nucleotide" is defined in reference to the sense nucleotide. In molecules comprising two separate strands, it refers to the nucleotide of the sense strand that is located at the 5' most position of that strand with respect to the bases of the sense strand that have corresponding complementary bases on the antisense strand. Thus, in a double stranded polynucleotide that is made of two separate strands, it is the 5' most base other than bases that are part of any 5' overhang on the sense strand.

In one embodiment, an siRNA compound is "sufficiently complementary" to a target RNA, e.g., a target mRNA, such that the siRNA compound silences production of protein encoded by the target mRNA. In another embodiment, the siRNA compound is "exactly complementary" to a target RNA, e.g., the target RNA and the siRNA compound anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, In one embodiment, the siRNA compound specifically discriminates a single-nucleotide difference. In this case, the siRNA compound only mediates RNAi if exact complementary is found in the region (e.g., within 7 nucleotides of) the single-nucleotide difference.

In one embodiment, oligonucleotides of the invention are prepared by connecting nucleosides with optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage, S. L. and Iyer, R. P., Tetrahedron, 49 No. 10, pp. 1925-1963 (1993); Beaucage, S. L. and Iyer, R. P., Tetrahedron, 49 No. 46, pp. 10441-10488 (1993); Beaucage, S. L. and Iyer, R. P., Tetrahedron, 48 No. 12, pp. 2223-2311 (1992).

In one embodiment, nucleosides having reactive phosphorus groups are provided that are useful for forming internucleoside linkages including for example phosphodiester and phosphorothioate internucleoside linkages. Such reactive phosphorus groups are known in the art and contain phosphorus atoms in $P^{III}$ or $P^{V}$ valence state including, but not limited to, phosphoramidite, H-phosphonate, phosphate triesters and phosphorus containing chiral auxiliaries. A preferred synthetic solid phase synthesis utilizes phosphoramidites ($P^{III}$ chemistry) as reactive phosphites. The intermediate phosphite compounds are subsequently oxidized to the Pv state using known methods to yield, in preferred embodiments, phosphodiester or phosphorothioate internucleotide linkages.

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, non-phosphorus containing internucleoside linking groups such as formacetyl and methyl eneimino, and neutral non-ionic internucleoside linking groups such as amide-3 (3'-CH$_2$—C(=O)—N(H)-5'), amide-4 (3'-CH$_2$—N(H)—C(=O)-5').

As used herein the term "alternating motif" refers to a an oligonucleotide comprising a contiguous sequence of linked monomer subunits wherein the monomer subunits have two different types of sugar groups that alternate for essentially the entire sequence of the oligonucleotide. Oligonucleotides having an alternating motif can be described by the formula: 5'-A(-L-B-L-A)n(-L-B)nn-3' where A and B are monomelic subunits that have different sugar groups, each L is an internucleoside linking group, n is from about 4 to about 12 and nn is 0 or 1. This permits alternating oligonucleotides from about 9 to about 26 monomer subunits in length. This length range is not meant to be limiting as longer and shorter oligonucleotides are also amenable to the present invention. In one embodiment, one of A and B is a 2'-modified nucleoside as provided herein.

As used herein, "type of modification" in reference to a nucleoside or a nucleoside of a "type" refers to the modification of a nucleoside and includes modified and unmodified nucleosides. Accordingly, unless otherwise indicated, a "nucleoside having a modification of a first type" may be an unmodified nucleoside.

As used herein, "type region" refers to a portion of an oligomeric compound wherein the nucleosides and internucleoside linkages within the region all comprise the same type of modifications; and the nucleosides and/or the internucleoside linkages of any neighboring portions include at least one different type of modification. As used herein the term "uniformly fully modified motif" refers to an oligonucleotide comprising a contiguous sequence of linked monomer subunits that each have the same type of sugar group. In one embodiment, the uniformly fully modified motif includes a contiguous sequence of nucleosides of the invention. In one embodiment, one or both of the 3' and 5'-ends of the contiguous sequence of the nucleosides provided herein, comprise terminal groups such as one or more unmodified nucleosides.

As used herein the term "hemimer motif" refers to an oligonucleotide having a short contiguous sequence of monomer subunits having one type of sugar group located at the 5' or the 3' end wherein the remainder of the monomer subunits have a different type of sugar group. In general, a hemimer is an oligomeric compound of uniform sugar groups further comprising a short region (1, 2, 3, 4 or about 5 monomelic subunits) having uniform but different sugar groups and located on either the 3' or the 5' end of the oligomeric compound. In one embodiment, the hemimer motif comprises a contiguous sequence of from about 10 to about 28 monomer subunits of one type with from 1 to 5 or from 2 to about 5 monomer subunits of a second type located at one of the termini. In one embodiment, a hemimer is a contiguous sequence of from about 8 to about 20 β-D-2'-deoxyribonucleosides having from 1-12 contiguous nucleosides of the invention located at one of the termini. In one embodiment, a hemimer is a contiguous sequence of from about 8 to about 20 β-D-2'-deoxyribonucleosides having from 1-5 contiguous nucleosides of the invention located at one of the termini. In one embodiment, a hemimer is a contiguous sequence of from about 12 to about 18 β-D-2'-deoxyribo-nucleosides having from 1-3 contiguous nucleosides of the invention located at one of the termini. In one embodiment, a hemimer is a contiguous sequence of from about 10 to about 14 β-D-2'-deoxyribonucleosides having from 1-3 contiguous nucleosides of the invention located at one of the termini.

As used herein the term "blockmer motif" refers to an oligonucleotide comprising an otherwise contiguous sequence of monomer subunits wherein the sugar groups of each monomer subunit is the same except for an interrupting internal block of contiguous monomer subunits having a different type of sugar group. A blockmer overlaps somewhat with a gapmer in the definition but typically only the monomer subunits in the block have non-naturally occurring sugar groups in a blockmer and only the monomer subunits in the external regions have non-naturally occurring sugar groups in a gapmer with the remainder of monomer subunits in the blockmer or gapmer being β-D-2'-deoxyribonucleosides or β-D-ribonucleosides. In one embodiment, blockmer oligonucleotides are provided herein wherein all of the monomer subunits comprise non-naturally occurring sugar groups.

As used herein the term "positionally modified motif" is meant to include an otherwise contiguous sequence of monomer subunits having one type of sugar group that is interrupted with two or more regions of from 1 to about 5 contiguous monomer subunits having another type of sugar group. Each of the two or more regions of from 1 to about 5 contiguous monomer subunits are independently uniformly modified with respect to the type of sugar group. In one embodiment, each of the two or more regions have the same type of sugar group. In one embodiment, each of the two or more regions have a different type of sugar group. In one embodiment, positionally modified oligonucleotides are provided comprising a sequence of from 8 to 20 β-D-2'- deoxyribonucleosides that further includes two or three regions of from 2 to about 5 contiguous nucleosides of the invention. Positionally modified oligonucleotides are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar groups of the external regions being different than the sugar groups of the internal region and wherein the sugar group of each monomer subunit within a particular region is the same. When the sugar groups of the external regions are the same the gapmer is a symmetric gapmer and when the sugar group used in the 5'-external region is different from the sugar group used in the 3'-external region, the gapmer is an asymmetric gapmer. In one embodiment, the external regions are small (each independently 1, 2, 3, 4 or about 5 monomer subunits) and the monomer subunits comprise non-naturally occurring sugar groups with the internal region comprising β-D-2'-deoxyribonucleosides. In one embodiment, the external regions each, independently, comprise from 1 to about 5 monomer subunits having non-naturally occurring sugar groups and the internal region comprises from 6 to 18 unmodified nucleosides. The internal region or the gap generally comprises β-D-2'-deoxyribo-nucleosides but can comprise non-naturally occurring sugar groups.

In one embodiment, the gapped oligonucleotides comprise an internal region of β-D-2'-deoxyribonucleosides with one of the external regions comprising nucleosides of the invention. In one embodiment, the gapped oligonucleotide comprise an internal region of β-D-2'-deoxyribonucleosides with both of the external regions comprising nucleosides of the invention. In one embodiment, the gapped oligonucleotide comprise an internal region of β-D-2'-deoxyribonucleosides with both of the external regions comprising nucleosides of the invention. In one embodiment, gapped oligonucleotides are provided herein wherein all of the monomer subunits comprise non-naturally occurring sugar groups. In one embodiment, gapped oligonucleotides are provided comprising one or two nucleosides of the invention at the 5'-end, two or three nucleosides of the invention at the 3'-end and an internal region of from 10 to 16 β-D-2'-deoxyribonucleosides. In one embodiment, gapped oligonucleotides are provided comprising one nucleoside of the invention at the 5'-end, two nucleosides of the invention at the 3'-end and an internal region of from 10 to 16 β-D-2'-deoxyribonucleosides. In one embodiment, gapped oligonucleotides are provided comprising two nucleosides of the invention at the 5'-end, two nucleosides of the invention at the 3'-end and an internal region of from 10 to 14 β-D-2'-deoxyribonucleosides. In one embodiment, gapped oligonucleotides are provided that are from about 10 to about 21 monomer subunits in length. In one embodiment, gapped oligonucleotides are provided that are from about 12 to about 16 monomer subunits in length. In one embodiment, gapped oligonucleotides are provided that are from about 12 to about 14 monomer subunits in length.

1. Certain 5'-Terminal Nucleosides

In certain embodiments, the 5'-terminal nucleoside of a modified oligonucleotides of the present invention comprises a phosphorous moiety at the 5'-end. In certain embodiments the 5'-terminal nucleoside comprises a 2'-modification. In certain such embodiments, the 2'-modification of the 5'-terminal nucleoside is a cationic modification. In certain embodiments, the 5'-terminal nucleoside comprises a 5'-modification. In certain embodiments, the 5'-terminal nucleoside comprises a 2'-modification and a 5'-modification. In certain embodiments, the 5'-terminal nucleoside is a nucleoside of Formula (2), (4), (6), (8), (10) or (12).

In certain embodiments, the 5'-terminal nucleoside is a 5'-stabilizing nucleoside. In certain embodiments, the modifications of the 5'-terminal nucleoside stabilize the 5'-phosphate. In certain embodiments, oligonucleotides comprising modifications of the 5'-terminal nucleoside are resistant to exonucleases. In certain embodiments, oligonucleotides comprising modifications of the 5'-terminal nucleoside have improved antisense properties. In certain such embodiments, oligonucleotides comprising modifications of the 5'-terminal nucleoside have improved association with members of the RISC pathway. In certain embodiments, oligonucleotides comprising modifications of the 5'-terminal nucleoside have improved affinity for Ago2.

In certain embodiments, the 5' terminal nucleoside is attached to a plurality of nucleosides by a modified linkage. In certain such embodiments, the 5' terminal nucleoside is a plurality of nucleosides by a phosphorothioate linkage.

2. Certain Alternating Regions

In certain embodiments, oligonucleotides of the present invention comprise one or more regions of alternating modifications. In certain embodiments, oligonucleotides comprise one or more regions of alternating nucleoside modifications. In certain embodiments, oligonucleotides comprise one or more regions of alternating linkage modifications. In certain embodiments, oligonucleotides comprise one or more regions of alternating nucleoside and linkage modifications.

In certain embodiments, oligonucleotides of the present invention comprise one or more regions of alternating 2'-F modified nucleosides and 2'-OMe modified nucleosides. In certain such embodiments, such regions of alternating 2'F modified and 2'OMe modified nucleosides also comprise alternating linkages. In certain such embodiments, the linkages at the 3' end of the 2'-F modified nucleosides are phosphorothioate linkages. In certain such embodiments, the linkages at the 3' end of the 2'OMe nucleosides are phosphodiester linkages. In certain embodiments, such alternating regions are:

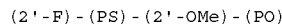

In certain embodiments, oligomeric compounds comprise 2, 3, 4, 5, 6, 7, 8, 9, 10, or 11 such alternating regions. Such regions may be contiguous or may be interrupted by differently modified nucleosides or linkages.

In certain embodiments, one or more alternating regions in an alternating motif include more than a single nucleoside of a type. For example, oligomeric compounds of the present invention may include one or more regions of any of the following nucleoside motifs:

AABBAA;

ABBABB;

AABAAB;

ABBABAABB;

```
ABABAA;

AABABAB;

ABABAA;

ABBAABBABABAA;

BABBAABBABABAA;
or

ABABBAABBABABAA;
``` wherein A is a nucleoside of a first type and B is a nucleoside of a second type. In certain embodiments, A and B are each selected from 2'-F, 2'-OMe, BNA, DNA, MOE, and formula (2), (4), (6), (8), (10) or (12).

In certain embodiments, A is DNA. In certain embodiments, B is 4'-CH$_2$O-2'-BNA. In certain embodiments, A is DNA and B is 4'-CH$_2$O-2'-BNA. In certain embodiments A is 4'-CH$_2$O-2'-BNA. In certain embodiments, B is DNA. In certain embodiments A is 4'-CH$_2$O-2'-BNA and B is DNA. In certain embodiments, A is 2'-F. In certain embodiments, B is 2'-OMe. In certain embodiments, A is 2'-F and B is 2'-OMe. In certain embodiments, A is 2'-OMe. In certain embodiments, B is 2'-F. In certain embodiments, A is 2'-OMe and B is 2'-F. In certain embodiments, A is DNA and B is 2'-OMe. In certain embodiments, A is 2'-OMe and B is DNA.

In certain embodiments, oligomeric compounds having such an alternating motif also comprise a 5' terminal nucleoside comprising a phosphate stabilizing modification. In certain embodiments, oligomeric compounds having such an alternating motif also comprise a 5' terminal nucleoside comprising a 2'-cationic modification. In certain embodiments, oligomeric compounds having such an alternating motif also comprise a 5' terminal nucleoside of formula (2), (4), (6), (8), (10) or (12).

3. Two-Two-Three Motifs

In certain embodiments, oligonucleotides of the present invention comprise a region having a 2-2-3 motif. Such regions comprises the following motif:

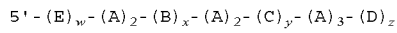

wherein: A is a first type of modified nucleoside;

B, C, D, and E are nucleosides that are differently modified than A, however, B, C, D, and E may have the same or different modifications as one another;

w and z are from 0 to 15;

x and y are from 1 to 15.

In certain embodiments, A is a 2'-OMe modified nucleoside. In certain embodiments, B, C, D, and E are all 2'-F modified nucleosides. In certain embodiments, A is a 2'-OMe modified nucleoside and B, C, D, and E are all 2'-F modified nucleosides.

In certain embodiments, the linkages of a 2-2-3 motif are all modified linkages. In certain embodiments, the linkages are all phosphorothioate linkages. In certain embodiments, the linkages at the 3'-end of each modification of the first type are phosphodiester.

In certain embodiments, Z is 0. In such embodiments, the region of three nucleosides of the first type are at the 3'-end of the oligonucleotide. In certain embodiments, such region is at the 3'-end of the oligomeric compound, with no additional groups attached to the 3' end of the region of three nucleosides of the first type. In certain embodiments, an oligomeric compound comprising an oligonucleotide where Z is 0, may comprise a terminal group attached to the 3'-terminal nucleoside. Such terminal groups may include additional nucleosides. Such additional nucleosides are typically non-hybridizing nucleosides.

In certain embodiments, Z is 1-3. In certain embodiments, Z is 2. In certain embodiments, the nucleosides of Z are 2'-MOE nucleosides. In certain embodiments, Z represents non-hybridizing nucleosides. To avoid confusion, it is noted that such non-hybridizing nucleosides might also be described as a 3'-terminal group with Z=0.

3. Combinations of Motifs

It is to be understood, that certain of the above described motifs and modifications may be combined. Since a motif may comprises only a few nucleosides, a particular oligonucleotide may comprise two or more motifs. By way of non-limiting example, in certain embodiments, oligomeric compounds may have nucleoside motifs as described in the table below. In the table below, the term "None" indicates that a particular feature is not present in the oligonucleotide. For example, "None" in the column labeled "5' motif/modification" indicates that the 5' end of the oligonucleotide comprises the first nucleoside of the central motif.

| 5' motif/modification | Central Motif | 3'-motif |
|---|---|---|
| Formula (2), (4), (6), (8), (10) or (12) | Alternating | 2 MOE nucleosides |
| Formula (2), (4), (6), (8), (10) or (12) | 2-2-3 motif | 2 MOE nucleosides |
| Formula (2), (4), (6), (8), (10) or (12) | Uniform | 2 MOE nucleosides |
| Formula (2), (4), (6), (8), (10) or (12) | Alternating | 2 MOE nucleosides |
| Formula (2), (4), (6), (8), (10) or (12) | Alternating | 2 MOE A's |
| Formula (2), (4), (6), (8), (10) or (12) | 2-2-3 motif | 2 MOE A's |
| Formula (2), (4), (6), (8), (10) or (12) | Uniform | 2 MOE A's |
| Formula (2), (4), (6), (8), (10) or (12) | Alternating | 2 MOE U's |
| Formula (2), (4), (6), (8), (10) or (12) | 2-2-3 motif | 2 MOE U's |
| Formula (2), (4), (6), (8), (10) or (12) | Uniform | 2 MOE U's |
| None | Alternating | 2 MOE nucleosides |
| None | 2-2-3 motif | 2 MOE nucleosides |
| None | Uniform | 2 MOE nucleosides |
| Any of Formula (1)-(3), (2A)-(4A), (1-a)-(1-d), (2-a)-(2-c), (3-a)-(3-c), and (4-a)-(4-f) | Alternating | 2 MOE nucleosides |
| Any of Formula (1)-(3), (2A)-(4A), (1-a)-(1-d), (2-a)-(2-c), (3-a)-(3-c), and (4-a)-(4-f) | 2-2-3 motif | 2 MOE nucleosides |
| Any of Formula (1)-(3), (2A)-(4A), (1-a)-(1-d), (2-a)-(2-c), (3-a)-(3-c), and (4-a)-(4-f) | Uniform | 2 MOE nucleosides |
| Any of Formula (1)-(3), (2A)-(4A), (1-a)-(1-d), (2-a)-(2-c), (3-a)-(3-c), and (4-a)-(4-f) | Alternating | 2 MOE nucleosides |
| Any of Formula (1)-(3), (2A)-(4A), (1-a)-(1-d), (2-a)-(2-c), (3-a)-(3-c), and (4-a)-(4-f) | Alternating | 2 MOE A's |
| Any of Formula (1)-(3), (2A)-(4A), (1-a)-(1-d), (2-a)-(2-c), (3-a)-(3-c), and (4-a)-(4-f) | 2-2-3 motif | 2 MOE A's |
| Any of Formula (1)-(3), (2A)-(4A), (1-a)-(1-d), (2-a)-(2-c), (3-a)-(3-c), and (4-a)-(4-f) | Uniform | 2 MOE A's |
| Any of Formula (1)-(3), (2A)-(4A), (1-a)-(1-d), (2-a)-(2-c), (3-a)-(3-c), and (4-a)-(4-f) | Alternating | 2 MOE U's |

-continued

| 5' motif/modification | Central Motif | 3'-motif |
|---|---|---|
| Any of Formula (1)-(3), (2A)-(4A), (1-a)-(1-d), (2-a)-(2-c), (3-a)-(3-c), and (4-a)-(4-f) | 2-2-3 motif | 2 MOE U's |
| Any of Formula (1)-(3), (2A)-(4A), (1-a)-(1-d), (2-a)-(2-c), (3-a)-(3-c), and (4-a)-(4-f) | Uniform | 2 MOE U's |
| None | Alternating | 2 MOE nucleosides |
| None | 2-2-3 motif | 2 MOE nucleosides |
| None | Uniform | 2 MOE nucleosides |

Oligomeric compounds having any of the various nucleoside motifs described herein, may have any linkage motif. For example, the oligomeric compounds, including but not limited to those described in the above table, may have a linkage motif selected from non-limiting the table below:

| 5' most linkage | Central region | 3'-region |
|---|---|---|
| PS | Alternating PO/PS | 6 PS |
| PS | Alternating PO/PS | 7 PS |
| PS | Alternating PO/PS | 8 PS |

As is apparent from the above, non-limiting tables, the lengths of the regions defined by a nucleoside motif and that of a linkage motif need not be the same. For example, the 3' region in the nucleoside motif table above is 2 nucleosides, while the 3'-region of the linkage motif table above is 6-8 nucleosides. Combining the tables results in an oligonucleotide having two 3'-terminal MOE nucleosides and six to eight 3'-terminal phosphorothioate linkages (so some of the linkages in the central region of the nucleoside motif are phosphorothioate as well). To further illustrate, and not to limit in any way, nucleoside motifs and sequence motifs are combined to show five non-limiting examples in the table below. The first column of the table lists nucleosides and linkages by position from N1 (the first nucleoside at the 5'-end) to N20 (the $20^{th}$ position from the 5'-end). In certain embodiments, oligonucleotides of the present invention are longer than 20 nucleosides (the table is merely exemplary). Certain positions in the table recite the nucleoside or linkage "none" indicating that the oligonucleotide has no nucleoside at that position.

| Pos | A | B | C | D | E | F |
|---|---|---|---|---|---|---|
| N1 | Formula (2), (4), (6), (8), (10) or (12) | Formula (2), (4), (6), (8), (10) or (12) | Formula (2), (4), (6), (8), (10) or (12) | Formula (2), (4), (6), (8), (10) or (12) | Formula (2), (4), (6), (8), (10) or (12) | 2'-F |
| L1 | PS | PS | PS | PS | PO | PO |
| N2 | 2'-F | 2'-F | 2'-F | 2'-OMe | MOE | 2'-OMe |
| L2 | PS | PS | PS | PO | PS | PO |
| N3 | 2'-OMe | 2'-F | 2'-F | 2'-F | 2'-F | 2'-F |
| L3 | PO | PS | PS | PS | PS | PS |
| N4 | 2'-F | 2'-F | 2'-F | 2'-OMe | 2'-F | 2'-OMe |
| L4 | PS | PS | PS | PO | PS | PO |
| N5 | 2'-OMe | 2'-F | 2'-F | 2'-F | 2'-OMe | 2'-F |
| L5 | PO | PS | PS | PS | PO | PS |
| N6 | 2'-F | 2'-OMe | 2'-F | 2'-OMe | 2'-OMe | 2'-OMe |
| L6 | PS | PO | PS | PO | PO | PO |
| N7 | 2'-OMe | 2'-OMe | 2'-F | 2'-F | 2'-OMe | 2'-F |
| L7 | PO | PO | PS | PS | PO | PS |
| N8 | 2'-F | 2'-F | 2'-F | 2'-OMe | 2'-F | 2'-OMe |
| L8 | PS | PS | PS | PO | PS | PO |
| N9 | 2'-OMe | 2'-F | 2'-F | 2'-F | 2'-F | 2'-F |
| L9 | PO | PS | PS | PS | PS | PS |
| N10 | 2'-F | 2'-OMe | 2'-F | 2'-OMe | 2'-OMe | 2'-OMe |
| L10 | PS | PO | PS | PO | PO | PO |
| N11 | 2'-OMe | 2'-OMe | 2'-F | 2'-F | 2'OMe | 2'-F |
| L11 | PO | PO | PS | PS | PO | PS |
| N12 | 2'-F | 2'-F | 2'-F | 2'-F | 2'-F | 2'-OMe |
| L12 | PS | PS | PS | PO | PS | PO |
| N13 | 2'-OMe | 2'-F | 2'-F | 2'-F | 2'-F | 2'-F |
| L13 | PO | PS | PS | PS | PS | PS |
| N14 | 2'-F | 2'-OMe | 2'-F | 2'-F | 2'-F | 2'-F |
| L14 | PS | PS | PS | PS | PS | PS |
| N15 | 2'-OMe | 2'OMe | 2'-F | 2'-F | 2'-MOE | 2'-F |
| L15 | PS | PS | PS | PS | PS | PS |
| N16 | 2'-F | 2'OMe | 2'-F | 2'-F | 2'-MOE | 2'-F |
| L16 | PS | PS | PS | PS | PS | PS |
| N17 | 2'-OMe | 2'-MOE U | 2'-F | 2'-F | 2'-MOE | 2'-F |
| L17 | PS | PS | PS | PS | None | PS |
| N18 | 2'-F | 2'-MOE U | 2'-F | 2'-OMe | None | MOE A |
| L18 | PS | None | PS | PS | None | PS |
| N19 | 2'-MOE U | None | 2'-MOE U | 2'-MOE A | None | MOE U |
| L19 | PS | None | PS | PS | None | None |
| N20 | 2'-MOE U | None | 2'-MOE U | 2'-MOE A | None | None |

In the above, non-limiting examples:

Column A represent an oligomeric compound consisting of 20 linked nucleosides, wherein the oligomeric compound comprises: a modified 5'-terminal nucleoside of Formula (2), (4), (6), (8), (10) or (12); a region of alternating nucleosides; a region of alternating linkages; two 3'-terminal MOE nucleosides, each of which comprises a uracil base; and a region of six phosphorothioate linkages at the 3'-end.

Column B represents an oligomeric compound consisting of 18 linked nucleosides, wherein the oligomeric compound comprises: a modified 5'-terminal nucleoside of Formula (2), (4), (6), (8), (10) or (12); a 2-2-3 motif wherein the modified nucleoside of the 2-2-3 motif are 2'O-Me and the remaining nucleosides are all 2'-F; two 3'-terminal MOE nucleosides, each of which comprises a uracil base; and a region of six phosphorothioate linkages at the 3'-end.

Column C represents an oligomeric compound consisting of 20 linked nucleosides, wherein the oligomeric compound comprises: a modified 5'-terminal nucleoside of Formula (2), (4), (6), (8), (10) or (12); a region of uniformly modified 2'-F nucleosides; two 3'-terminal MOE nucleosides, each of which comprises a uracil base; and wherein each internucleoside linkage is a phosphorothioate linkage.

Column D represents an oligomeric compound consisting of 20 linked nucleosides, wherein the oligomeric compound comprises: a modified 5'-terminal nucleoside of Formula (2), (4), (6), (8), (10) or (12); a region of alternating 2'-OMe/2'-F nucleosides; a region of uniform 2'F nucleosides; a region of alternating phosphorothioate/phosphodiester linkages; two 3'-terminal MOE nucleosides, each of which comprises an adenine base; and a region of six phosphorothioate linkages at the 3'-end.

Column E represents an oligomeric compound consisting of 17 linked nucleosides, wherein the oligomeric compound comprises: a modified 5'-terminal nucleoside of Formula (2), (4), (6), (8), (10) or (12); a 2-2-3 motif wherein the modified nucleoside of the 2-2-3 motif are 2'F and the remaining nucleosides are all 2'-OMe; three 3'-terminal MOE nucleosides.

Column F represents an oligomeric compound consisting of 18 linked nucleosides, wherein the oligomeric compound comprises: a region of alternating 2'-OMe/2'-F nucleosides; a region of uniform 2'F nucleosides; a region of alternating phosphorothioate/phosphodiester linkages; two 3'-terminal MOE nucleosides, one of which comprises a uracil base and the other of which comprises an adenine base; and a region of six phosphorothioate linkages at the 3'-end.

| Pos | A | B | C | D | E | F |
|---|---|---|---|---|---|---|
| N1 | Any of Formula (1)-(3), (2A)-(4A), (1-a)-(1-d), (2-a)-(2-c), (3-a)-(3-c), and (4-a)-(4-f) | Any of Formula (1)-(3), (2A)-(4A), (1-a)-(1-d), (2-a)-(2-c), (3-a)-(3-c), and (4-a)-(4-f) | Any of Formula (1)-(3), (2A)-(4A), (1-a)-(1-d), (2-a)-(2-c), (3-a)-(3-c), and (4-a)-(4-f) | Any of Formula (1)-(3), (2A)-(4A), (1-a)-(1-d), (2-a)-(2-c), (3-a)-(3-c), and (4-a)-(4-f) | Any of Formula (1)-(3), (2A)-(4A), (1-a)-(1-d), (2-a)-(2-c), (3-a)-(3-c), and (4-a)-(4-f) | 2'-F |
| L1 | PS | PS | PS | PS | PO | PO |
| N2 | 2'-F | 2'-F | 2'-F | 2'-OMe | MOE | 2'-OMe |
| L2 | PS | PS | PS | PO | PS | PO |
| N3 | 2'-OMe | 2'-F | 2'-F | 2'-F | 2'-F | 2'-F |
| L3 | PO | PS | PS | PS | PS | PS |
| N4 | 2'-F | 2'-F | 2'-F | 2'-OMe | 2'-F | 2'-OMe |
| L4 | PS | PS | PS | PO | PS | PO |
| N5 | 2'-OMe | 2'-F | 2'-F | 2'-F | 2'-OMe | 2'-F |
| L5 | PO | PS | PS | PS | PO | PS |
| N6 | 2'-F | 2'-OMe | 2'-F | 2'-OMe | 2'-OMe | 2'-OMe |
| L6 | PS | PO | PS | PO | PO | PO |
| N7 | 2'-OMe | 2'-OMe | 2'-F | 2'-F | 2'-OMe | 2'-F |
| L7 | PO | PO | PS | PS | PO | PS |
| N8 | 2'-F | 2'-F | 2'-F | 2'-OMe | 2'-F | 2'-OMe |
| L8 | PS | PS | PS | PO | PS | PO |
| N9 | 2'-OMe | 2'-F | 2'-F | 2'-F | 2'-F | 2'-F |
| L9 | PO | PS | PS | PS | PS | PS |
| N10 | 2'-F | 2'-OMe | 2'-F | 2'-OMe | 2'-OMe | 2'-OMe |
| L10 | PS | PO | PS | PO | PO | PO |
| N11 | 2'-OMe | 2'-OMe | 2'-F | 2'-F | 2'OMe | 2'-F |
| L11 | PO | PO | PS | PS | PO | PS |
| N12 | 2'-F | 2'-F | 2'-F | 2'-F | 2'-F | 2'-OMe |
| L12 | PS | PS | PS | PO | PS | PO |
| N13 | 2'-OMe | 2'-F | 2'-F | 2'-F | 2'-F | 2'-F |
| L13 | PO | PS | PS | PS | PS | PS |
| N14 | 2'-F | 2'-OMe | 2'-F | 2'-F | 2'-F | 2'-F |
| L14 | PS | PS | PS | PS | PS | PS |
| N15 | 2'-OMe | 2'OMe | 2'-F | 2'-F | 2'-MOE | 2'-F |
| L15 | PS | PS | PS | PS | PS | PS |
| N16 | 2'-F | 2'OMe | 2'-F | 2'-F | 2'-MOE | 2'-F |
| L16 | PS | PS | PS | PS | PS | PS |
| N17 | 2'-OMe | 2'-MOE U | 2'-F | 2'-F | 2'-MOE | 2'-F |
| L17 | PS | PS | PS | PS | None | PS |
| N18 | 2'-F | 2'-MOE U | 2'-F | 2'-OMe | None | MOE A |
| L18 | PS | None | PS | PS | None | PS |
| N19 | 2'-MOE U | None | 2'-MOE U | 2'-MOE A | None | MOE U |
| L19 | PS | None | PS | PS | None | None |
| N20 | 2'-MOE U | None | 2'-MOE U | 2'-MOE A | None | None |

In the above table, non-limiting examples:

Column A represent an oligomeric compound consisting of 20 linked nucleosides, wherein the oligomeric compound comprises: a modified 5'-terminal nucleoside of any one of Any of Formula (1)-(3), (2A)-(4A), (1-a)-(1-d), (2-a)-(2-c), (3-a)-(3-c), and (4-a)-(4-f); a region of alternating nucleosides; a region of alternating linkages; two 3'-terminal MOE nucleosides, each of which comprises a uracil base; and a region of six phosphorothioate linkages at the 3'-end.

Column B represents an oligomeric compound consisting of 18 linked nucleosides, wherein the oligomeric compound comprises: a modified 5'-terminal nucleoside of any one of Any of Formula (1)-(3), (2A)-(4A), (1-a)-(1-d), (2-a)-(2-c), (3-a)-(3-c), and (4-a)-(4-f); a 2-2-3 motif wherein the modified nucleoside of the 2-2-3 motif are 2'O-Me and the remaining nucleosides are all 2'-F; two 3'-terminal MOE nucleosides, each of which comprises a uracil base; and a region of six phosphorothioate linkages at the 3'-end.

Column C represents an oligomeric compound consisting of 20 linked nucleosides, wherein the oligomeric compound comprises: a modified 5'-terminal nucleoside of any one of Any of Formula (1)-(3), (2A)-(4A), (1-a)-(1-d), (2-a)-(2-c), (3-a)-(3-c), and (4-a)-(4-f); a region of uniformly modified 2'-F nucleosides; two 3'-terminal MOE nucleosides, each of which comprises a uracil base; and wherein each internucleoside linkage is a phosphorothioate linkage.

Column D represents an oligomeric compound consisting of 20 linked nucleosides, wherein the oligomeric compound comprises: a modified 5'-terminal nucleoside of any one of Any of Formula (1)-(3), (2A)-(4A), (1-a)-(1-d), (2-a)-(2-c), (3-a)-(3-c), and (4-a)-(4-f); a region of alternating 2'-OMe/2'-F nucleosides; a region of uniform 2'F nucleosides; a region of alternating phosphorothioate/phosphodiester linkages; two 3'-terminal MOE nucleosides, each of which comprises an adenine base; and a region of six phosphorothioate linkages at the 3'-end.

Column E represents an oligomeric compound consisting of 17 linked nucleosides, wherein the oligomeric compound comprises: a modified 5'-terminal nucleoside of any one of Any of Formula (1)-(3), (2A)-(4A), (1-a)-(1-d), (2-a)-(2-c), (3-a)-(3-c), and (4-a)-(4-f); a 2-2-3 motif wherein the modified nucleoside of the 2-2-3 motif are 2'F and the remaining nucleosides are all 2'-OMe; three 3'-terminal MOE nucleosides.

Column F represents an oligomeric compound consisting of 18 linked nucleosides, wherein the oligomeric compound comprises: a region of alternating 2'-OMe/2'-F nucleosides; a region of uniform 2'F nucleosides; a region of alternating phosphorothioate/phosphodiester linkages; two 3'-terminal MOE nucleosides, one of which comprises a uracil base and the other of which comprises an adenine base; and a region of six phosphorothioate linkages at the 3'-end.

The above examples are provided solely to illustrate how the described motifs may be used in combination and are not intended to limit the invention to the particular combinations or the particular modifications used in illustrating the combinations. Further, specific examples herein, including, but not limited to those in the above table are intended to encompass more generic embodiments. For example, column A in the above table exemplifies a region of alternating 2'-OMe and 2'-F nucleosides. Thus, that same disclosure also exemplifies a region of alternating different 2'-modifications. It also exemplifies a region of alternating 2'-O-alkyl and 2'-halogen nucleosides. It also exemplifies a region of alternating differently modified nucleosides. All of the examples throughout this specification contemplate such generic interpretation.

It is also noted that the lengths of oligomeric compounds, such as those exemplified in the above tables, can be easily manipulated by lengthening or shortening one or more of the described regions, without disrupting the motif.

The phrase "pharmaceutically acceptable carrier or diluent" includes compositions that facilitate the introduction of nucleic acid therapeutics such as siRNA, dsRNA, dsDNA, shRNA, microRNA, antimicroRNA, antagomir, antimir, antisense, aptamer or dsRNA/DNA hybrids into a cell and includes but is not limited to solvents or dispersants, coatings, anti-infective agents, isotonic agents, and agents that mediate absorption time or release of the inventive polynucleotides and double stranded polynucleotides. The phrase "pharmaceutically acceptable" includes approval by a regulatory agency of a government, for example, the U.S. federal government, a non-U.S. government, or a U.S. state government, or inclusion in a listing in the U.S. Pharmacopeia or any other generally recognized pharmacopeia for use in animals, including in humans.

The terms "silence" and "inhibit the expression of" and related terms and phrases, refer to the at least partial suppression of the expression of a gene targeted by an siRNA or siNA, as manifested by a reduction of the amount of mRNA transcribed from the target gene which may be isolated from a first cell or group of cells in which the target gene is transcribed and which has or have been treated such that the expression of the target gene is inhibited, as compared to a second cell or group of cells substantially identical to the first cell or group of cells but which has or have not been so treated (i.e., control cells).

The term "halo" refers to any radical of fluorine, chlorine, bromine or iodine.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substitutent groups.

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as (C1-C6)alkanoyl (e.g., formyl, acetyl, propionyl, butyryl, valeryl, caproyl, t-butylacetyl, etc.), (C3-Ce)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The term "alkyl" refers to a saturatednon-aromatic hydrocarbon chain. Alkyls may be a straight chain or branched chain and contain containing the indicated number of carbon atoms For example, $C_1$-$C_{10}$ indicates that the group may have from 1 to 10 (inclusive) carbon atoms in it.

The term "alkenyl" refers to a non-aromatic hydrocarbon chain containing at least one carbon-carbon double bond. Alkenyls may be a straight chain or branched chain, containing the indicated number of carbon atoms For example, $C_2$-$C_{10}$ indicates that the group may have from 2 to 10 (inclusive) carbon atoms in it.

The term "alkynyl" refers to a non-aromatic hydrocarbon chain containing at least one carbon-carbon triple bond. Alkynyls may be a straight chain or branched chain, containing the indicated number of carbon atoms For example, $C_2$-$C_{10}$ indicates that the group may have from 2 to 10 (inclusive) carbon atoms in it.

The term "heteroalkyl" refers to a group comprising an alkyl and at least one heteroatom. In certain such embodiments, the heteroatom is selected from O, S, and N. Certain heteroalkyls are acylalkyls, in which one or more heteroatoms are within the alkyl chain. Certain heteroalkyls are non-acylalkyl heteroalkyls, in which the heteroatom is not within the alkyl chain. Examples of heteroalkyls include, but are not limited to: $CH_3C(=O)CH_2$—, $CH_3OCH_2CH_2$—, $CH_3NHCH_2$—, $CH_3SHCH_2$—, and the like. The terms "heteroalkenyl" and "heteroalkynyl" refer to groups comprising an alkenyl or alkynyl receptively and at least heteroatom.

The term "alkoxy" refers to an —O-alkyl radical. The term "alkylene" refers to a divalent alkyl (i.e., —R—). The term "alkylenedioxo" refers to a divalent species of the structure —O—R—O—, in which R represents an alkylene. The term "aminoalkyl" refers to an alkyl substituted with an amino. The term "mercapto" refers to an —SH radical. The term "thioalkoxy" refers to an —S-alkyl radical.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" or "heterocyclic" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an identified group at any atom of that group. Suitable substituents include, without limitation, halo, hydroxy, oxo, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, ureido or conjugate groups.

In many cases, protecting groups are used during preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative hydroxyl protecting groups, for example, are disclosed by Beaucage et al. (*Tetrahedron* 1992, 48, 2223-2311). Further hydroxyl protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y, 1991.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Amino-protecting groups stable to acid treatment are selectively removed with base treatment, and are used to make reactive amino groups selectively available for substitution. Examples of such groups are the Fmoc (E. Atherton and R. C. Sheppard in *The Peptides*, S. Udenfriend, J. Meienhofer, Eds., Academic Press, Orlando, 1987, volume 9, p. 1) and various substituted sulfonylethyl carbamates exemplified by the Nsc group (Samukov et al., *Tetrahedron Lett.* 1994, 35, 7821; Verhart and Tesser, *Rec. Tray. Chim. Pays-Bas* 1987, 107, 621).

Additional amino-protecting groups include, but are not limited to, carbamate protecting groups, such as 2-trimethylsilylethoxycarbonyl (Teoc), 1-methyl-1-(4-biphenyl)-ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Equivalents of these amino-protecting groups are also encompassed by the compounds and methods of the present invention.

Evaluation of Candidate Oligonucleotides

One can evaluate a candidate oligonucleotide, e.g., a modified RNA, for a selected property by exposing the agent or modified molecule and a control molecule to the appropriate conditions and evaluating for the presence of the selected property. For example, resistance to a degradent can be evaluated as follows. A candidate modified oligonucleotide (and a control molecule, usually the unmodified form) can be exposed to degradative conditions, e.g., exposed to a milieu, which includes a degradative agent, e.g., a nuclease. E.g., one can use a biological sample, e.g., one that is similar to a milieu, which might be encountered, in therapeutic use, e.g., blood or a cellular fraction, e.g., a cell-free homogenate or disrupted cells. The candidate and control could then be evaluated for resistance to degradation by any of a number of approaches. For example, the candidate and control could be labeled prior to exposure, with, e.g., a radioactive or enzymatic label, or a fluorescent label, such as Cy3 or Cy5. Control and oligonucleotide can be incubated with the degradative agent, and optionally a control, e.g., an inactivated, e.g., heat inactivated, degradative agent. A physical parameter, e.g., size, of the modified and control molecules are then determined. They can be determined by a physical method, e.g., by polyacrylamide gel electrophoresis or a sizing column, to assess whether the molecule has maintained its original length, or assessed functionally. Alternatively, Northern blot analysis can be used to assay the length of an unlabeled modified molecule.

A functional assay can also be used to evaluate the candidate agent. A functional assay can be applied initially or after an earlier non-functional assay, (e.g., assay for resistance to degradation) to determine if the modification alters the ability of the molecule to silence gene expression. For example, a cell, e.g., a mammalian cell, such as a mouse or human cell, can be co-transfected with a plasmid expressing a fluorescent protein, e.g., GFP, and a candidate oligonucleotide homologous to the transcript encoding the fluorescent protein (see, e.g., WO 00/44914). For example, a modified oligonucleotide homologous to the GFP mRNA can be assayed for the ability to inhibit GFP expression by monitoring for a decrease in cell fluorescence, as compared to a control cell, in which the transfection did not include the candidate dsRNA, e.g., controls with no agent added and/or controls with a non-modified RNA added. Efficacy of the candidate agent on gene expression can be assessed by comparing cell fluorescence in the presence of the modified oligonucleotide and unmodified dssiRNA compounds.

In an alternative functional assay, a candidate oligonucleotide compound homologous to an endogenous mouse gene, for example, a maternally expressed gene, such as c-mos, can be injected into an immature mouse oocyte to assess the ability of the agent to inhibit gene expression in vivo (see, e.g., WO 01/36646). A phenotype of the oocyte, e.g., the ability to maintain arrest in metaphase II, can be monitored as an indicator that the agent is inhibiting expression. For example, cleavage of c-mos mRNA by an oligonucleotide would cause the oocyte to exit metaphase arrest and initiate parthenogenetic development (Colledge et al. Nature 370: 65-68, 1994; Hashimoto et al. Nature, 370:68-71, 1994). The effect of the oligonucleotide on target RNA levels can be verified by Northern blot to assay for a decrease in the level of target mRNA, or by Western blot to assay for a decrease in the level of target protein, as compared to a negative control. Controls can include cells in which with no agent is added.

Kits

In certain other aspects, the invention provides kits that include a suitable container containing a pharmaceutical formulation of an oligonucleotide. In one embodiment the individual components of the pharmaceutical formulation may be provided in one container. Alternatively, it may be desirable to provide the components of the pharmaceutical formulation separately in two or more containers, e.g., one container for an oligonucleotide preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

EXAMPLES

The invention now being generally described, it will be more readily understood by reference to the following examples which are included merely for purposes of illustration of certain aspects and embodiments of the present invention, and are not intended to limit the invention.

Synthetic Methods and Examples

The compounds of the inventions may be prepared by any process known to be applicable to the preparation of chemically-related compounds. Suitable processes for making certain intermediates include, for example, those references listed below which are herein incorporated by reference.

Necessary starting materials may be obtained by standard procedures of organic chemistry. Alternatively necessary starting materials are obtainable by analogous procedures to those illustrated which are within the ordinary skill of a chemist. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

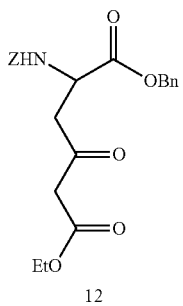

*J. Org. Chem.* 1997. 02 8242-8246

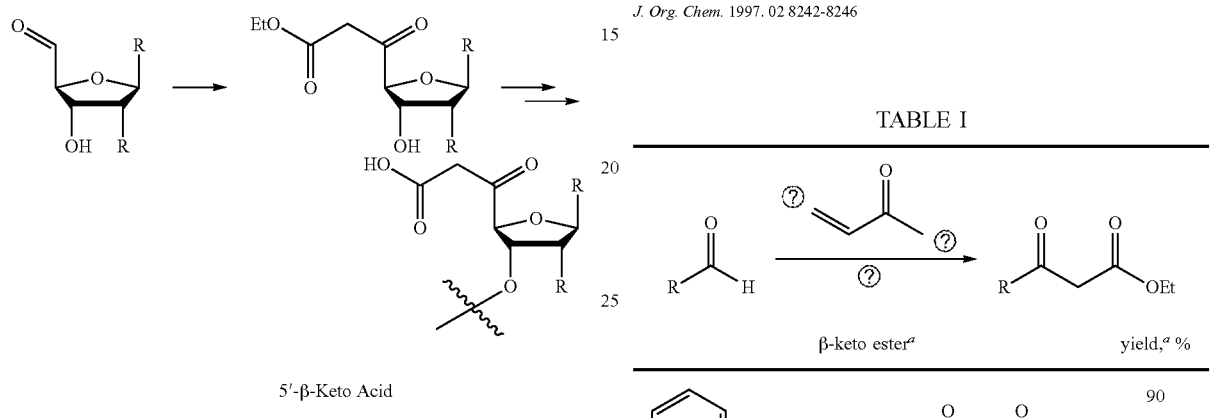

5'-β-Keto Acid

Scheme 3

TABLE I

| β-keto ester[a] | yield,[a] % |
|---|---|
| | 90 |
| | 75 |

*J. Org. Chem.*, Vol. 54, No. 14, 1989 3259

Synthesis of Non-Phosphorous Containing Phosphate Mimics

Example 1. Synthesis of 559-5

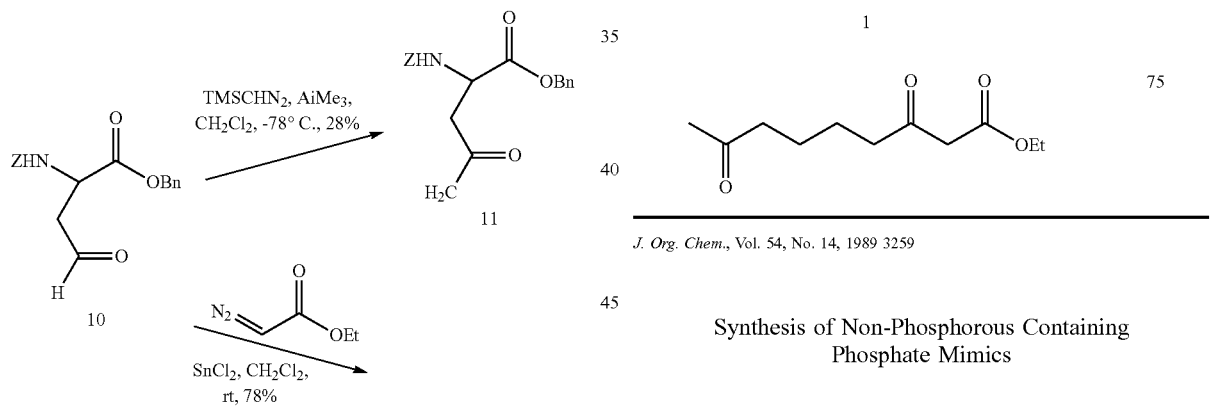

Scheme 1

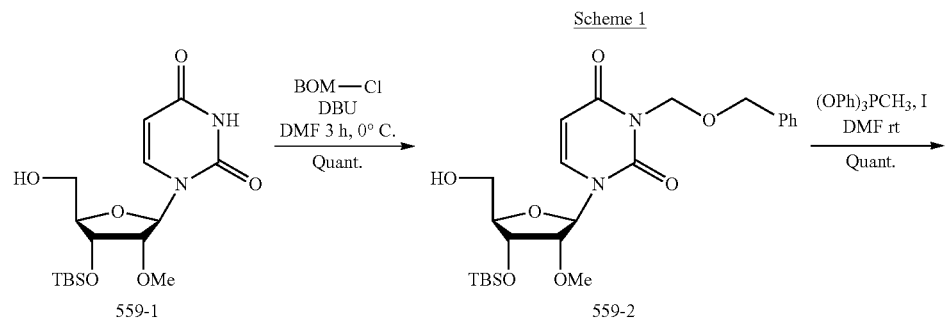

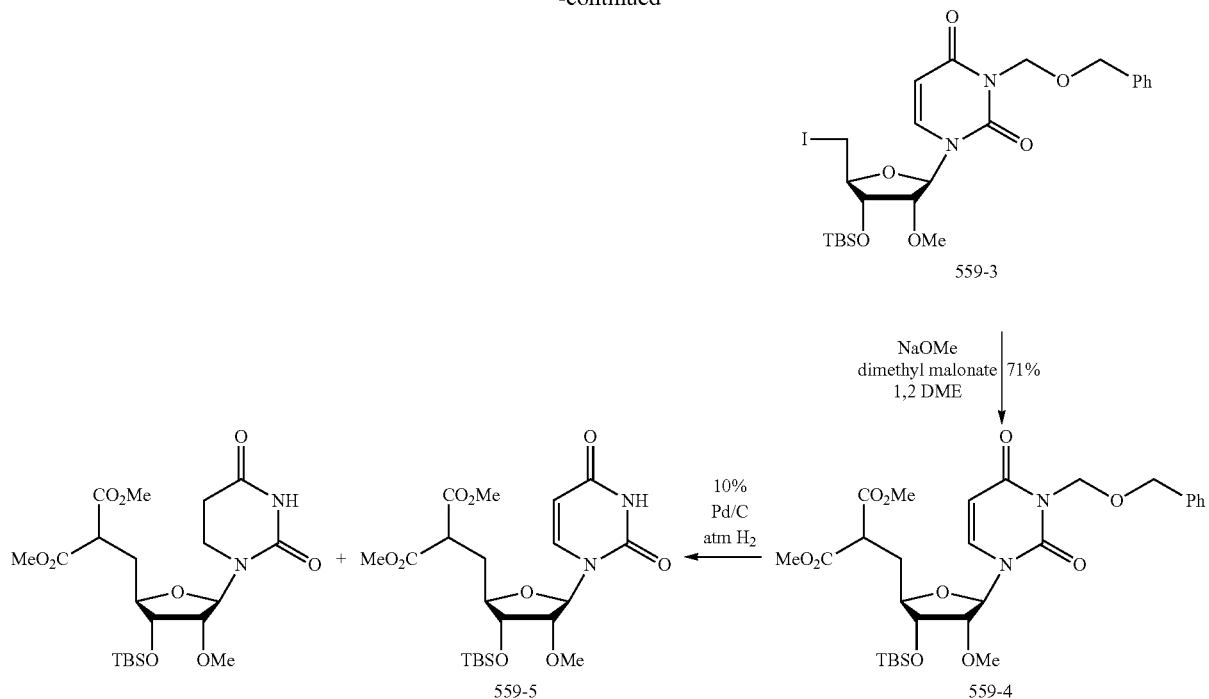

Nucleoside 559-1 (380 mg, 1 mmol) was dissolved in anhydrous DMF (5 mL) and anhydrous DBU (0.3 mL, 2 mmol) was added. The mixture was cooled to 0° C. and then 60% BOM-Cl was added (0.36 mL, 1.5 mmol). The reaction was stirred at 0° C. for 3 h. After completion, the mixture was diluted with methanol, and then evaporated to dryness. The crude residue was purified by silica gel flash chromatography using a gradient of methanol (0 to 5%) in dichloromethane, providing pure 559-2 in a quantitative yield.

559-2 (400 mg, 0.8 mmol) was dissolved in anhydrous DMF (5 mL) and then methyl triphenoxy phosphonium iodide (750 mg, 1.6 mmol) was added. The mixture was stirred at room temperature for 15 min. After completion, methanol was added to the reaction mixture and the solution was stirred for 15 more minutes. The solvents were evaporated to dryness; the residue was redissolved in dichloromethane and washed once with 5% aq. $Na_2S_2O_3$, then once with water. The combined organic layers were dried over $Na_2SO_4$, filtered and evaporated to dryness. The crude residue was purified by silica gel flash chromatography using a gradient of methanol (0 to 10%) in dichloromethane, providing pure 559-3 in a quantitative yield.

Sodium methoxide (120 mg, 2 mmol) was dissolved in anhydrous 1,2-dimethoxyethane (DME, 10 mL). Dimethyl malonate (0.58 mL, 5 mmol) was added to the suspension and the mixture was heated until a reflux was obtained. 559-3 (500 mg, 0.8 mmol), dissolved in 3 mL of DME, was then added to the reaction mixture, and stirred at reflux for 24 h. After completion, the mixture was diluted with methanol, filtered through a 0.45 um Teflon filter and then evaporated to dryness. The crude residue was purified by silica gel flash chromatography using a gradient of ethyl acetate (0 to 100%) in hexanes, providing pure 559-4 in 71% yield.

559-4 (250 mg, 0.4 mmol) was dissolved in methanol (20 mL) and 125 mg of 10% Pd/C were added. The reaction flask was purged three times with hydrogen and kept under positive hydrogen atmosphere as the mixture was stirred overnight at room temperature. After completion, the reaction mixture was diluted with methanol and filtered through Celite. The collected filtrates were evaporated to dryness and the crude residue was purified by silica gel flash chromatography using a gradient of methanol (0 to 10%) in dichloromethane, providing a mixture of 559-5 as inseparable mixture with its over reduced counterpart (Scheme 1).

Example 2. Synthesis of ON-626-7

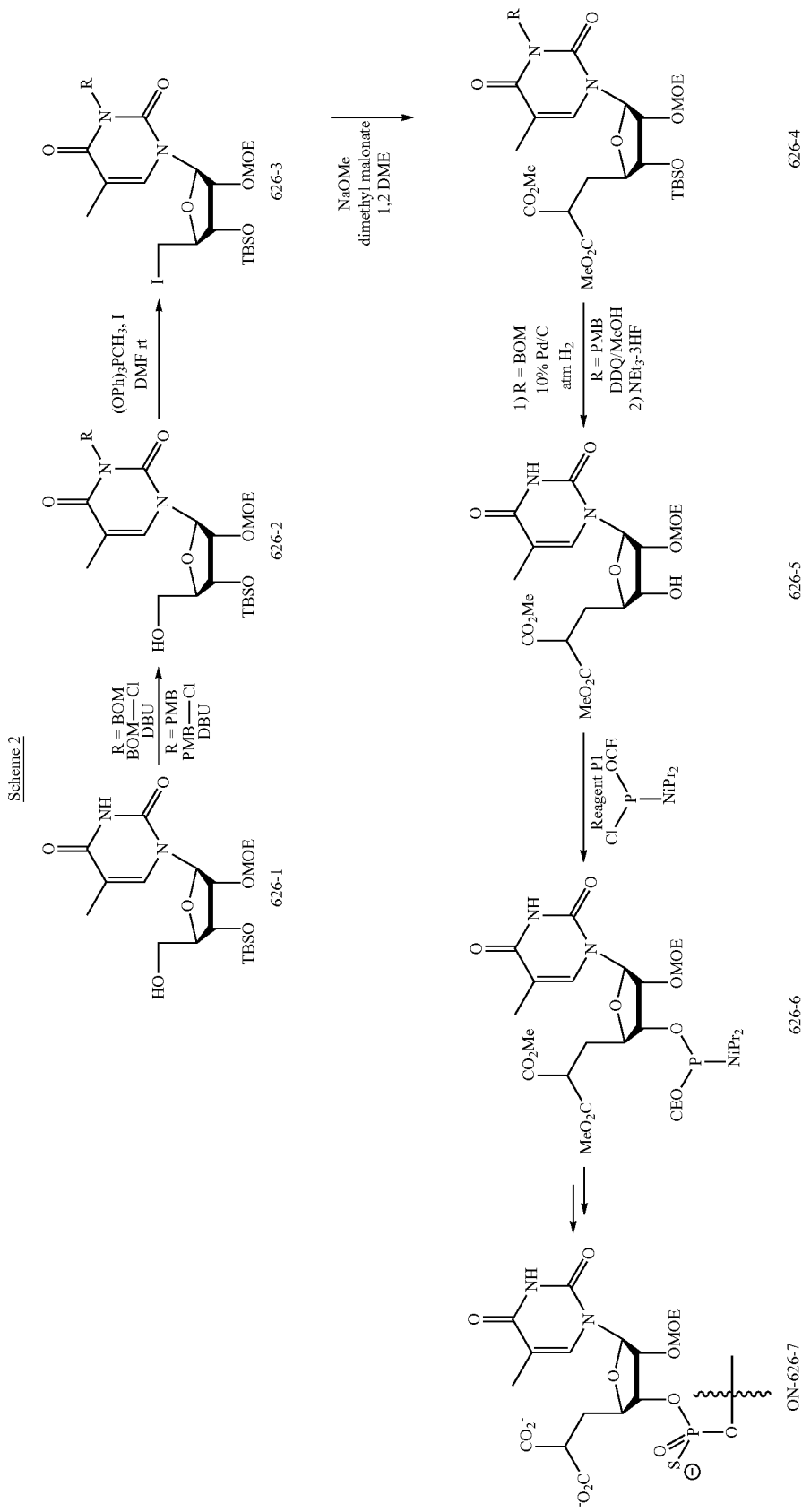

Nucleoside 626-1 (1 equiv) is dissolved in anhydrous DMF and anhydrous DBU (2 equiv) is added. The mixture is cooled to 0° C. and then 60% BOM-Cl is added (Scheme 2, R=BOM, 1.5 equiv); or respectively PMB-Cl (Scheme 2, R=PMB, 1.5 equiv). The reaction is stirred at 0° C. for 3 h. After completion, the mixture is diluted with methanol, and then evaporated to dryness. The crude residue is purified by silica gel flash chromatography using a gradient of methanol (0 to 5%) in dichloromethane.

626-2 (1 equiv) is dissolved in anhydrous DMF and then methyl triphenoxy phosphonium iodide (2 equiv) is added. The mixture is stirred at room temperature for 15 min. After completion, methanol is added to the reaction mixture and the solution is stirred for 15 more minutes. The solvents are evaporated to dryness; the residue is redissolved in dichloromethane and washed once with 5% aq. $Na_2S_2O_3$, then once with water. The combined organic layers are dried over $Na_2SO_4$, filtered and evaporated to dryness. The crude residue is purified by silica gel flash chromatography using a gradient of methanol (0 to 10%) in dichloromethane, providing pure 626-3.

Sodium methoxide (2 equiv) is dissolved in anhydrous 1,2-dimethoxyethane (DME). Dimethyl malonate (5 equiv) is added to the suspension and the mixture is heated until a reflux is obtained. 626-3 (1 equiv), dissolved in of DME, is then added to the reaction mixture, and stirred at reflux for 24 h. After completion, the mixture is diluted with methanol, filtered through a 0.45 um Teflon filter and then evaporated to dryness. The crude residue is purified by silica gel flash chromatography using a gradient of ethyl acetate (0 to 100%) in hexanes, providing pure 626-4.

626-4 (R=BOM, Scheme 2) is dissolved in methanol and 10% Pd/C is added. The reaction flask is purged three times with hydrogen and kept under positive hydrogen atmosphere as the mixture is stirred overnight at room temperature. After completion, the reaction mixture is diluted with methanol and filtered through Celite.

626-4 (R=PMB, Scheme 2) is dissolved in methanol −5% water and DDQ is added. The mixture is stirred at room temperature for 2 h. After completion, the mixture is diluted with methanol and filtered through Celite. The crude reaction mixture is co-evaporated with anhydrous acetonitrile, dissolved in anhydrous THF, and then triethyl-tris HF (10 equiv) is added and the mixture is stirred at room temperature for 15 h. After completion, the solvents are evaporated to dryness, and the crude residue is purified by silica gel flash chromatography using a gradient of methanol (0 to 10%) in dichloromethane, providing pure 626-5.

626-5 is co-evaporated with dry acetonitrile, then dissolved in anhydrous dichloromethane. 1.5 equiv of phosphitylation reagent are added, along with 2 equiv of Hunig base. The reaction mixture is stirred under Argon for 30 min. After completion of the reaction, the mixture is evaporated to dryness and the crude residue is purified by silica gel flash chromatography using a gradient of methanol (0 to 10%) in dichloromethane cont. 1% triethylamine, providing pure 626-6.

626-6 is used in a standard automated oligonucleotide synthesis cycle and is incorporated onto a solid-supported oligonucleotide chain. The solid supported oligonucleotide is deprotected and cleaved from the solid support using 0.1 M NaOH treatment for 30 min at room temperature, further diluted with 30% aq ammonia/EtOH (3:1) and treated 5 h at 55° C. After purification and desalting, pure ON-626-7 is obtained.

Example 3. Synthesis of ON-626-14

Scheme 3
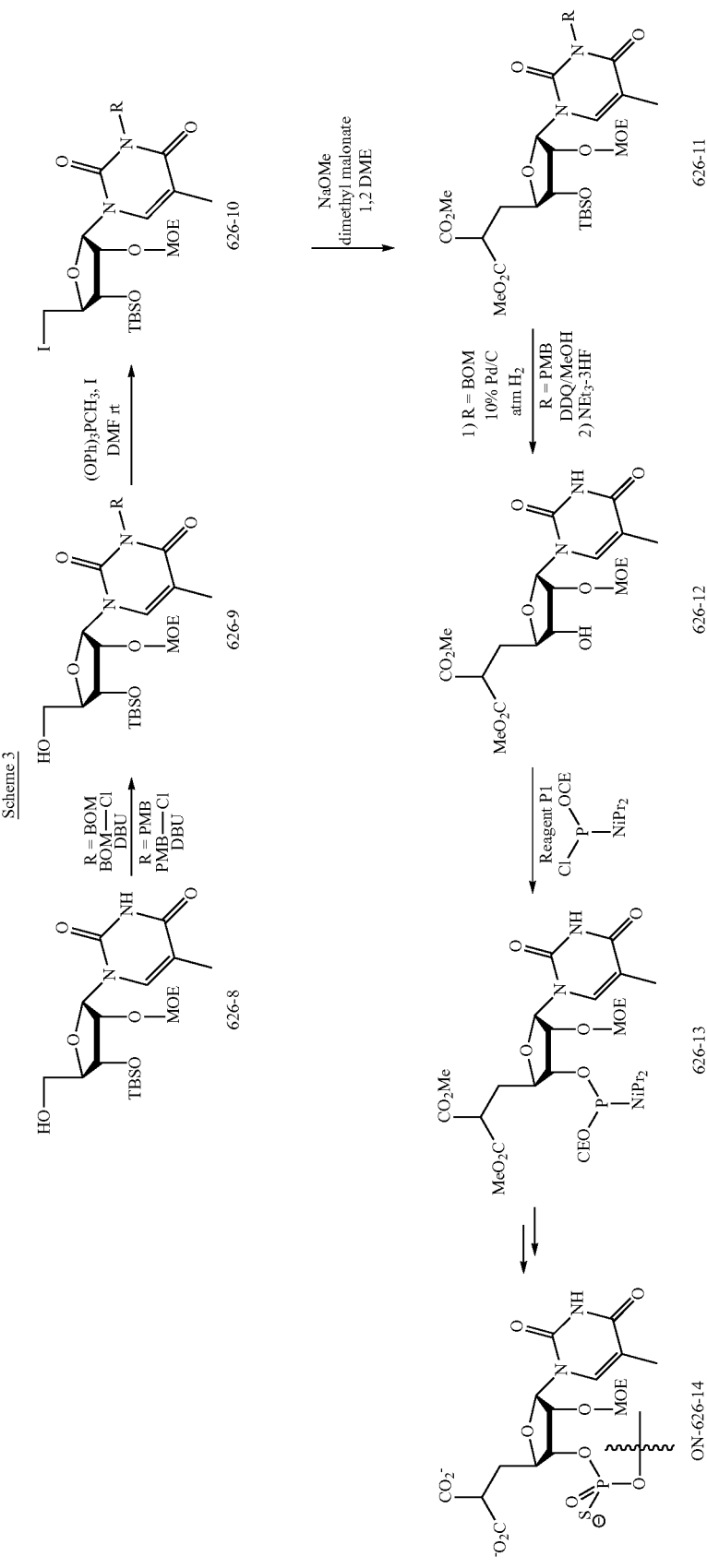

The synthesis of ON-626-14 (Scheme 3) is performed in a similar fashion as the synthesis of ON-626-7 (Scheme 2). Starting from the α-nucleoside 626-8 the synthetic schemes for introducing the 5'-malonyl moiety is identical to the β-anomer analogs. Deprotection, phosphitylation and solid phase oligonucleotide synthesis are also preformed in identical fashion. Deprotection and cleavage from the solid support using 0.1 M NaOH and aqueous ammonia/ethanol, followed by the appropriate purification and desalting steps lead to the desired target ON-626-14.

Example 4. Synthesis of ON-626-17

Scheme 4

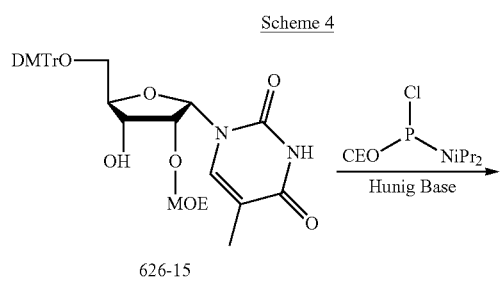

626-15

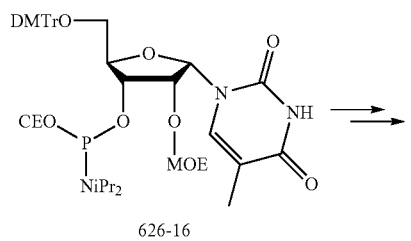

626-16

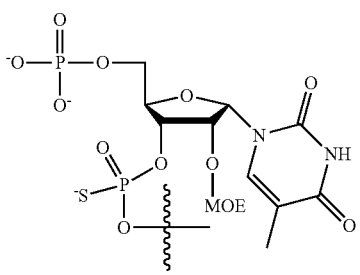

ON-626-17

α-Nucleoside 626-15 is converted to its 3'-phosphoramidite using 1.5 equiv of phosphitylation reagent, along with 2 equiv of Hunig base. The reaction mixture is stirred under Argon for 30 min. After completion of the reaction, the mixture is evaporated to dryness and the crude residue is purified by silica gel flash chromatography using a gradient of methanol (0 to 10%) in dichloromethane cont. 1% triethylamine, providing pure 626-16.

626-16 is used in a standard automated oligonucleotide synthesis cycle and is incorporated onto a solid-supported oligonucleotide chain. Additional 5' phosphate group is added using standard automated procedures. After deprotection, purification and desalting, pure ON-626-17 is obtained.

Example 5. Synthesis of ON-626-23

Scheme 5

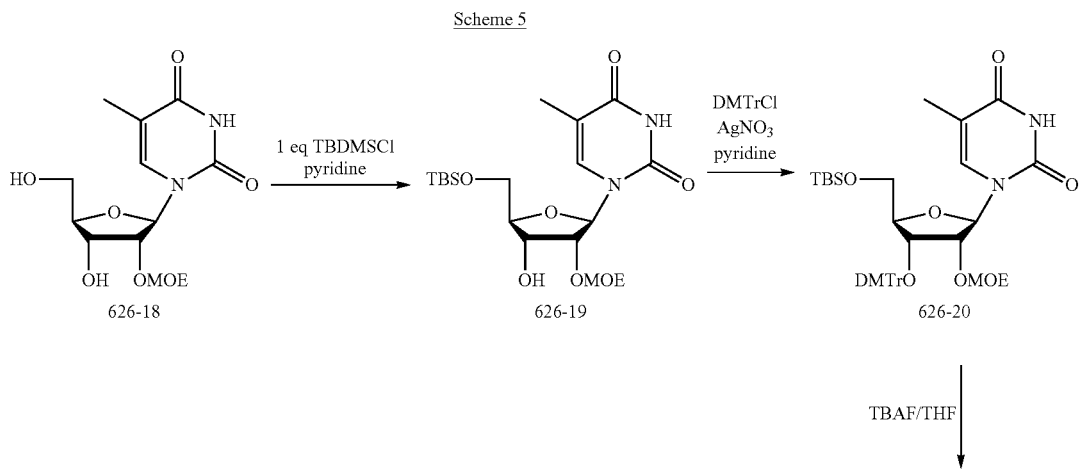

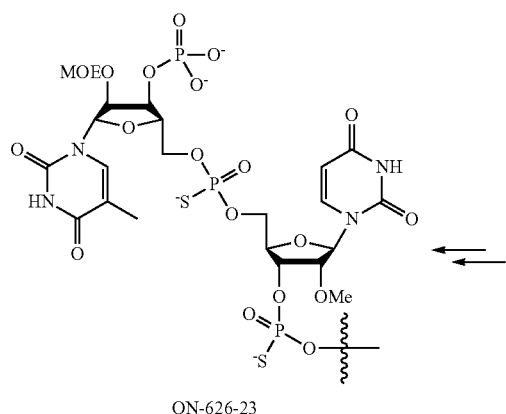
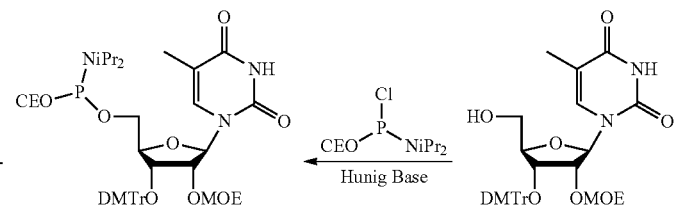

ON-626-23          626-22          626-21

Nucleoside 626-21 is prepared following the procedure described by Wang and Seifert—Tetrahedron Lett., 1996, 37, 6515-6518. Starting nucleoside 626-18 is treated with 1.15 equiv of TBDMS-Cl in pyridine at room temperature. The reaction mixture is quenched by adding saturated aqueous bicarbonate solution, and the solution is extracted with dichloromethane. The aqueous layers are dried, filtered and evaporated to dryness. The crude residue is purified by silica gel flash chromatography affording pure 626-19.

It is then dissolved in pyridine, silver nitrate is added and then 2 equiv of DMTrCl. The mixture is stirred overnight. After aqueous work up and silica gel flash chromatography purification, the obtained pure 626-20 is dissolved in anhydrous THF and treated with 1 M TBAF. The solvents are evaporated to dryness and the residue is purified by silica gel flash chromatography.

Nucleoside 626-21 is converted to its 5'-phosphoramidite using 1.5 equiv of phosphitylation reagent, along with 2 equiv of Hunig base. The reaction mixture is stirred under Argon for 30 min. After completion of the reaction, the mixture is evaporated to dryness and the crude residue is purified by silica gel flash chromatography using a gradient of methanol (0 to 10%) in dichloromethane cont. 1% triethylamine, providing pure 626-22.

626-22 is used in a standard automated oligonucleotide synthesis cycle and is incorporated onto a solid-supported oligonucleotide chain. Additional 3' phosphate group is added using standard automated procedures. After deprotection, purification and desalting, pure ON-626-23 is obtained.

Example 6. Synthesis of ON-626-26

Scheme 6

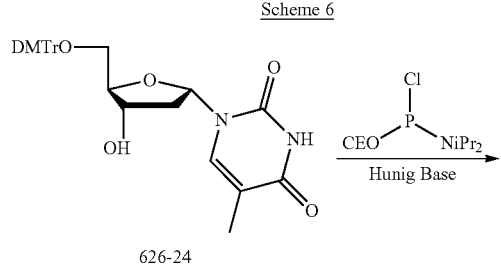

626-24

-continued

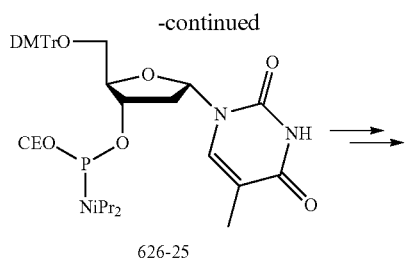

626-25

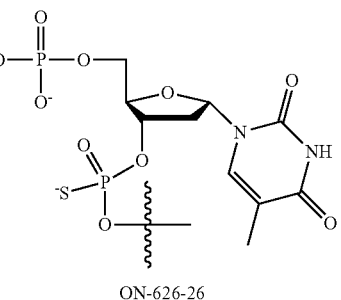

ON-626-26

α-Nucleoside 626-24 is converted to its 3'-phosphoramidite using 1.5 equiv of phosphitylation reagent, along with 2 equiv of Hunig base. The reaction mixture is stirred under Argon for 30 min. After completion of the reaction, the mixture is evaporated to dryness and the crude residue is purified by silica gel flash chromatography using a gradient of methanol (0 to 10%) in dichloromethane cont. 1% triethylamine, providing pure 626-25.

626-25 is used in a standard automated oligonucleotide synthesis cycle and is incorporated onto a solid-supported oligonucleotide chain. Additional 5' phosphate group is added using standard automated procedures. After deprotection, purification and desalting, pure ON-626-26 is obtained.

Example 7. Synthesis of ON-626-32

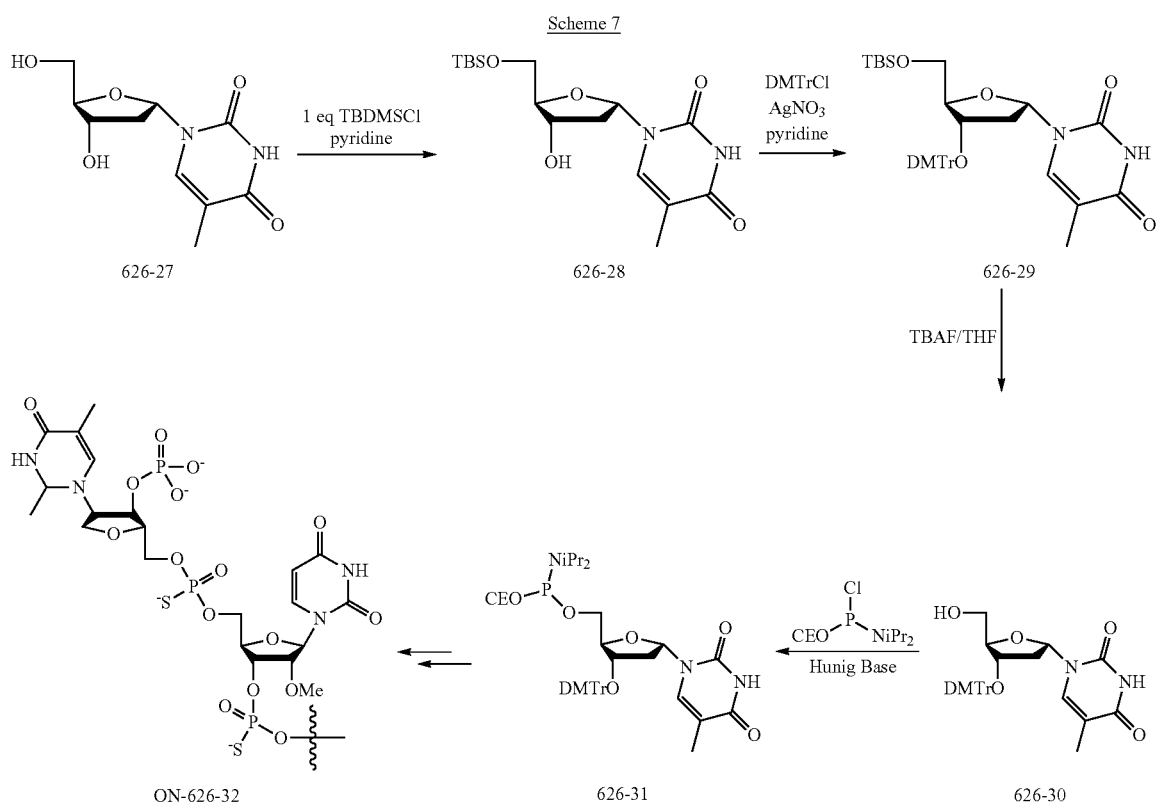

ON-626-32 is prepared in a similar fashion to ON-626-23, using the 5'-phosphoramidite α-nucleoside 626-31, prepared from the starting α-nucleoside 626-27 using identical strategy to the one depicted on Scheme 5.

Synthesis of 5'-Amino Acid Conjugated Phosphoramidate Monoesters

Example 8. Synthesis of 5'-Amino Acid Conjugated Phosphoramidate Monoesters

5'-Phosphoramidate esters of nucleosides have been extensively developed as prodrugs delivering very efficiently the corresponding NMP (Reviewed in Hecker and Erion, *J. Med. Chem.*, 2008, 51, 2321).

Due to the basic treatment required for cleavage of oligonucleotides from solid support and deprotection, the approaches using neutral phosphotriesters or phosphoramidate diesters are not suitable for the application into the 5' end of siRNA.

However, 5' phosphoramidate monoester conjugates are an interesting alternative of delivering pro-5'-phosphates of siRNA. Upon the action of cellular phosphoramidases, L-amino acid 5' phosphoramidate siRNA can generate the target 5'-monophosphate siRNA (Scheme 8).

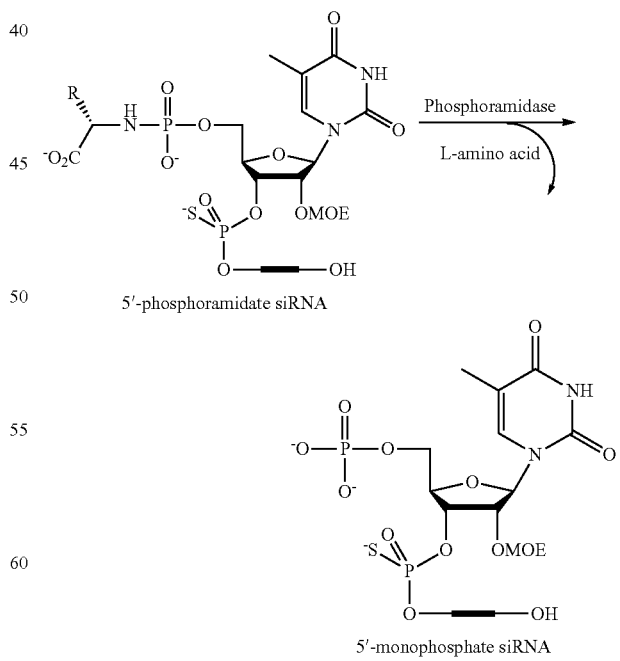

On the nucleoside level this type of structures has been used by Wagner et al. as a prodrug masking group (Drontle and Wagner, *Mini Rev. Med. Chem.*, 2004, 4, 409). More recently, this kind of conjugates were identified by Herdewijn et al. as efficient triphosphate mimics of nucleosides, as they were successfully incorporated into DNA by HIV-I RT. These constructs include either conjugates with natural amino acid residues (Adelfinskaya and Herdewijn, Angew. *Chem. Int. Ed. Eng.*, 2007, 46, 4356; *Nucl. Acid. Res.*, 2007, 35, 5060) or with modified negatively charged non natural amino acids (Zlatev et al., *Bioorg. Med. Chem.*, 2009, 17, 7008; Giraut et al., *Nucl. Acid. Res.*, 2010, doi:10.1093/nar/gkp1246).

dation of 5'-H-phosphonate monoesters; the second one is the DCC activated coupling of 5'-monophosphates and the corresponding amino acid.

Several examples are described in the following examples.

Example 9. Synthesis of ON-626-36 Conjugates with Amino Acids from Table (Shown in Scheme 9) Using H-Phosphonate Chemistry

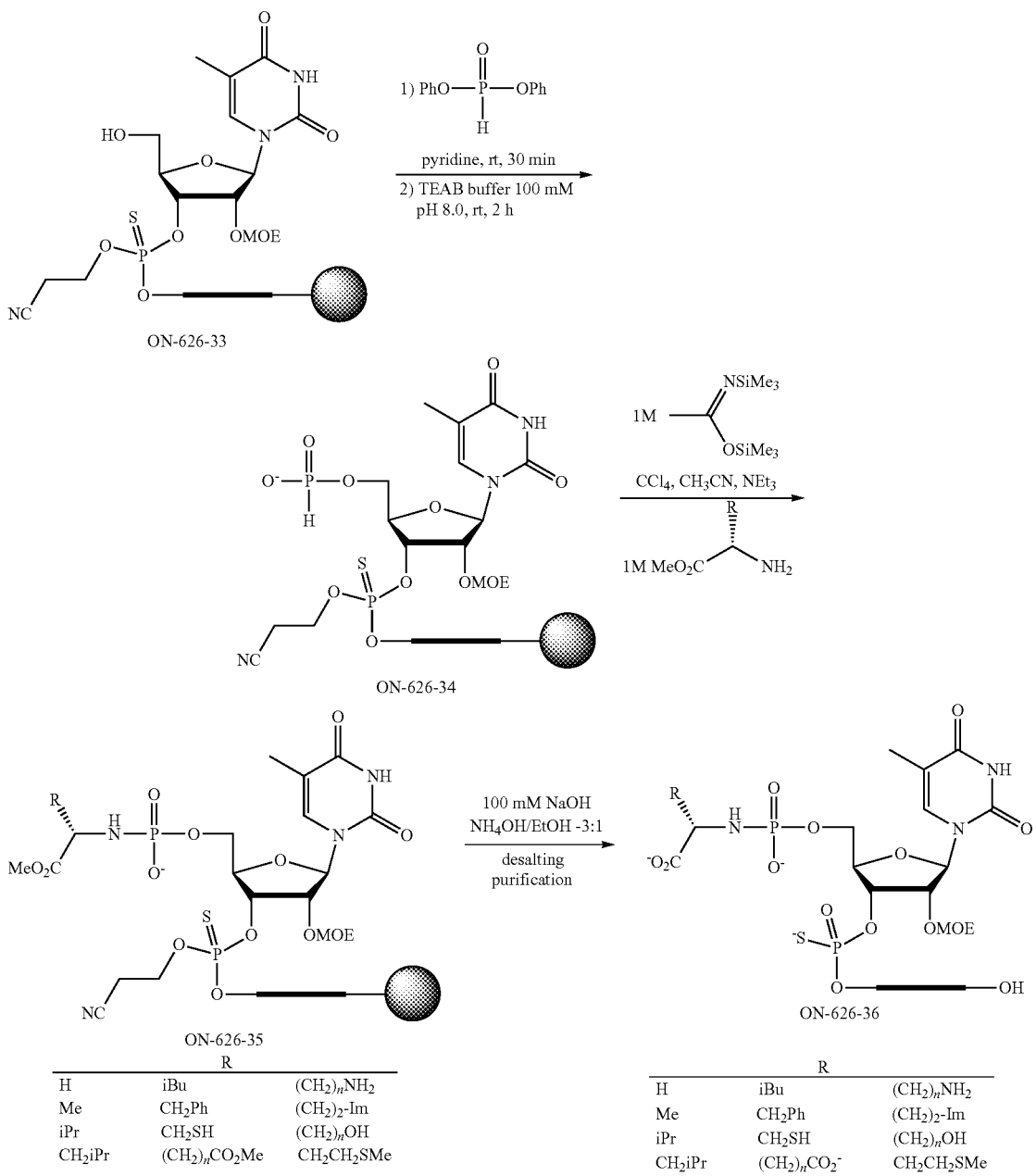

Two major approaches are used for the synthesis of these compounds, the first one is the amino acid amidative oxi- Solid supported oligonucleotide ON-626-33 is treated with 1 M solution of diphenyl phosphite in pyridine for 30 min at rt, then the support is washed and treated with 100 mM solution of triethylammonium bicarbonate aqueous buffer for 2 h at rt. The solid support is washed off and then treated with a solution containing: 1 M bis-trimethylsilyl acetamide, CCl$_4$, acetonitrile, triethylamine and 1 M methyl ester of the appropriate amino acid. The solution is left to react with the solid support for 5 h at rt. The solid support is washed off then treated firstly with 100 mM aqueous NaOH for 30 min, then ammonia/ethanol 3:1 is added and the mixture is heated for 5 h at 55° C. The solid support is filtered off and the solution is quickly desalted, then lyophilized. The pure ON-626-36 is obtained after appropriate purification and final desalting.

Example 10. Synthesis of ON-626-40 Conjugates with Amino Acids from Table (Shown in Scheme 10) Using Thio-H-Phosphonate Chemistry

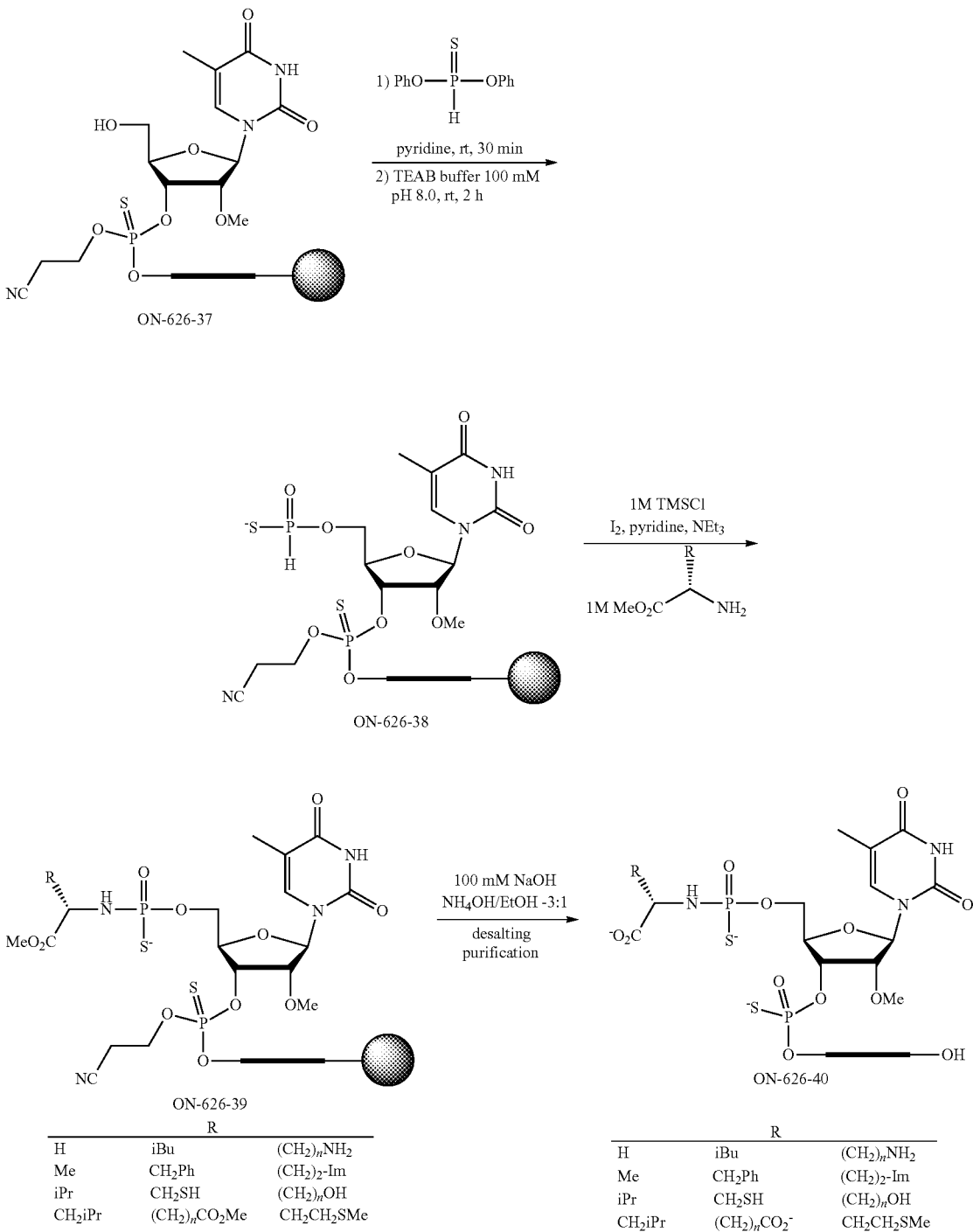

Solid supported oligonucleotide ON-626-37 is treated with 1 M solution of diphenyl thiophosphite in pyridine for 30 min at rt, then the support is washed and treated with 100 mM solution of triethylammonium bicarbonate aqueous buffer for 2 h at rt. The solid support is washed off and then treated with a solution containing: 1 M trimethylsilyl chloride, iodine, pyridine, triethylamine and 1 M methyl ester of the appropriate amino acid. The solution is left to react with the solid support for 5 h at rt. The solid support is washed off then treated firstly with 100 mM aqueous NaOH for 30 min, then ammonia/ethanol 3:1 is added and the mixture is heated for 5 h at 55° C. The solid support is filtered off and the solution is quickly desalted, then lyophilized. The pure ON-626-40 is obtained after appropriate purification and final desalting.

Example 11. Synthesis of ON-626-36 Conjugates with Amino Acids from Table (Shown in Scheme 11) Using 5'-Mono Phosphate Chemistry

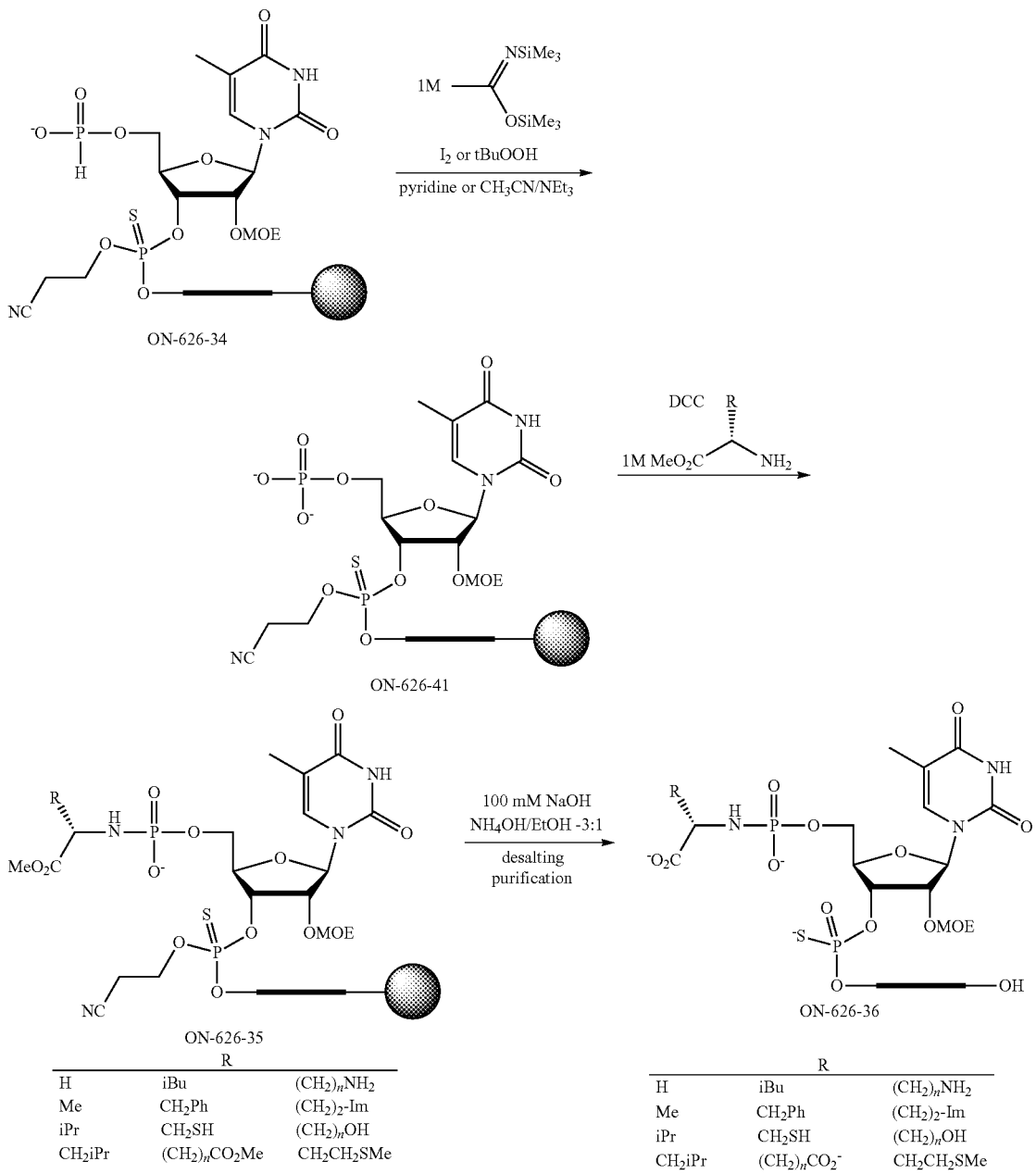

Solid supported oligonucleotide H-phosphonate ON-626-34 is treated with 1 M bis-trimethylsilyl acetamide, mixed with iodine/pyridine or tert-butyl hydroperoxide/acetonitrile/triethylamine leading to 5'-monophosphate solid supported oligonucleotide ON-626-41. The support is washed off and then treated with DCC/pyridine and 1 M methyl ester of the appropriate amino acid. The solution is left to react with the solid support for 5 h at rt. The solid support is washed off then treated firstly with 100 mM aqueous NaOH for 30 min, then ammonia/ethanol 3:1 is added and the mixture is heated for 5 h at 55° C. The solid support is filtered off and the solution is quickly desalted, then lyophilized. The pure ON-626-36 is obtained after appropriate purification and final desalting.

Synthesis of 5'-Amino Acid Phosphoro Bis Amidates

Example 12. Synthesis of 5'-Amino Acid Phosphoro Bis Amidates

5'-amino acid phosphoro bis amidates was introduced for the first time by Jones, McGuigan et al. *Antivir. Chem.*, 1991, 2, 35. Nevertheless they haven't found a large application within the pro-nucleotide field until two more recent reports by Erion et al. (*Proc. Nat. Acad. Sc.*, 2005, 102, 7970; *J. Am. Chem. Soc.*, 2007, 129, 15491).

Their intracellular cleavage to generate the corresponding 5'-monophosphate involves a spontaneous hydrolysis of one of the amino acid moieties, followed by the action of phosphoramidase, as shown in Scheme 12.

Scheme 12

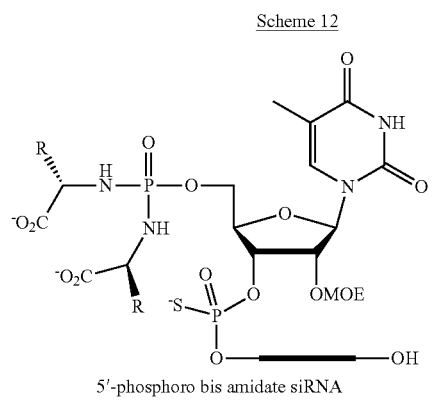

5'-phosphoro bis amidate siRNA

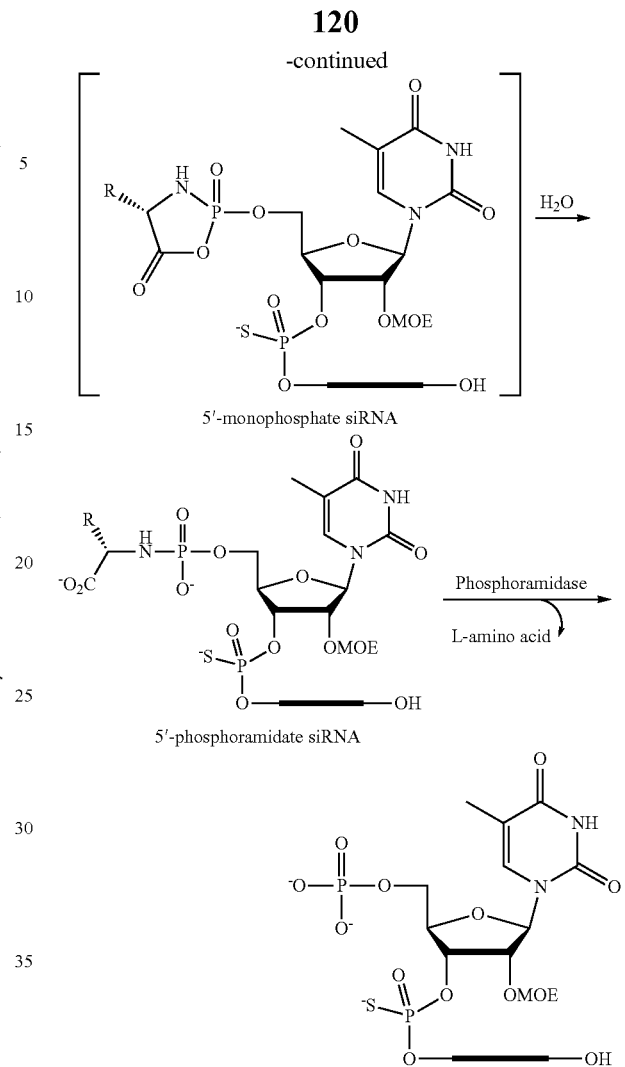

5'-monophosphate siRNA

5'-phosphoramidate siRNA

Example 13. Synthesis of ON-626-43 Phosphoro Bis Amidate Conjugates with Amino Acids from Table (Shown in Scheme 13) Using 5'-Mono Phosphate Chemistry Scheme 13

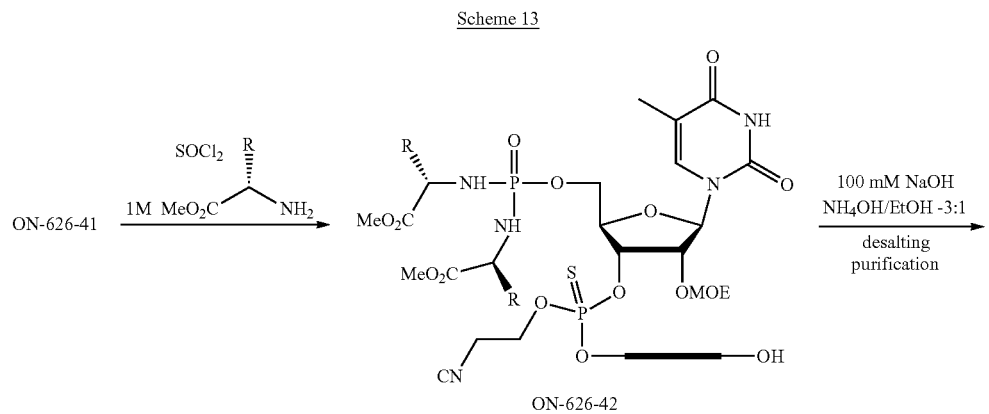

ON-626-42

-continued

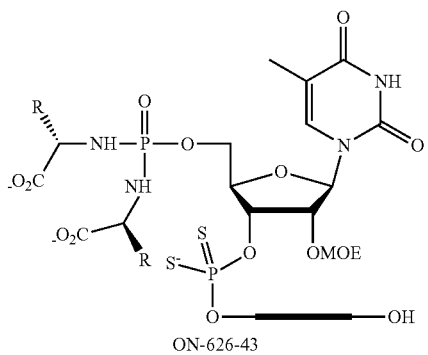

ON-626-43

| R | | |
|---|---|---|
| H | iBu | $(CH_2)_nNH_2$ |
| Me | $CH_2Ph$ | $(CH_2)_2$-Im |
| iPr | $CH_2SH$ | $(CH_2)_nOH$ |
| $CH_2iPr$ | $(CH_2)_nCO_2Me$ | $CH_2CH_2SMe$ |

| R | | |
|---|---|---|
| H | iBu | $(CH_2)_nNH_2$ |
| Me | $CH_2Ph$ | $(CH_2)_2$-Im |
| iPr | $CH_2SH$ | $(CH_2)_nOH$ |
| $CH_2iPr$ | $(CH_2)_nCO_2^-$ | $CH_2CH_2SMe$ |

Solid supported oligonucleotide ON-626-41. The support is washed off and then treated with thionyl chloride/pyridine and 1 M methyl ester of the appropriate amino acid. The solution is left to react with the solid support for 5 h at rt. The solid support is washed off then treated firstly with 100 mM aqueous NaOH for 30 min, then ammonia/ethanol 3:1 is added and the mixture is heated for 5 h at 55° C. The solid support is filtered off and the solution is quickly desalted, then lyophilized. The pure ON-626-36 is obtained after appropriate purification and final desalting.

5'-Functionalization with D- and L-Aspartic Acid Using Reductive Amination

Example 14. 5'-Functionalization with D- and L-aspartic acid using reductive amination Scheme 14

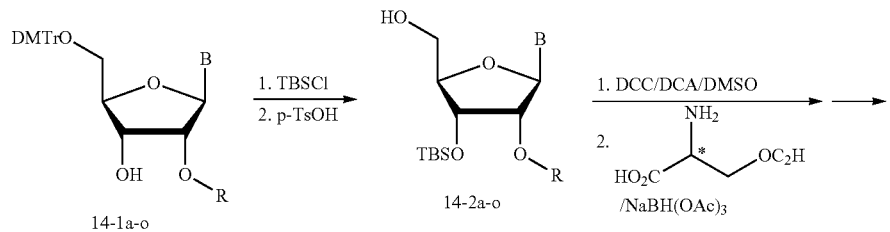

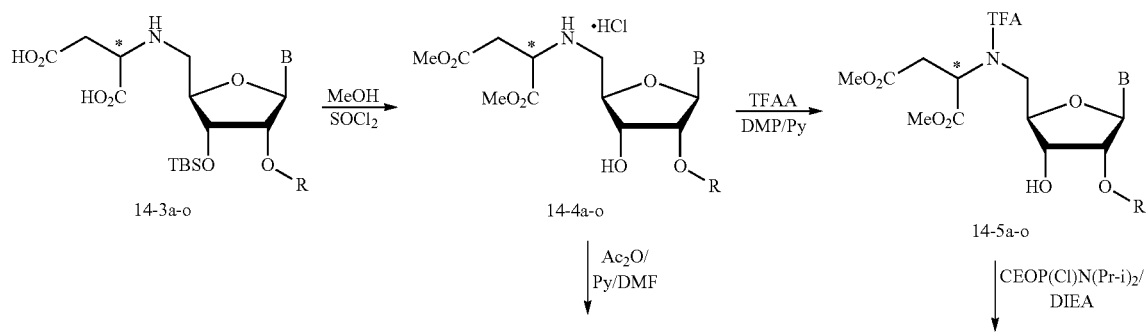

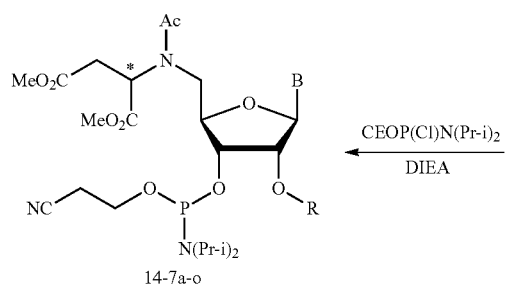
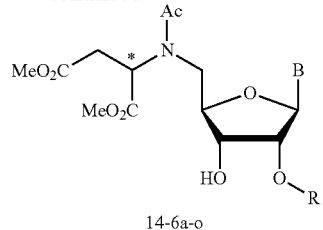
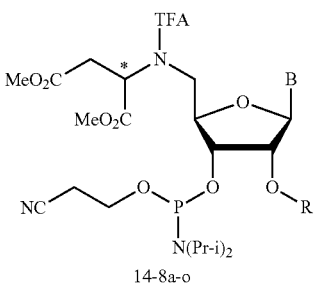
14-7a-o
B = U, R = Me (a)  B = U, R = MOE (f)  B = U, R = (S)-2-Me-MOE (k)
B = T, R = Me (b)  B = T, R = MOE (g)  B = T, R = (S)-2-Me-MOE (l)
B = A$^{Bz}$, R = Me (c)  B = A$^{Bz}$, R = MOE (h)  B = A$^{Bz}$, R = (S)-2-Me-MOE (m)
B = C$^{Ac}$, R = Me (d)  B = C$^{Ac}$, R = MOE (i)  B = C$^{Ac}$, R = (S)-2-Me-MOE (n)
B = G$^{ibu}$, R = Me (e)  B = G$^{ibu}$, R = MOE (j)  B = G$^{ibu}$, R = (S)-2-Me-MOE (o)
Example 15. 5'-Functionalization with D- and L-Aspartic Acid Using Reductive Amination
Scheme 15
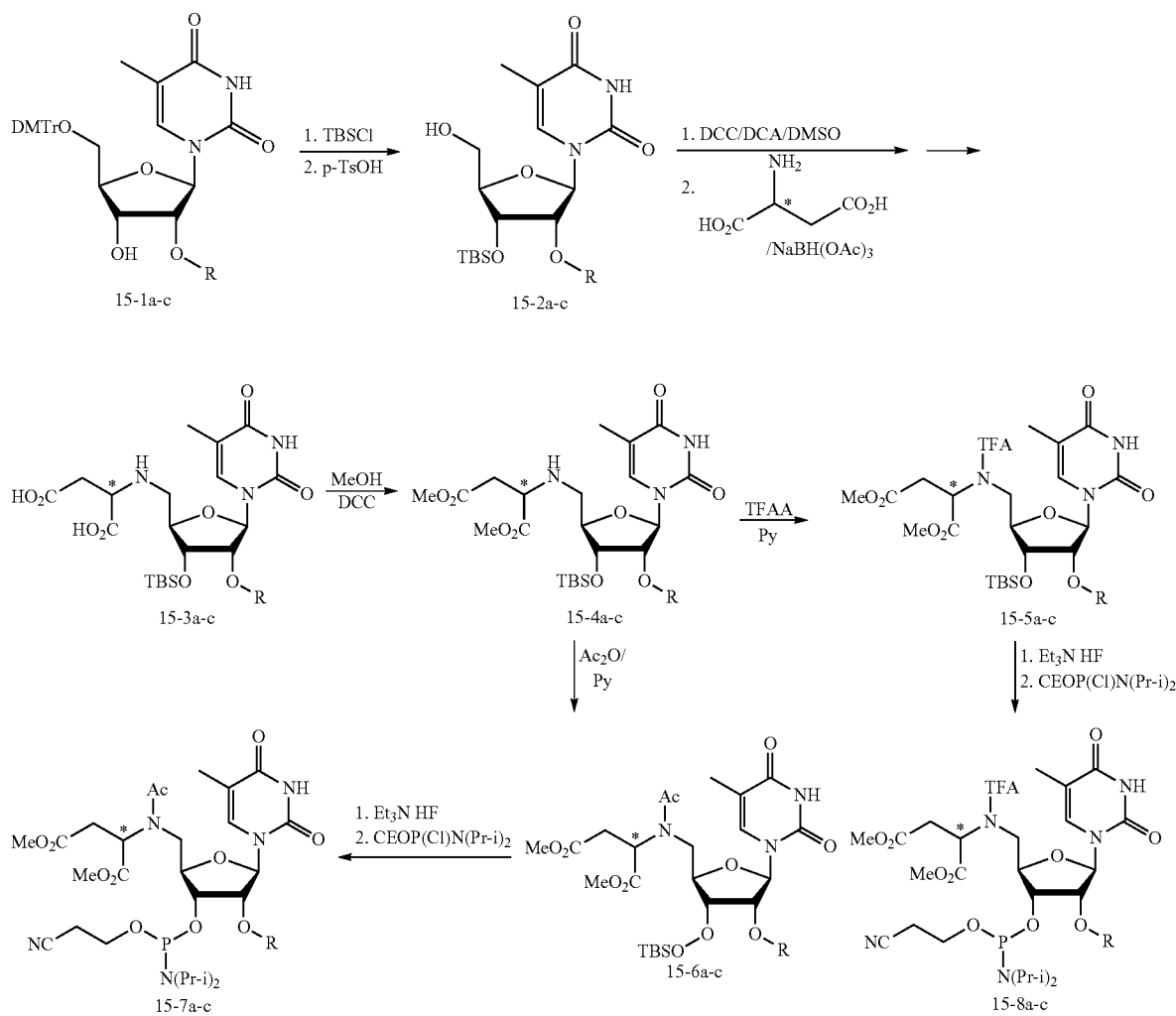
R = Me (a), MOE (b), (S)-2-Me-MOE (c)

Example 16. RNA 5'-L-Aspartete Analogue (6)

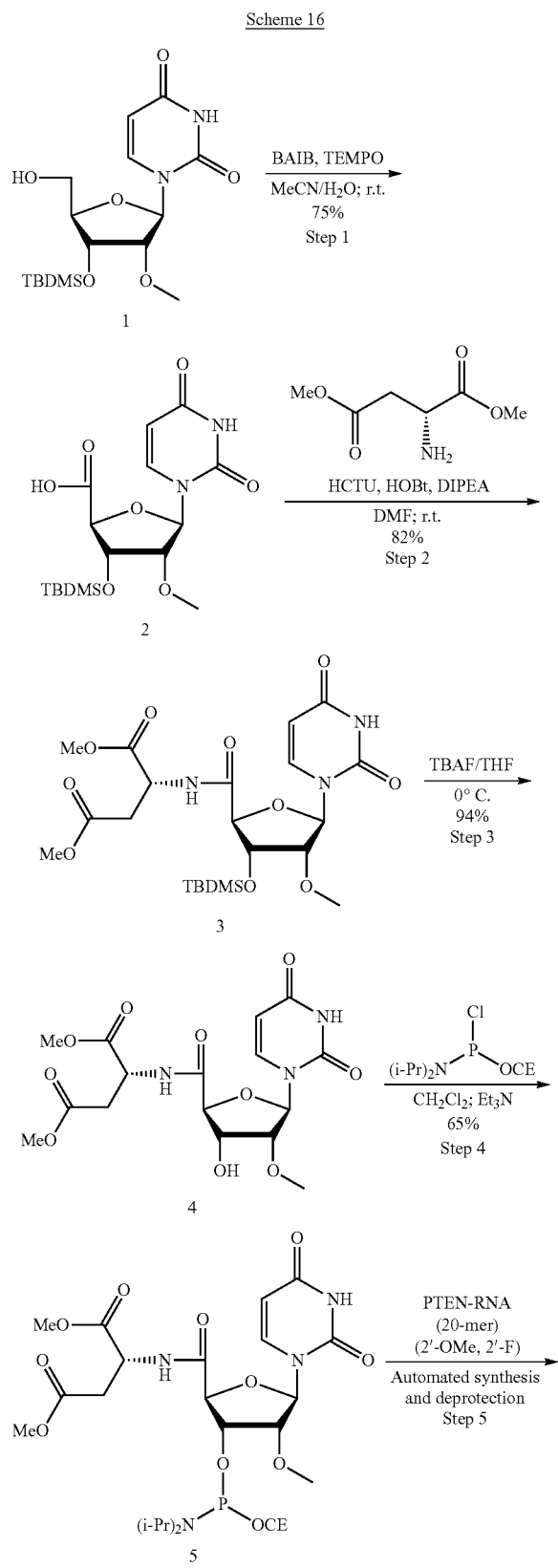

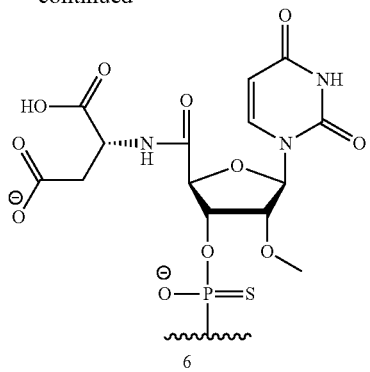

Step 1 (Preparation of 3'-O-tert-butyldimethylsilyl-2'-O-methyluridine 5'-carboxilic acid, 2): (Bisacetoxy)iodobenzene (BAIB) (2.84 g, 8.8 mmol), 2,2,6,6-tetramethyl-1-piperidinyloxyl (TEMPO) (128 mg, 0.8 mmol), and 3'-O-tert-butyldimethylsilyl-2'-O-methyluridine (1) (1.48 g, 4.0 mmol) were combined in a flask and to this mixture was added 8 mL of water/acetonitrile (1/1). The reaction mixture was stirred at room temperature for 5 h and then evaporated. The solid residue was treated with acetonitrile and white precipitate was filtered off (0.97 g). Filtrate was evaporated, residue treated with diethyl ether and off-white precipitate filtered off (0.22 g). Total yield was 77%.

Step 2 (Preparation of compound 3): Under Ar atmosphere 3'-O-tert-butyldimethylsilyl-2'-O-methyluridine 5'-carboxilic acid (2) (514 mg, 1.3 mmol), 2-(6-chloro-1H-benzotriazolyl)-1,1,3,3-tetramethyluronium hexafluorophosphate (HCTU) (605 mg, 1.46 mmol) and 1-hydroxybenzotriazole (HOBt) (198 mg, 1.46 mmol) were dissolved in anhydrous DMF (3.5 mL). Diisopropylethylamine (DIPEA) (254 μL, 1.46 mmol) was added then and, after 1 min. stirring, solution of dimethyl-L-aspartate hydrochloride (526 mg, 2.66 mmol) in DMF (2.7 mL) and DIPEA (0.7 mL) was added via a syringe. Resulting mixture was stirred at room temperature for 40 h and then evaporated to thick oil. Purification on silica gel column with $CH_2Cl_2$-MeOH (0 to 5%) yielded target compound as off-white foam (0.58 g, 82%).

Step 3 (Preparation of compound 4): To a solution of compound 3 (570 mg, 1.08 mmol) in THF (10 mL) at 0° C. was added TBAF/THF (1 M, 2.16 mL, 2 equiv) and resulting mixture stirred at 0° C. for 1 h. Reaction was quenched then with silica, evaporated to dryness and purified on silica column with $CH_2Cl_2$-MeOH (0 to 10%) to yield 0.42 g (94%) of the target compound as an off-white foam.

Step 4 (Preparation of compound 5): To a solution of compound 4 (415 mg, 1 mmol) in $CH_2Cl_2$ (10 mL) were added DIPEA (0.52 mL, 3 mmol) and N,N-diisopropyl (2-cyanoethyl)chlorophosphoramidite (0.36 mL, 1.6 mmol) and the resulting mixture stirred at room temperature for 1.5 h. Reaction was quenched with MeOH and then solvents removed in vacuum. Purification on silica gel column with $CH_2Cl_2$ containing 1% $Et_3$N-MeOH (0 to 5%) yielded target phosphoramidite 5 (0.4 g, 65% yield) as a white foam.
$^{31}$P-NMR (CD$_3$CN): δ 155.25, 157.1.
MS (negative mode): m/z 674.3 (M−1).

Step 5 (Preparation of compound 6): Phosphoramidite 5 (0.15 M in MeCN) was coupled onto the 5'-end of 20-mer RNA on solid support using standard automated oligonucleotide synthesis conditions. Treatment of oligonucleotide on solid support with 0.1 M piperidine in anhydrous acetonitrile for 30 min was followed by hydrolysis with 0.1 aq. NaOH for 30 min. To this mixture was added ammonia in EtOH (4× the volume of aq. NaOH) and heated at 50° C. for 5 h. Filtrate was desalted by RP-HPLC then purified by ion-exchange chromatography followed by desalting to give the target oligonucleotide 6.

Example 17. RNA 5'-L-Serine Analogues 11 and 12

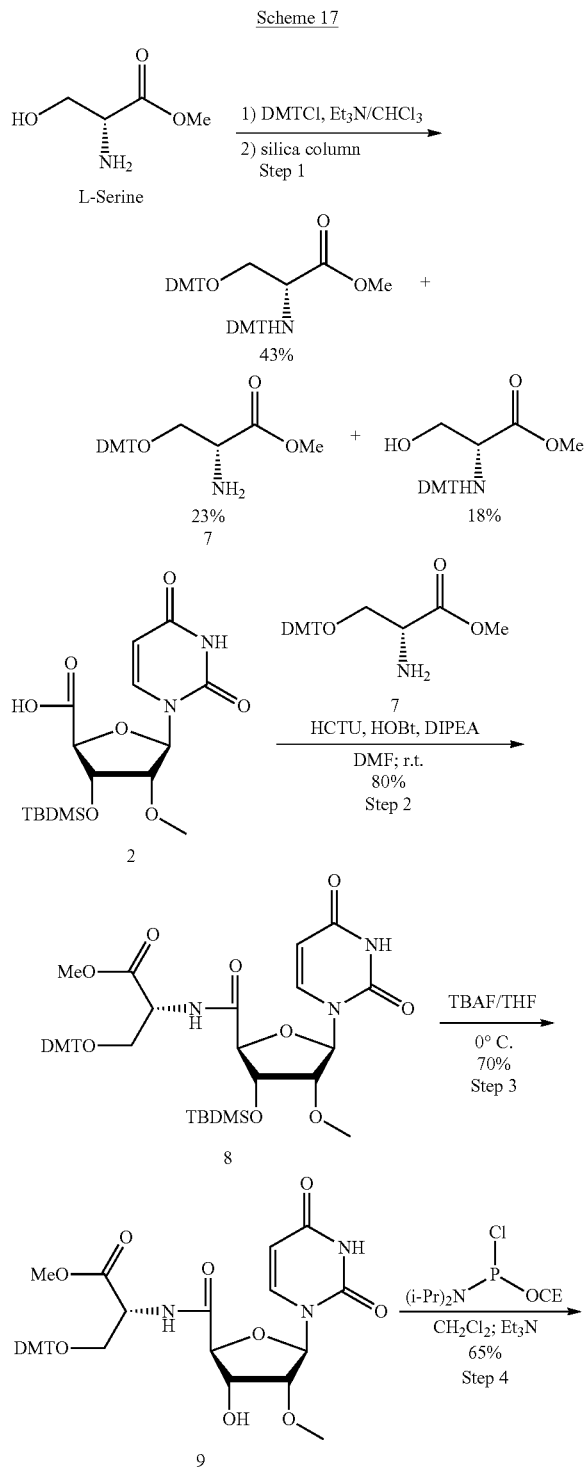

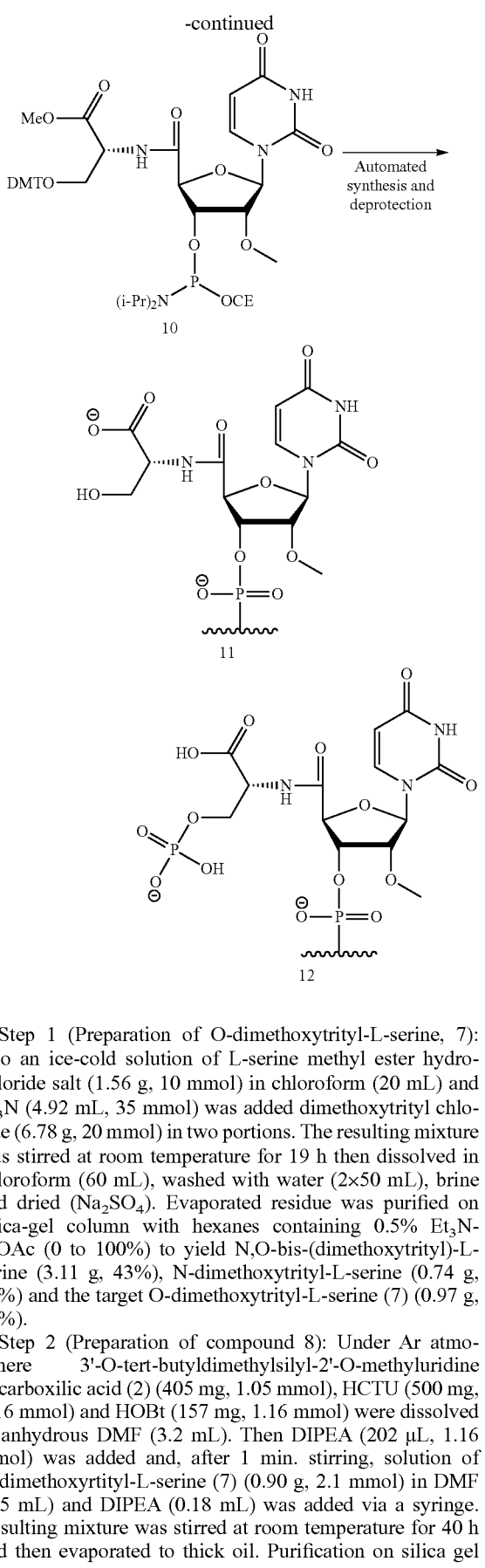

Step 1 (Preparation of O-dimethoxytrityl-L-serine, 7): Into an ice-cold solution of L-serine methyl ester hydrochloride salt (1.56 g, 10 mmol) in chloroform (20 mL) and Et$_3$N (4.92 mL, 35 mmol) was added dimethoxytrityl chloride (6.78 g, 20 mmol) in two portions. The resulting mixture was stirred at room temperature for 19 h then dissolved in chloroform (60 mL), washed with water (2×50 mL), brine and dried (Na$_2$SO$_4$). Evaporated residue was purified on silica-gel column with hexanes containing 0.5% Et$_3$N-EtOAc (0 to 100%) to yield N,O-bis-(dimethoxytrityl)-L-serine (3.11 g, 43%), N-dimethoxytrityl-L-serine (0.74 g, 18%) and the target O-dimethoxytrityl-L-serine (7) (0.97 g, 23%).

Step 2 (Preparation of compound 8): Under Ar atmosphere 3'-O-tert-butyldimethylsilyl-2'-O-methyluridine 5'-carboxylic acid (2) (405 mg, 1.05 mmol), HCTU (500 mg, 1.16 mmol) and HOBt (157 mg, 1.16 mmol) were dissolved in anhydrous DMF (3.2 mL). Then DIPEA (202 µL, 1.16 mmol) was added and, after 1 min. stirring, solution of O-dimethoxyrtityl-L-serine (7) (0.90 g, 2.1 mmol) in DMF (2.5 mL) and DIPEA (0.18 mL) was added via a syringe. Resulting mixture was stirred at room temperature for 40 h and then evaporated to thick oil. Purification on silica gel column with hexane containing 1% Et₃N-EtOAc (0 to 70%) yielded target compound as pale-yellow foam (0.63 g, 80%).

Step 3 (Preparation of compound 9): To a solution of compound 8 (0.60 g, 0.76 mmol) in THF (8 mL) at 0° C. was added TBAF/THF (1 M, 1.52 mL, 2 equiv) and resulting mixture stirred at 0° C. for 1 h. Reaction was quenched with silica, evaporated to dryness and purified on silica column with $CH_2Cl_2$ containing 0.5% Et₃N-MeOH (0 to 10%) to yield 0.36 g (71%) of the target compound as an off-white foam.

Step 4 (Preparation of compound 10): To a solution of compound 9 (0.39 g, 0.58 mmol) in $CH_2Cl_2$ (10 mL) were added DIPEA (0.40 mL, 2.3 mmol) and N,N-diisopropyl (2-cyanoethyl)chlorophosphoramidite (0.26 mL, 1.2 mmol) and the resulting mixture stirred at room temperature for 1.5 h. Reaction was quenched with MeOH and then solvents removed in vacuum. Purification on silica gel column with $CH_2Cl_2$ containing 1% pyridine-MeOH (0 to 5%) yielded target phosphoramidite 10 (0.33 g, 65% yield).

$^{31}$P-NMR (CD₃CN): δ 155.4, 156.9.

MS (negative mode): m/z 874.3 (M−1).

Step 5 (Preparation of compounds 11 and 12): Phosphoramidite 10 (0.15 M in MeCN) was coupled onto the 5'-end of 20-mer RNA on solid support using standard automated oligonucleotide synthesis conditions. After detritylation step solid support was divided in two portions. One portion was treated with 0.1 M piperidine in anhydrous acetonitrile at room temperature for 30 min followed by hydrolysis with 0.1 aq. NaOH for 30 min. To this mixture was added ammonia in EtOH (4× the volume of aq. NaOH) and heated at 50° C. for 5 h. Filtrate was desalted by RP-HPLC then purified by ion-exchange chromatography followed by RP-HPLC desalting to yield the target compound 11. The other portion of oligonucleotide on solid support was coupled with Glen chemical phosphorylation reagent under standard condition. Target oligonucleotide 12 was isolated after standard detritylation on solid support, followed by treatment with piperidine/acetonitrile, aqueous hydrolysis and HPLC purification in the same fashion as described for the compound 11 (vide supra).

Example 18. Ethyl Heptofuranuronate Analogues of 2'-O-(2-Methoxyethyl)-5-Methyluridine

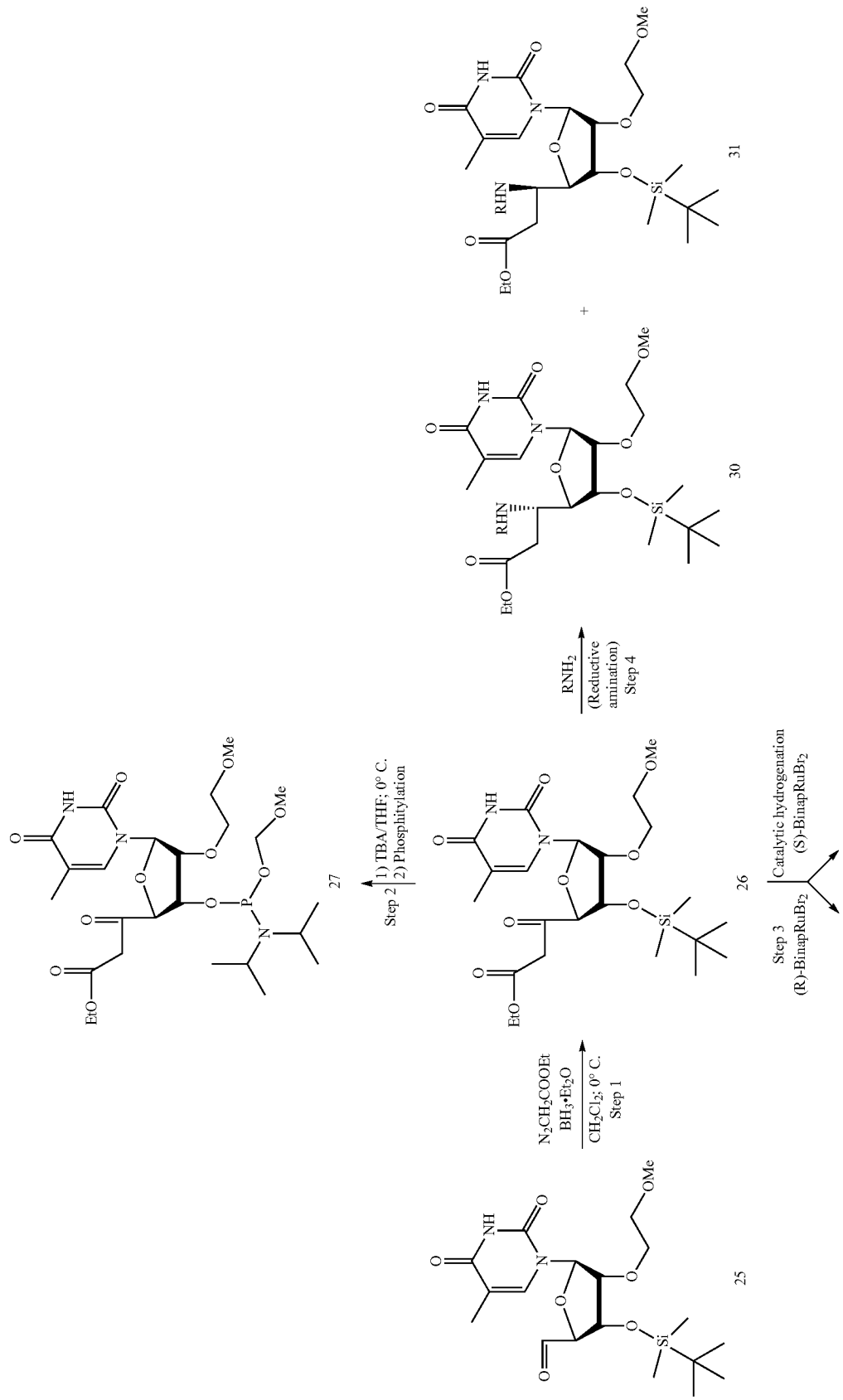

-continued
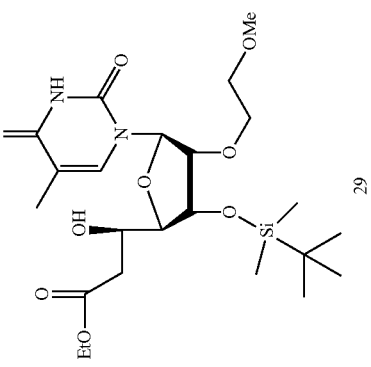
29
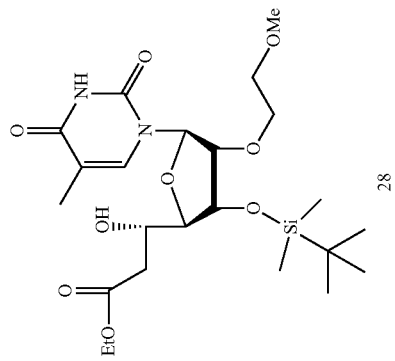
28

Step 1 (Preparation of β-ketoester 26): A solution of BF$_3$.Et$_2$O in anhydrous CH$_2$Cl$_2$ (0.5 equiv) is added dropwise into a solution of aldehyde 25 and ethyl diazoacetate (2 equiv) in anhydrous CH$_2$Cl$_2$ under Ar at 0° C. The mixture is stirred at 0° C. for 2 h and then reaction quenched with sat. aq. NaHCO$_3$. The mixture is extracted with CH$_2$Cl$_2$, dried and evaporated residue purified on silica gel column with hexane/EtOAc solvent system.

Step 2 (Preparation of amidite 27): Into an ice-cold solution of compound 26 in THF is added TBAF/THF (1M, 2 equiv) and the mixture stirred at 0° C. for 1 h. Reaction is quenched with silica, evaporated to dryness and purified by column chromatography. Thus obtained pure compound is dried in high vacuo and then dissolved in acetonitrile. To the solution are added N,N-diisopropylammonium tetrazolide (1 equiv) and 2-cyanoethyl N,N,N',N'-tetraisopropylphosphorbisamidite (2 equiv). The resulting mixture stirred at room temperature for 3 h. The solvent is evaporated and residue purified on silica gel with hexanes +1% Et$_3$N/EtOAc solvent system.

Step 3 (Preparation of alcohols 28 and 29): To the freshly prepared (R)- or (S)-BinapRuBr$_2$ (as described in G. Le Bouc, Tetrahedron: Assymetry 2006, 2006-2012) is added β-ketoester 26 in degassed MeOH. The reaction mixture is stirred under a hydrogen atmosphere for 1 d at 40° C. The solvents are evaporated and further purification by column chromatography gives respective compound 28 or 29.

Step 4 (Preparation of amines 30 and 31): Reductive amination of β-ketoester 26 with selected amine RNH$_2$ gives compounds 30 and 31.

Example 19. Ethyl Heptofuranuronate Analogues

Scheme 19

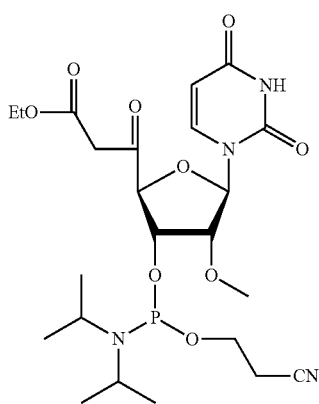

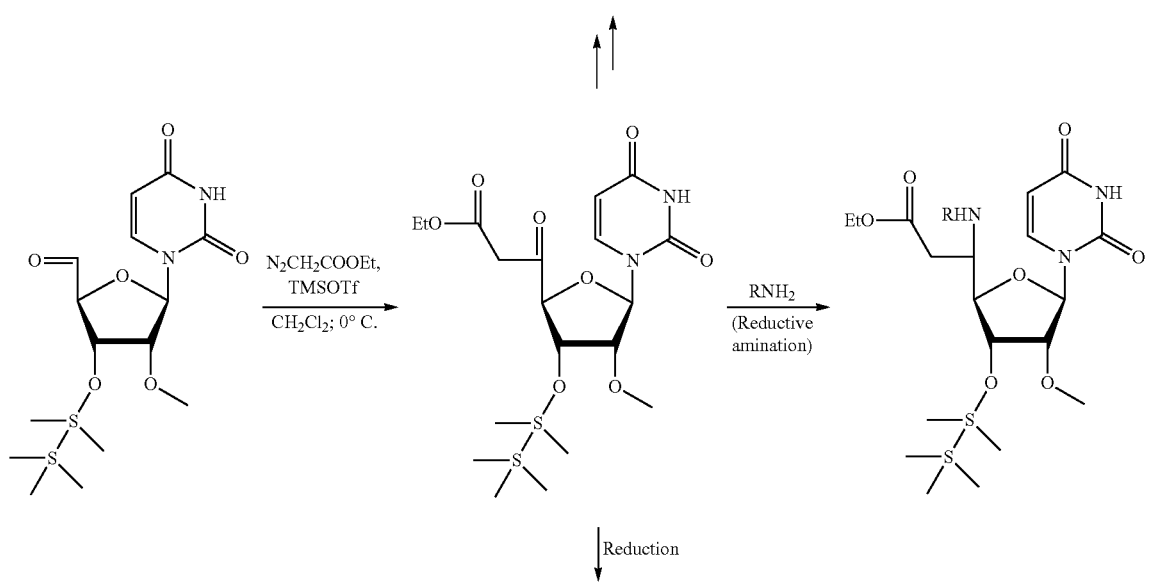

-continued

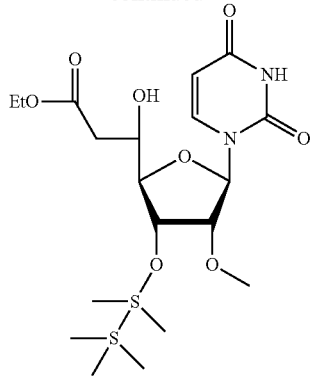

Example 20. RNA 5'-L-Phenylalanine Analogue (37)

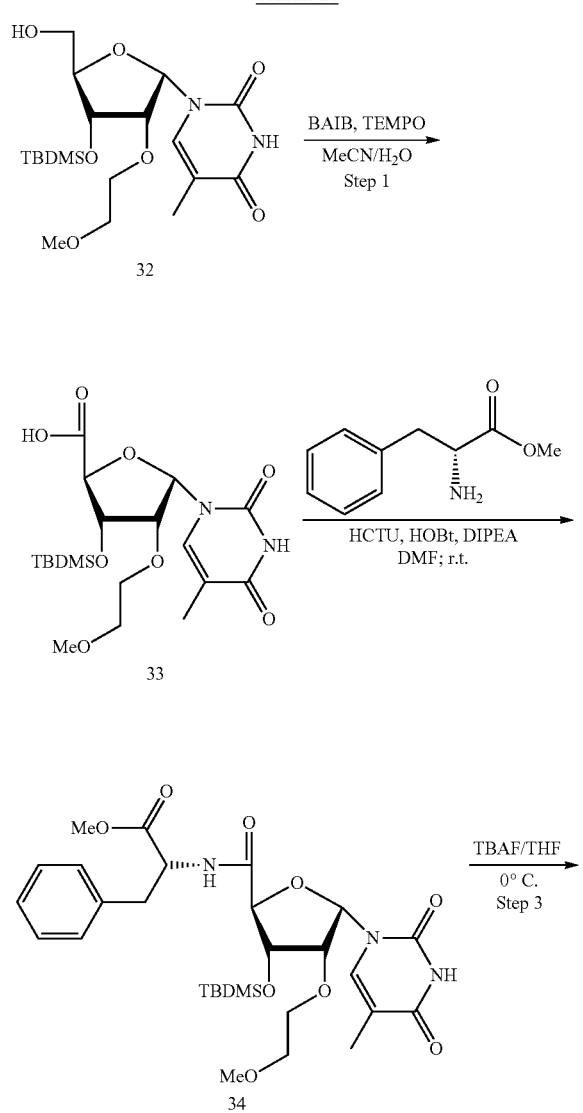

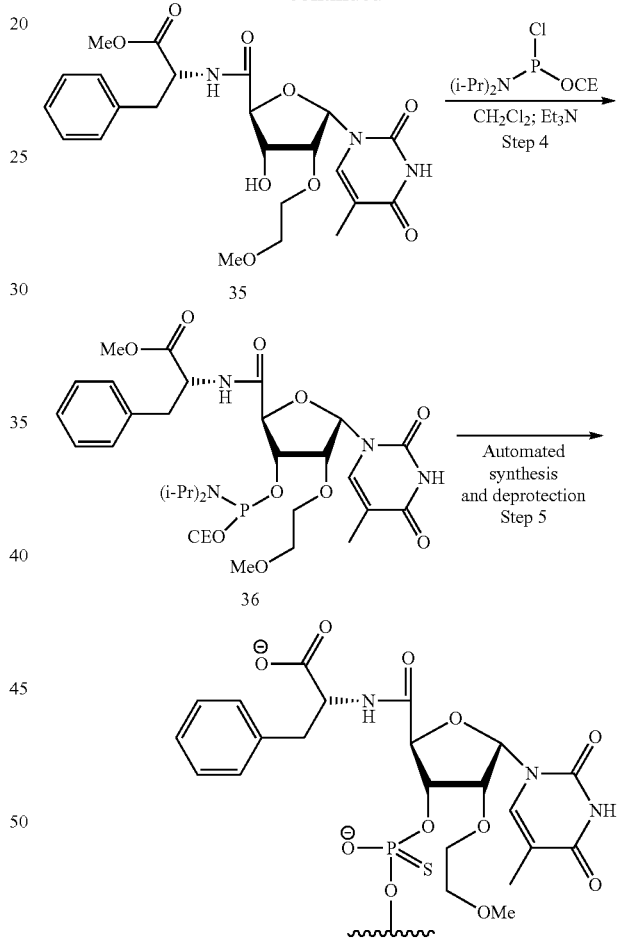

Step 1 (Preparation of 3'-O-tert-butyldimethylsilyl-2'-O-(2-methoxyethyl)-α-uridine 5'-carboxilic acid, 33): BAIB (2.2 equiv), TEMPO (0.2 equiv), and 3'-O-tert-butyldimethylsilyl-2'-O-(2-methoxyethyl)-α-uridine (32) are combined in a flask and to this mixture is added water/acetonitrile (1/1). The reaction mixture is stirred at room temperature for 5 h and then evaporated. The solid residue is treated with acetonitrile and diethyl ether to precipitate the target acid 33.

Step 2 (Preparation of compound 34): Under Ar atmosphere 3'-O-tert-butyldimethylsilyl-2'-O-(2-methoxyethyl)-

α-uridine 5'-carboxilic acid (33), HCTU (1.1 equiv), and HOBt (1.1 equiv) are dissolved in anhydrous DMF. DIPEA (1.1 equiv) is added then and, after 1 min. stirring, solution of methyl-L-phenylalanine hydrochloride (2.2 equiv) in DMF/DIPEA (80/20, v/v) is added via a syringe. The resulting mixture is stirred at room temperature for 2 d and then concentrated. Evaporated residue is purifies on silica gel column with $CH_2Cl_2$-MeOH (0 to 5%).

Step 3 (Preparation of compound 35): To a solution of compound 34 THF at 0° C. is added TBAF/THF (1 M, 2 equiv) and resulting mixture stirred at 0° C. for 1 h. Reaction is quenched then with silica, evaporated to dryness and purified on silica column with $CH_2Cl_2$-MeOH (0 to 10%)

Step 4 (Preparation of compound 36): To a solution of compound 35 in $CH_2Cl_2$ are added DIPEA (3 equiv) and N,N-diisopropyl (2-cyanoethyl)chlorophosphoramidite (1.6 equiv) and the resulting mixture stirred at room temperature for 1.5 h. Reaction is quenched with MeOH and then solvents removed in vacuo. Purification on silica gel column with $CH_2Cl_2$+1% $Et_3$N/MeOH yields target phosphoramidite 36.

Step 5 (Preparation of oligonucleotide 37): Phosphoramidite 36 (0.15 M in MeCN) is coupled onto the 5'-end of RNA on solid support using standard automated oligonucleotide synthesis conditions. Treatment of oligonucleotide on solid support with 0.1 M piperidine in anhydrous acetonitrile for 30 min is followed by hydrolysis with 0.1 aq. NaOH for 30 min. To this mixture is added ammonia in EtOH (4× the volume of aq. NaOH) and heated at 50° C. for 5 h. Filtrate is desalted by RP-HPLC then purified by ion-exchange chromatography followed by desalting to give the target oligonucleotide 37.

Example 21. RNA 5'-L-Serine Analogues 41 and 42

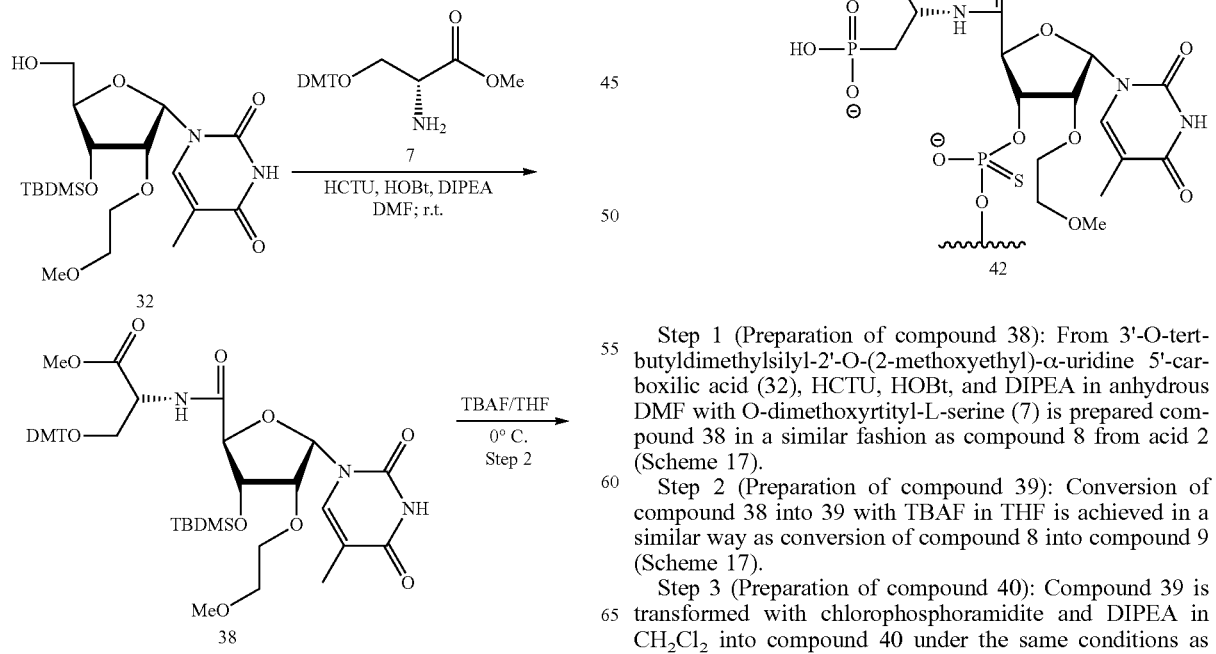

Step 1 (Preparation of compound 38): From 3'-O-tert-butyldimethylsilyl-2'-O-(2-methoxyethyl)-α-uridine 5'-carboxilic acid (32), HCTU, HOBt, and DIPEA in anhydrous DMF with O-dimethoxyrtityl-L-serine (7) is prepared compound 38 in a similar fashion as compound 8 from acid 2 (Scheme 17).

Step 2 (Preparation of compound 39): Conversion of compound 38 into 39 with TBAF in THF is achieved in a similar way as conversion of compound 8 into compound 9 (Scheme 17).

Step 3 (Preparation of compound 40): Compound 39 is transformed with chlorophosphoramidite and DIPEA in $CH_2Cl_2$ into compound 40 under the same conditions as compound 9 into 10 (Scheme 17).

Step 4 (Preparation of compounds 41 and 42): Oligonucleotides 41 and 42 are prepared in the same way from amidite 39 as respective oligonucleotides 11 and 10 from phosphoramidite 10 (Scheme 17).
Example 22
scheme 22
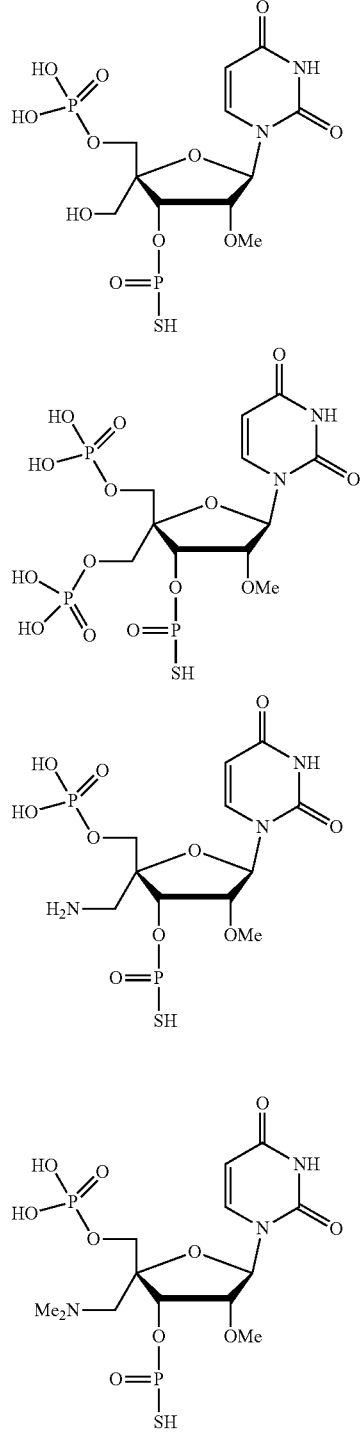
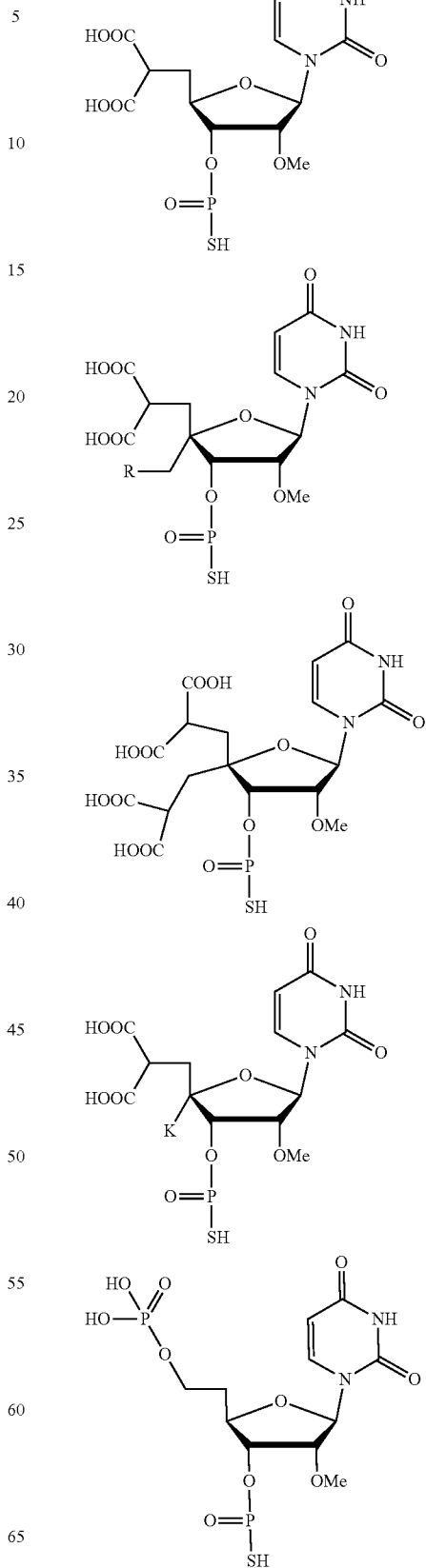

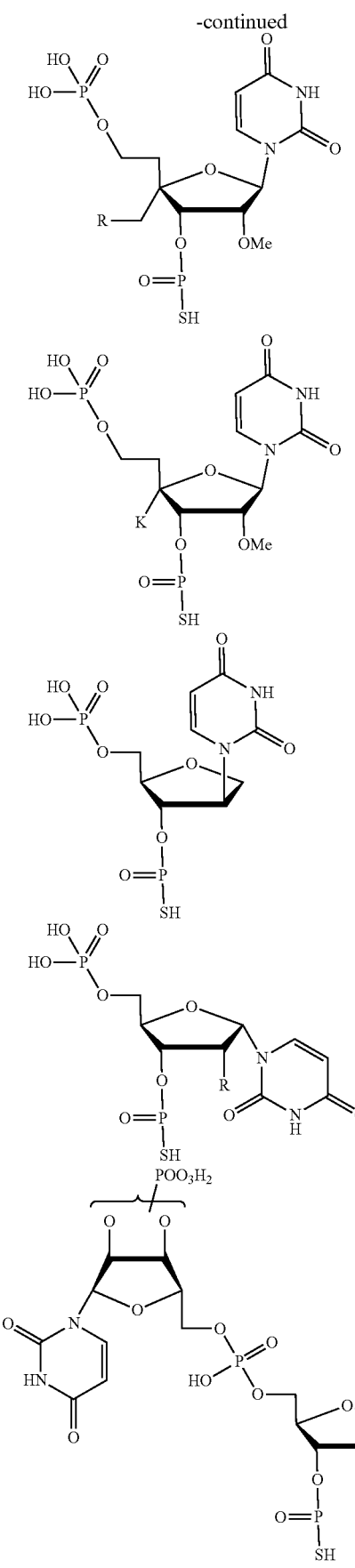
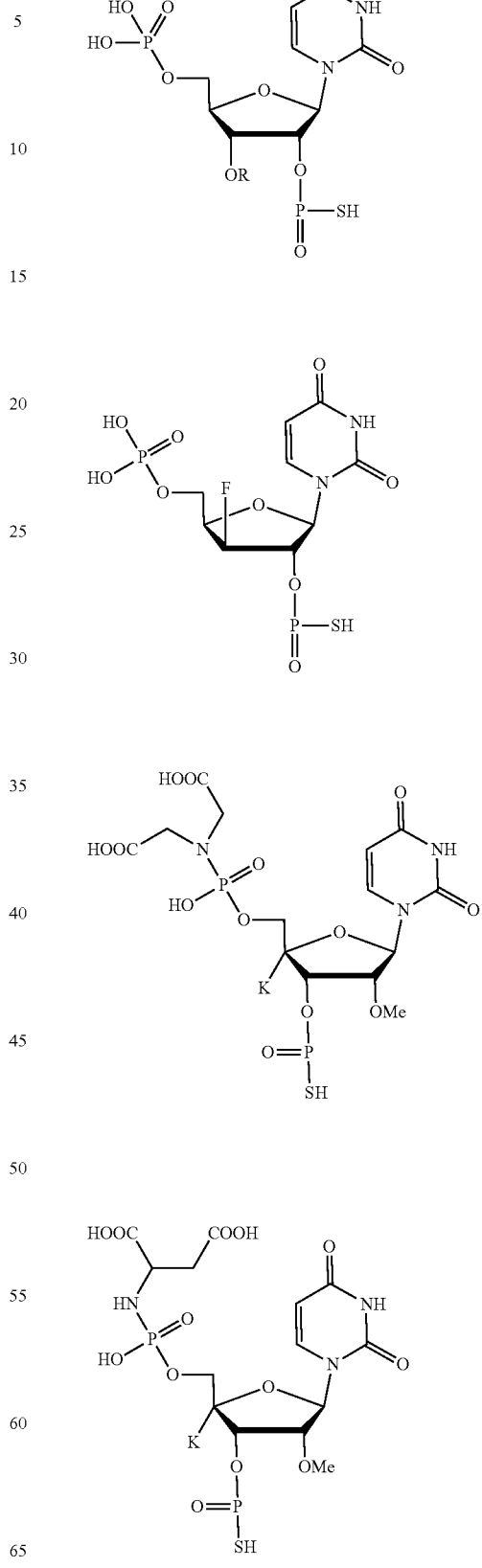

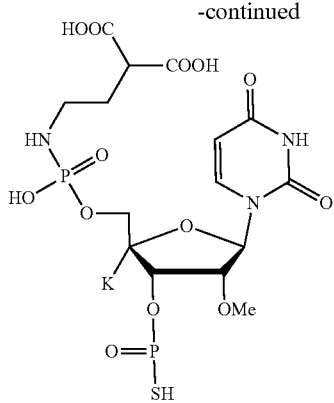

Example 23. In Vitro Silencing Activity of 5′ Terminal-Modified Oligonucleotides: Non-Phosphorus Containing Phosphate Mimics—Anionic Amino Acids Synthesis of the oligonucleotide followed the standard solid-phase automated oligonucleotide synthesis, protection, deprotection and purification conditions. Incorporation of modified nucleosides into the oligonucleotide has been exemplified in Examples 1-21. Modification strategy for preparing an ssRNA (single-stranded RNA) is exemplified in FIG. 1.

ssRNAs with different modifications were synthesized and used as antisense strands. To form siRNAs, the antisense strands were then annealed with a common unmodified sense strand. The siRNAs were designed to cleave PTEN mRNA as the same site as the ssRNA. The sense and antisense strands of the siRNAs have equal length and have 2 nts double overhangs.

Figure 2:
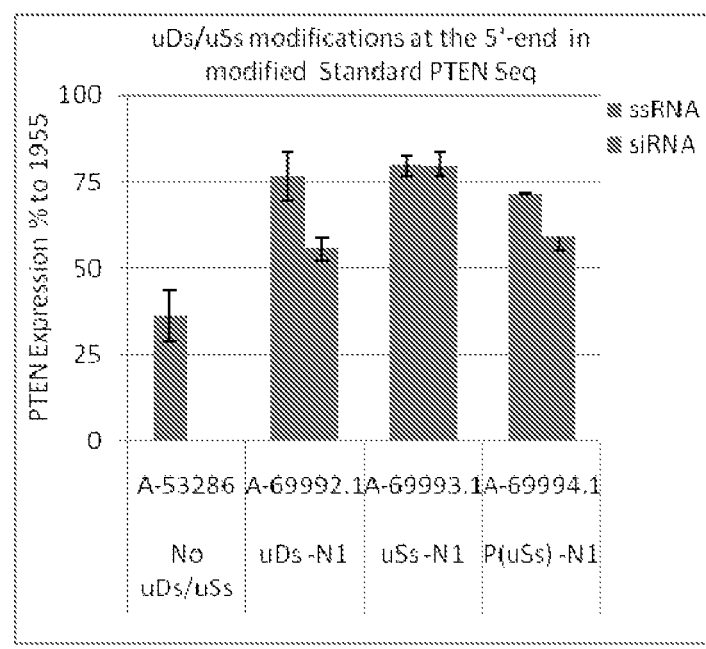
FIG. 2 is a graph showing the results of in vitro silencing of PTEN expression in HeLa cell using the modified oligonucleotides according to certain embodiments of the invention.

The ssRNAs and siRNAs listed in the following table were evaluated for their ability to silence PTEN expression in HeLa cells after reverse transfection with Lipofectamine 2000. Single dose of ssRNAs and siRNAs were determined (at 1 nM in HeLa) 24 hours post-transfection. The expression of PTEN mRNA was quantified by QPCR. The sequence information of the ssRNAs and siRNAs is listed in Table 4 and the results of the in vitro study are compared and shown in FIG. 2.

TABLE 4 ssRNAs and siRNAs activity

| Chemistry | ID | ssRNA KD % | SD | ID | siRNA KD % | SD | AS Sequence |
|---|---|---|---|---|---|---|---|
| No uDs/uSs | A-53286 | 63.9 | 7.5 | | | | P(Teos)UfsgUfscUfscUfsgGfsuCfscUfsusAfscsUfsus(Aeos)(Aeo) |
| uDs | A-69992.1 | 23.3 | 7.1 | AD-38568 | 44.0 | 3.8 | (uDs)UfsgUfscUfscUfsgGfsuCfscUfsusAfscsUfsus(Aeos)(Aeo) |
| uSs | A-69993.1 | 20.3 | 2.9 | AD-38569 | 20.5 | 2.9 | (uSs)UfsgUfscUfscUfsgGfsuCfscUfsusAfscsUfsus(Aeos)(Aeo) |
| P(uSs) | A-69994.1 | 28.6 | 0.4 | AD-P38570 | 40.08 | 4.1 | P(uSs)UfsgUfscUfscUfsgGfsuCfscUfsusAfcsUfsus(Aeos)(Aeo) |

Nf = 2′-F,
n = 2′-O-Me,
eo = 2′-O-MOE,
s = PS

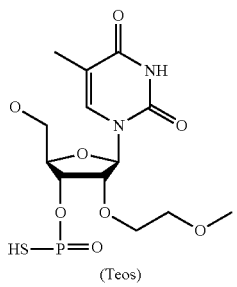

(Teos)

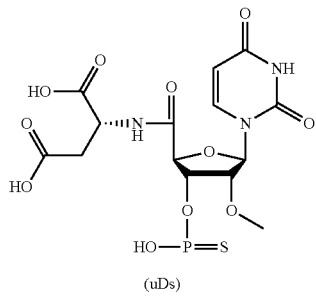

(uDs)
2′-O-methyluridine-5′-carboxamidoaspartate-3′-phosphorothioate

TABLE 4-continued ssRNAs and siRNAs activity

| Chemistry | ssRNA | | | siRNA | | | |
|---|---|---|---|---|---|---|---|
| | ID | KD % | SD | ID | KD % | SD | AS Sequence |

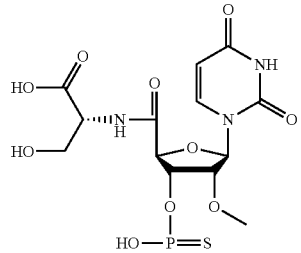

(uSs)

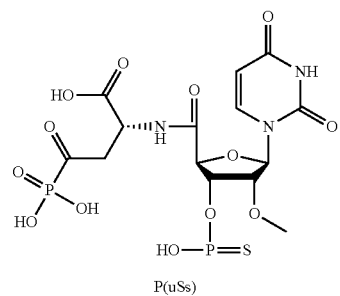

P(uSs)

Example 24. In Vitro Silencing Activity of 5'-Modified siRNAs: Non-Phosphorus Containing Phosphate Mimics—Dicarboxylate Synthesis of the oligonucleotide followed the standard solid-phase automated oligonucleotide synthesis, protection, deprotection and purification conditions. Incorporation of modified nucleosides into the oligonucleotide has been exemplified in Examples 1-21. Modification strategy for preparing an ssRNA (single-stranded RNA) is exemplified in FIG. 1.

ssRNAs with different modifications were synthesized and used as antisense strands. To form siRNAs, the antisense strands were then annealed with a common unmodified sense strand. The siRNAs were designed to cleave PTEN mRNA as the same site as the ssRNA. The sense and antisense strands of the siRNAs have equal length and have 2 nts double overhangs.

The ssRNAs and siRNAs listed in the following table were evaluated for their ability to silence PTEN expression in HeLa cells after reverse transfection with Lipofectamine 2000. $IC_{50}$s of ssRNAs and siRNAs were determined (DRC 20-0.0004 nM in HeLa) 24 hours post-transfection. The expression of PTEN mRNA was quantified by QPCR. The sequence information of the ssRNAs and siRNAs and the results of the in vitro study are compared and shown in Table 5.

TABLE 5 ssRNAs and siRNAs activity

| ssRNA | | | siRNA | |
|---|---|---|---|---|
| SS-ID | IC50 (nM) | AS Sequence (5'-3') | AD-ID | IC50 (nM) |
| A-53286 | 2.362 | P(Teos)UfsgUfscUfscUfsgGfsuCfscUfsusAfscsUfsus(Aeos)(Aeo) | — | — |
| A-63802 | 0.140 | P(T5mReos)UfsgUfscUfscUfsgGfsuCfscUfsusAfscsUfsus(Aeos)(Aeo) | AD-22859 | 0.121 |
| A-83998 | ~15 | Q133sUfsgUfscUfscUfsgGfsuCfscUfsusAfscsUfsus(Aeos)(Aeo) | AD-39987 | 0.212 |

TABLE 5-continued ssRNAs and siRNAs activity

| ssRNA | | | siRNA | |
|---|---|---|---|---|
| SS-ID | IC50 (nM) | AS Sequence (5'-3') | AD-ID | IC50 (nM) |

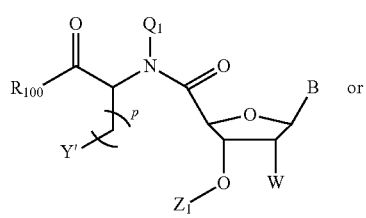

Teos

T5mReos

Q133s

EQUIVALENTS

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

The invention claimed is:

1. A compound represented by one the following formulas:

(2-a)

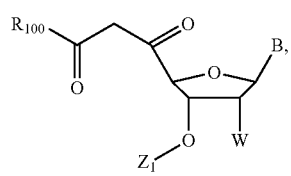

(2-c)

wherein:

$X_{10}$, $Y_{10}$ and $Z_{10}$ are each independently O;

$Z_1$ is a phosphoramidite or an oligonucleotide;

B is selected from the group consisting of hydrogen, aliphatic, substituted aliphatic, natural nucleobase, modified nucleobase and universal base;

W is H, halogen, $OR_{10}$, $SR_{10}$, $NQ_1Q_2$, substituted or unsubstituted aliphatic, substituted or unsubstituted aryl, substituted or unsubstituted heteroaryl, substituted or unsubstituted cycloalkyl, substituted or unsubstituted heterocyclyl, protecting group, reactive phosphorus group, or oligonucleotide;

$Q_1$ and $Q_2$ are each independently selected from the group consisting of H, OH, substituted or unsubstituted aliphatic, substituted or unsubstituted acyl, substituted or unsubstituted carboxyl, substituted or unsubstituted aryl, substituted or unsubstituted heteroaryl, substituted or unsubstituted heterocyclyl, and substituted or unsubstituted cycloalkyl;

$R_{100}$ is OH, SH, $NQ_1Q_2$, $(CH_2)_nCOR_{100}$, $(CH_2)_nNQ_1Q_2$, $(CH_2)_n$ OH, $(CH_2)_n$ SH, alkyl, alkoxy, aralkyl, aryl, heterocyclic, heteroaryl, cyclic alkyl, alkenyl, alkynyl, aralkenyl or aralkynyl;

Y' is $OP(Z_{10})(X_{10})Y_{10}$;

n is 1-10;

p is 0-10; and $R_{10}$ is independently hydrogen, substituted or unsubstituted aliphatic, hydroxyl or alkoxy, substituted aliphatic, aryl, arylaliphatic, hydroxyl or alkoxy substituted aryl, hydroxyl or alkoxy substituted arylaliphatic, heteroaryl, heterocyclic, hydroxyl or alkoxy substituted heteroaryl, or hydroxyl or alkoxy substituted heterocyclic.

2. The compound of claim 1, represented by the formula:

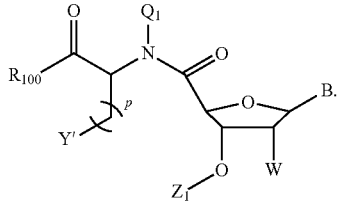

(2-a)

3. The compound of claim 1 wherein n is 1-4.

4. The compound of claim 1 wherein $R_{100}$ is OH or alkoxy.

5. The compound of claim 1, wherein $Z_1$ is said oligonucleotide wherein the oligonucleotide comprises:

1-20 first-type regions, each first-type region independently comprising 1-20 contiguous nucleosides wherein each nucleoside of each first-type region comprises a first-type modification;

0-20 second-type regions, each second-type region independently comprising 1-20 contiguous nucleosides wherein each nucleoside of each second-type region comprises a second-type modification; and 0-20 third-type regions, each third-type region independently comprising 1-20 contiguous nucleosides wherein each nucleoside of each third-type region comprises a third-type modification, wherein the first-type modification, the second-type modification, and the third-type modification are each independently selected from 2'-F, 2'-OCH$_3$, 2'-O(CH$_2$)$_2$ OCH$_3$, BNA, F-HNA, 2'-H and 2'-OH.

6. The compound of claim 5, wherein the oligonucleotide comprises at least one non-phosphodiester internucleoside linkage.

7. The compound of claim 6, wherein the non-phosphodiester internucleoside linkage is selected from a group consisting of phosphorothioate, phosphorodithioate, H-phosphonate, alkyl-phosphonate, phosphoramidate internucleoside linkage, and any combinations thereof.

8. The compound of claim 5, wherein the oligonucleotide comprises one or more regions of alternating 2'-F and 2'-OMe modified nucleotides.

9. The compound of claim 5, wherein the oligonucleotide comprises one or more regions of alternating non-phosphodiester internucleoside linkage and phosphodiester internucleoside linkage.

10. The compound of claim 5, wherein the oligonucleotide comprises one or more alternating regions of (2'-F)-(PS)-(2'-OMe)-(PO).

11. The compound of claim 5, wherein the oligonucleotide comprises at least one ligand conjugate.

12. The compound of claim 5, wherein the oligonucleotide is double stranded comprising a first strand and a second strand.

13. The compound of claim 5, wherein the oligonucleotide is single stranded.

14. The compound of claim 13, wherein the single-stranded oligonucleotide is a single-stranded siRNA.

15. The compound of claim 5, wherein the oligonucleotide is an antisense, an antagomir, a microRNA, a pre-microRNA, an antimir, a ribozyme or an aptamer.

* * * * *